United States Patent
Bruchez et al.

(10) Patent No.: US 9,249,306 B2
(45) Date of Patent: Feb. 2, 2016

(54) QUENCHED DENDRIMERIC DYES FOR FLORESCENCE DETECTION

(75) Inventors: Marcel P. Bruchez, Pittsburgh, PA (US); Lauren A. Ernst, Pittsburgh, PA (US); James Fitzpatrick, La Jolla, CA (US); Chris Szent-Gyorgyi, Pittsburgh, PA (US); Brigitte F. Schmidt, Pittsburgh, PA (US); Alan Waggoner, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 187 days.

(21) Appl. No.: 13/201,226

(22) PCT Filed: Feb. 16, 2010

(86) PCT No.: PCT/US2010/024320
§ 371 (c)(1),
(2), (4) Date: Oct. 20, 2011

(87) PCT Pub. No.: WO2010/096388
PCT Pub. Date: Aug. 26, 2010

(65) Prior Publication Data
US 2012/0058494 A1    Mar. 8, 2012

Related U.S. Application Data

(60) Provisional application No. 61/207,929, filed on Feb. 18, 2009.

(51) Int. Cl.
| | |
|---|---|
| *G01N 21/64* | (2006.01) |
| *C09B 23/06* | (2006.01) |
| *C09B 11/22* | (2006.01) |
| *C09B 11/02* | (2006.01) |
| *C09B 23/08* | (2006.01) |
| *G01N 33/542* | (2006.01) |
| *G01N 33/58* | (2006.01) |

(52) U.S. Cl.
CPC ............... *C09B 11/22* (2013.01); *C09B 11/02* (2013.01); *C09B 23/06* (2013.01); *C09B 23/083* (2013.01); *C09B 23/086* (2013.01); *G01N 33/542* (2013.01); *G01N 33/582* (2013.01)

(58) Field of Classification Search
None
See application file for complete search history.

(56) References Cited

U.S. PATENT DOCUMENTS

| | | |
|---|---|---|
| 4,215,050 A | 7/1980 | Lantzsch |
| 5,096,815 A | 3/1992 | Ladner et al. |
| 5,166,320 A | 11/1992 | Wu et al. |
| 5,198,346 A | 3/1993 | Ladner et al. |
| 5,223,409 A | 6/1993 | Ladner et al. |
| 5,270,163 A | 12/1993 | Gold et al. |
| 5,475,096 A | 12/1995 | Gold et al. |
| 5,496,938 A | 3/1996 | Gold et al. |
| 5,567,588 A | 10/1996 | Gold et al. |
| 5,580,737 A | 12/1996 | Polisky et al. |
| 5,637,459 A | 6/1997 | Burke et al. |
| 5,660,985 A | 8/1997 | Pieken et al. |
| 5,683,867 A | 11/1997 | Biesecker et al. |
| 5,702,892 A | 12/1997 | Mulligan-Kehoe |
| 5,707,796 A | 1/1998 | Gold et al. |
| 5,750,373 A | 5/1998 | Garrard et al. |
| 5,763,189 A | 6/1998 | Buechler et al. |
| 5,821,047 A | 10/1998 | Garrard et al. |
| 5,948,635 A | 9/1999 | Kay et al. |
| 6,127,132 A | 10/2000 | Breitling et al. |
| 6,131,580 A | 10/2000 | Ratner et al. |
| 6,248,558 B1 | 6/2001 | Lin et al. |
| 6,407,213 B1 | 6/2002 | Carter et al. |
| 2003/0165918 A1* | 9/2003 | Nakamura et al. ............. 435/6 |
| 2003/0220502 A1 | 11/2003 | Waggoner et al. |
| 2006/0029936 A9 | 2/2006 | Lee |
| 2008/0213811 A1 | 9/2008 | Vogel et al. |
| 2013/0244891 A1* | 9/2013 | Waggoner et al. ............. 506/9 |

FOREIGN PATENT DOCUMENTS

| | | |
|---|---|---|
| EP | 0043075 A2 | 1/1982 |
| JP | 6447381 A | 2/1989 |
| JP | 8-503994 A | 4/1996 |
| JP | 9-104825 A | 4/1997 |
| JP | 2003-508065 A | 3/2003 |
| WO | 9106309 A1 | 5/1991 |
| WO | 9119813 A1 | 12/1991 |
| WO | 9206180 A1 | 4/1992 |
| WO | 9219749 A1 | 11/1992 |
| WO | 9220316 A2 | 11/1992 |

(Continued)

OTHER PUBLICATIONS

Yoo et al., "Antibody-ligand interactions studied by fluorescence enhancement methods I. Properties of the ligands 4-anilinonaphthalene-1-sulfonate and 6-anilinonaphthalene-2-sulfonate," Immunochemistry, 1970, vol. 7, issue 7, pp. 627-636.*

(Continued)

*Primary Examiner* — Galina Yakovleva
(74) *Attorney, Agent, or Firm* — The Webb Law Firm

(57) ABSTRACT

The present invention presents designs for high extinction quenched "dyedrons" that can be activated by conversion of a single acceptor/quencher in the molecular assembly to a fluorescent state. The quencher is activated by noncovalent binding to a unique complementary expressible fluorogen activating peptide (FAP). In this way, the quencher serves as the homogeneous switch, receiving energy efficiently from each of the donor molecules of the dendronic antenna, and releasing it as fluorescence only when activated by binding. The sum of the extinction of the multiple dyes on the antenna will provide dramatic enhancements in the effective brightness of the probe in standard imaging systems. This approach provides a set of probes with exceptional brightness, specifically targeted to an expressed tag that activates the fluorescence of the dyedron.

41 Claims, 25 Drawing Sheets

(56) References Cited

FOREIGN PATENT DOCUMENTS

| WO | 9222635 A1 | 12/1992 |
|---|---|---|
| WO | 9304701 A1 | 3/1993 |
| WO | 03014743 A2 | 2/2003 |
| WO | 2008092041 A2 | 7/2008 |

OTHER PUBLICATIONS

Jones et al., "Improvements in the Sensitivity of Time Resolved Fluorescence Energy Transfer Assays," Journal of Fluorescence, 2001, vol. 11, issue 1, pp. 13-21.*
Hawker et al., "Preparation of polymers with controlled molecular architecture. A new convergent approach to dendritic macromolecules," J. Am. Chem. Soc., 1990, vol. 112, issue 21, pp. 7638-7647.*
Babendure et al., Aptamers Switch on Fluorescence of Triphenylmethane Dyes, J. Am. Chem. Soc., 2003, pp. 14716-14717 and S1-S3, vol. 125.
Berlier et al., Quantitative Comparison of Long-wavelength Alexa Fluor Dyes to Cy Dyes: Fluorescence of the Dyes and Their Bioconjugates, The Journal of Histochemistry & Cytochemistry, 2003, pp. 1699-1712, vol. 51(12).
Bielinska et al., The interaction of plasmid DNA with polyamidoamine dendrimers: mechanism of complex formation and analysis of alterations induced in nuclease sensitivity and transcriptional activity of the complexed DNA,Biochimica et Biophysical Acta, 1997, pp. 180-190, vol. 1353.
Boder et al., Directed evolution of antibody fragments with monovalent femtomolar antigen-binding affinity, PNAS, Sep. 26, 2000, pp. 10701-10705, vol. 97, No. 20.
Chao et al., Isolating and engineering human antibodies using yeast surface display, Nature Protocols, 2006, pp. 755-768 and 1-page Erratum, vol. 1, No. 2.
Colby et al., Potent inhibition of huntingtin aggregation and cytotoxicity by a disulfide bond-free single-domain intracellular antibody, PNAS, Dec. 21, 2004, pp. 17616-17621, vol. 101, No. 51.
Cwirla et al., Peptides on phage: A vast library of peptides for identifying ligands, Proc. Natl. Acad. Sci. USA, Aug. 1990, pp. 6378-6382, vol. 87.
Derossi et al., Cell Internalization of the Third Helix of the Antennapedia Homeodomain Is Receptor-independent, The Journal of Biological Chemistry Jul. 26, 1996, pp. 18188-18193, vol. 271, No. 30.
Devlin et al., Random Peptide Libraries: A Source of Specific Protein Binding Molecules, Science, Jul. 27, 1990, pp. 404-406, vol. 249.
Fitzpatrick et al., STED nanoscopy in living cells using Fluorogen Activating Proteins, Bioconjug Chem., 2009, 8 pages, vol. 20(10).
Green et al., Autonomous Functional Domains of Chemically Synthesized Human Immunodeficiency Virus Tat Trans-Activator Protein, Cell, Dec. 23, 1988, pp. 1179-1188, vol. 55.
Hanes et al., Ribosome display efficiently selects and evolves high-affinity antibodies in vitro from immune libraries, Proc. Natl. Acad. Sci. USA, Nov. 1998, pp. 14130-14135, vol. 95.
He et al., Antibody-ribosome-mRNA (ARM) complexes as efficient selection particles for in vitro display and evolution of antibody combining sites, Nucleic Acids Research, 1997, pp. 5132-5134, vol. 25, No. 24.
Holt et al., The use of recombinant antibodies in proteomics, Current Opinion in Biotechnology, 2000, pp. 445-449, vol. 11.
Hung et al., Energy Transfer Primers with 5- or 6-Carboxyrhodamine-6G as Acceptor Chromophores, Analytical Biochemistry, 1996, pp. 165-170, vol. 238, Article No. 0270.

Ike et al., Solid phase synthesis of polynucleotides VIII. Synthesis of mixed oligodeoxyribonucleotides by the phosphotriester solid phase method, Nucleic Acids Research, 1983, pp. 477-488, vol. 11, No. 2.
Itakura et al., Expression in *Escherichia coli* of a Chemically Synthesized Gene for the Hormone Somatostatin, Science, Dec. 9, 1977, pp. 1056-1063, vol. 198, No. 4321.
Itakura et al., Synthesis and Use of Synthetic Oligonucleotides, Ann. Rev. Biochem., 1984, pp. 323-356, vol. 53.
Jones et al., Improvements in the Sensitivity of Time Resolved Fluorescence Energy Transfer Assays, Poster presented at the 6th International Conference on Methods and Applications of Fluorescence Spectroscopy, Sep. 12-15, 1999, 1 page.
Klajnert et al., Dendrimers: properties and applications, Acto Biochimica Polonica, 2001, pp. 199-208, vol. 48, No. 1.
Martin et al., Mammalian cell-based optimization of the biarsenical-binding tetracysteine motif for improved fluorescence and affinity, Nature Biotechnology, 2005, pp. 1-7.
Miller, Progress Toward Human Gene Therapy, Blood, Jul. 15, 1990, pp. 271-278, vol. 76, No. 2.
Mujumdar et al., Cyanine Dye Labeling Reagents: Sulfoindocyanine Succinimidyl Esters, Bioconjugate Chemistry, Mar./Apr. 1993, pp. 105-111, vol. 4, No. 2.
Özhalici-Ünal et al., A Rainbow of Fluoromodules: A Promiscuous scFv Protein Binds to and Activates a Diverse Set of Fluorogenic Cyanine Dyes, J Am Chem Soc., Sep. 24, 2008, 8 pages, vol. 130(38).
Patterson et al., Use of the Green Fluorescent Protein and Its Mutants in Quantitative Fluorescence Microscopy, Biophysical Journal, Nov. 1997, pp. 2782-2790, vol. 73.
Rao et al., Integrating cell-level kinetic modeling into the design of engineered protein therapeutics, Nature Biotechnology, Feb. 2005, pp. 191-194, vol. 23, No. 2.
Roberts et al., Directed evolution of a protein: Selection of potent neutrophil elastase inhibitors displayed on M13 fusion phage, Proc. Natl. Acad. Sci. USA, Mar. 1992, pp. 2429-2433, vol. 89.
Scott et al., Searching for Peptide Ligands with an Epitope Library, Science, Jul. 27, 1990, pp. 386-390, vol. 249, No. 4967.
Shaner et al., Improved monomeric red, orange and yellow fluorescent proteins derived from *Discosoma* sp. red fluorescent protein, Nature Biotechnology, Dec. 2004, pp. 1567-1572, vol. 22, No. 12.
Shank et al., Enhanced Photostability of Genetically Encodable Fluoromodules Based on Fluorogenic Cyanine Dyes and a Promiscuous Protein Partner, J. Am. Chem. Soc., 2009, pp. 12960-12969, vol. 131.
Swers et al., Shuffled antibody libraries created by in vivo homologous recombination and yeast surface display, Nucleic Acids Research, Feb. 20, 2004, pp. 1-8, vol. 32, No. 3.
Szent-Gyorgyi et al., Fluorogen-activating single-chain antibodies for imaging cell surface proteins, Nature Biotechnology, Feb. 2008, pp. 235-240, vol. 26, No. 2.
Szidonya et al., Dimerization and oligomerization of G-protein-coupled receptors: debated structures with established and emerging functions, Journal of Endocrinology, 2008, pp. 435-453, vol. 196.
Tratschin et al., Adeno-Associated Virus Vector for High-Frequency Integration, Expression, and Rescue of Genes in Mammalian Cells, Molecular and Cellular Biology, Nov. 1985, pp. 3251-3260, vol. 5, No. 11.
Yeast Display scFv Antibody Library Users Manual, Pacific Northwest National Laboratory, Revision Date: MF031112 (Nov. 12, 2003), Richland, WA.
In Vitro Protein Expression Guide, Chapter Six: Ribosome Display, 2005, pp. 30-33, Promega.

* cited by examiner

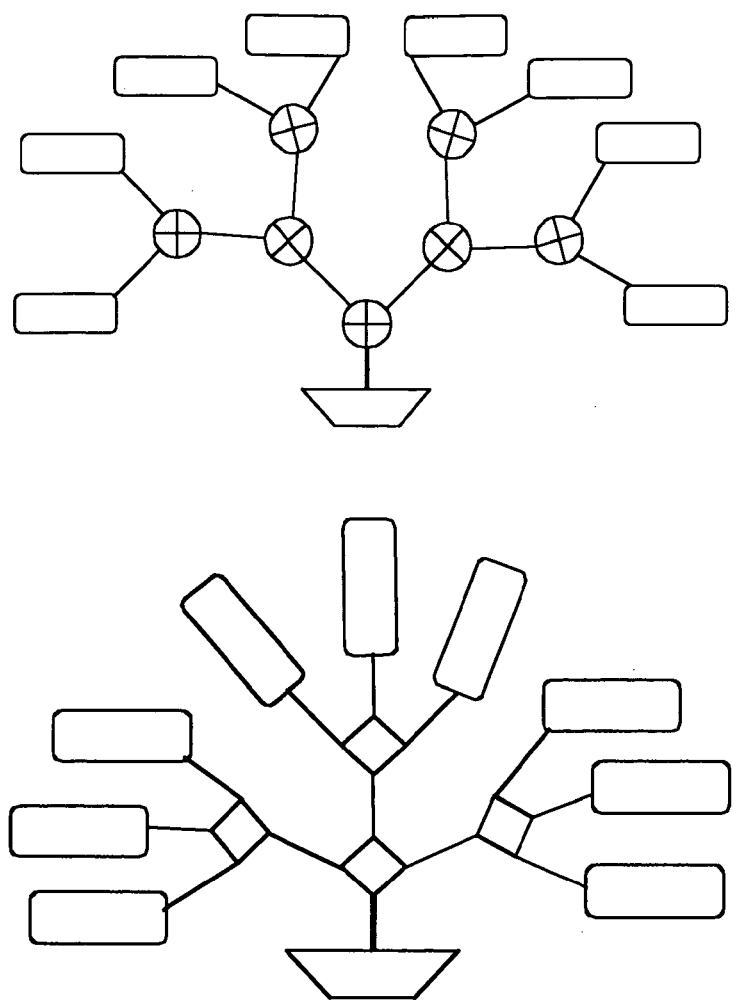
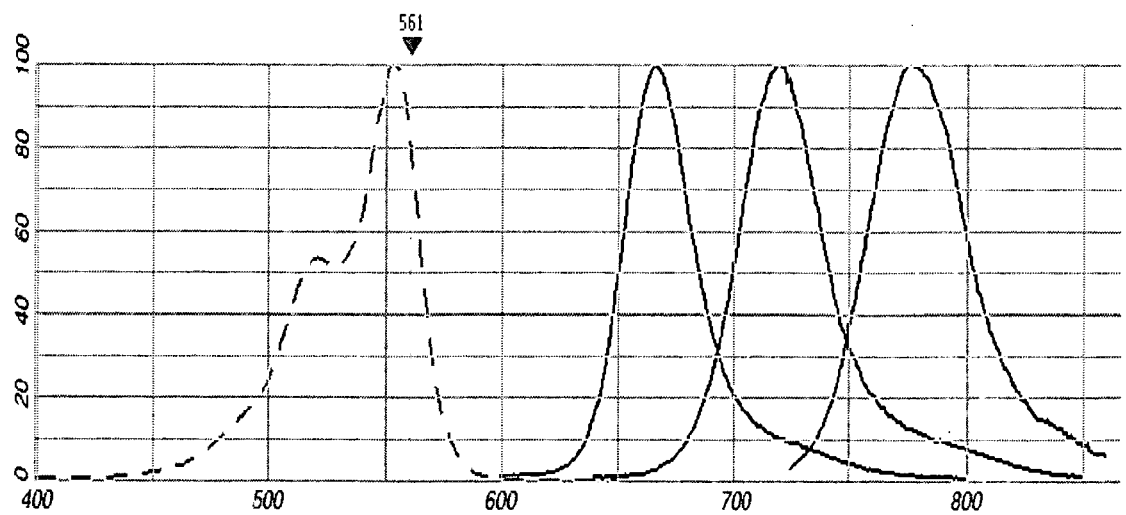
Fig. 2
Fig. 3

L5-MG E52D pPNL6 fusion protein 250aa

MQLLRCFSIFSVIASVLAQELTTICEQIPSPTLESTPYSLSTTTILANGKAMQGVFEYYKSVTFVSNCGS
HPSTTSKGSPINTQYVFKDNSSTIEGRYPYDVPDYALQASGGGGSGGGGSGGGGSASQAVVTQEPSVTVS
PGGTVILTCGSSTGAVTSGHYANWFQQKPGQAPRALIFDTDKKYPWTPGRFSGSLLGVKAALTISDAQPE
DEAEYYCLLSDVDGYLFGGGTQLTVLSGILEQKLISEEDL

Fig. 4A

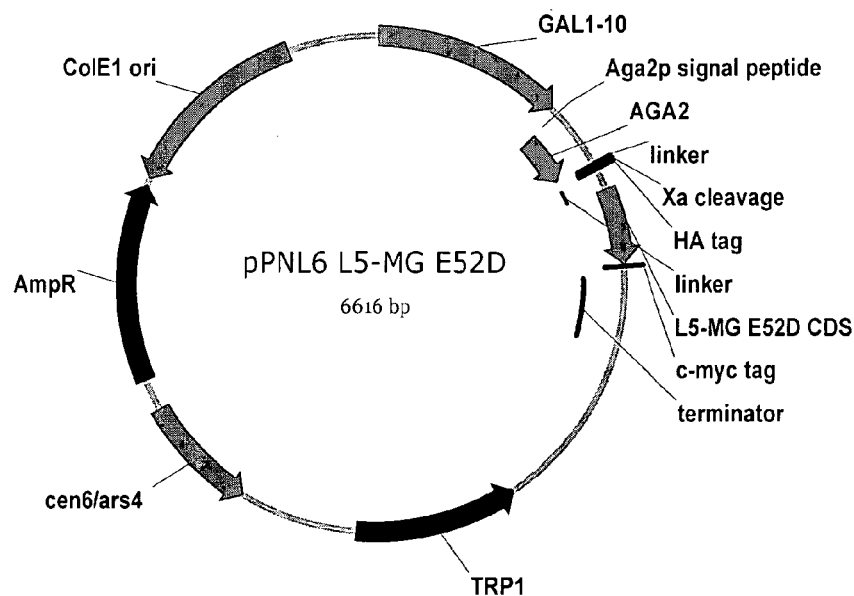

Fig. 4B

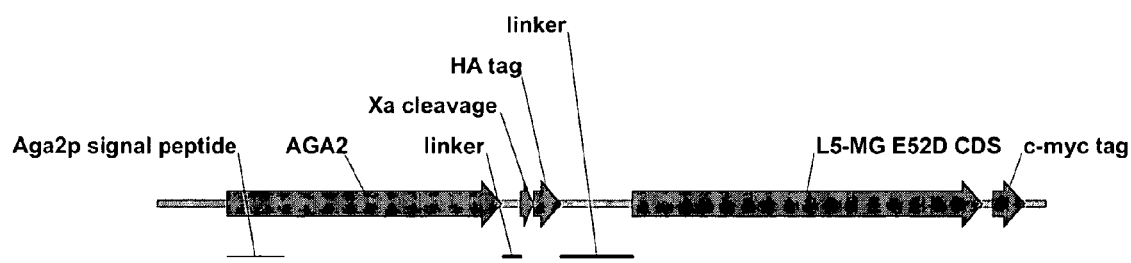

L5-MG E52D fusion protein expressed in pPNL6

Fig. 4C

BCM
$C_{93}H_{112}N_9O_{17}S_4$
1754.71 Da
ESI $[M^{-3}]$ = 1754.73

L5-MG

EAEAY-*QAVVTQEPSVTVSPGGTVILTCGSSTGAVTSGHYANWFQQKPGQAPR*
*ALIFETDKKYPWTPGRFSGSLLGVKAALTISDAQPEDEAEYYCLLSDVDGYL*
*FGGGTQLTVLS*-TGHHHHHH

L5-MG E52D

EAEAY-*QAVVTQEPSVTVSPGGTVILTCGSSTGAVTSGHYANWFQQKPGQAPR*
*ALIFDTDKKYPWTPGRFSGSLLGVKAALTISDAQPEDEAEYYCLLSDVDGYL*
*FGGGTQLTVLS*-TGHHHHHH

L5-MG L91S

EAEAY-*QAVVTQEPSVTVSPGGTVILTCGSSTGAVTSGHYANWFQQKPGQAPR*
*ALIFETDKKYPWTPGRFSGSLLGVKAALTISDAQPEDEAEYYCSLSDVDGYL*
*FGGGTQLTVLS*-TGHHHHHH

L5-MG E52D L91S

EAEAY-*QAVVTQEPSVTVSPGGTVILTCGSGTGAVTSGHYANWFQQKPGQAPR*
*ALIFDTDKKYPWTPGRFSGSLLGVKAALTISDAQPEDEAEYYCSLSDVDGYL*
*FGGGTQLTVLS*-TGHHHHHH

*Fig. 12A*

HL4-MG core 251aa

QVQLVESEGGLVQPGGSLRLSCAASGFTFSSYEMNWVRQAPGKGLEWVSRIDGDGSSTNYADSVKGRFTI
SRDNAKSTLYLQMNSLRAEDTAVYYCTRARYFGSVSPYGMDVWGQGTTVTVSSGILGSGGGGSGGGGSGG
GGSDIRVTQSPSSVSASVGDRVTISCRASQGIATWLGWYQQKPGKPPQLLIYSASTLQTGVPSRFSGSGS
GTDFTLTISSLQPEDVATYYCQEGSTFPLTFGGGTKVDIKS

H6-MG in PNL6 core 130aa

QVQLQESGPGLVKPSETLSLTCTVSGASISSSHYYWGWIRQPPGKGPEWIGSMYYSGRTYYNPALKSRVT
ISPDKSKNQFFLKLTSVTAADTAVYYCAREGPTHYYDNSGPIPSDEYFQHWGQGTLVTVS

L9-MG secreted form (MG67) (6aa - 114aa) 109aa

SYELTQPPSVSVSPGQTARITCSGDALPKQYTYWYQQKAGQAPVLVIYKDTERPSGIPERFSGTSSGTTV
TLTISGVQAEDEADYYCQSADSSGSYVFFGGGTKVTVLS

*Fig. 12B*

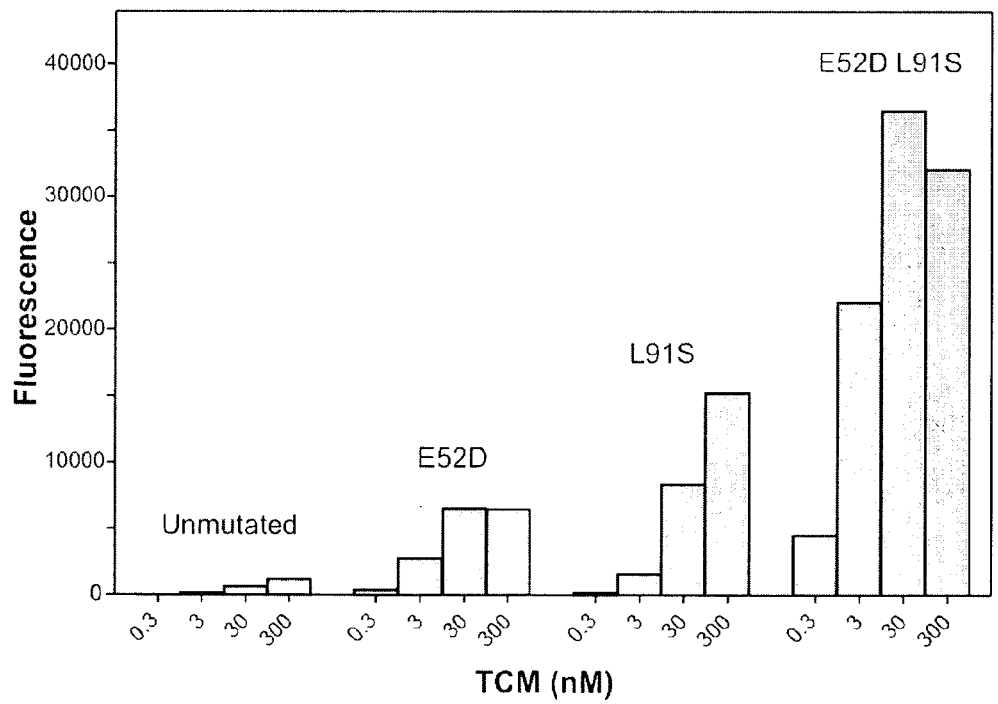

Fig. 13 a)

SEQUENCE LISTING

```
<160> NUMBER OF SEQ ID NOS: 9

<210> SEQ ID NO 1
<211> LENGTH: 250
<212> TYPE: PRT
<213> ORGANISM: Artificial Sequence
<220> FEATURE:
<223> OTHER INFORMATION: L5-MG E52D pPNL6 fusion protein

<400> SEQUENCE: 1

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Lys Asp Asn Ser Ser Thr Ile Glu Gly
                85                  90                  95

Arg Tyr Pro Tyr Asp Val Pro Asp Tyr Ala Leu Gln Ala Ser Gly Gly
            100                 105                 110

Gly Gly Ser Gly Gly Gly Ser Gly Gly Gly Ser Ala Ser Gln
        115                 120                 125

Ala Val Val Thr Gln Glu Pro Ser Val Thr Val Ser Pro Gly Gly Thr
    130                 135                 140

Val Ile Leu Thr Cys Gly Ser Ser Thr Gly Ala Val Thr Ser Gly His
145                 150                 155                 160

Tyr Ala Asn Trp Phe Gln Gln Lys Pro Gly Gln Ala Pro Arg Ala Leu
                165                 170                 175

Ile Phe Asp Thr Asp Lys Lys Tyr Pro Trp Thr Pro Gly Arg Phe Ser
            180                 185                 190

Gly Ser Leu Leu Gly Val Lys Ala Ala Leu Thr Ile Ser Asp Ala Gln
        195                 200                 205

Pro Glu Asp Glu Ala Glu Tyr Tyr Cys Leu Leu Ser Asp Val Asp Gly
    210                 215                 220

Tyr Leu Phe Gly Gly Gly Thr Gln Leu Thr Val Leu Ser Gly Ile Leu
225                 230                 235                 240

Glu Gln Lys Leu Ile Ser Glu Glu Asp Leu
                245                 250

<210> SEQ ID NO 2
<211> LENGTH: 813
<212> TYPE: DNA
<213> ORGANISM: Artificial Sequence
<220> FEATURE:
<223> OTHER INFORMATION: pPNL6 L5-MG E52D nucleotide sequence
```

-continued

<400> SEQUENCE: 2

```
aaaaaacccc ggatcgaatt ctacttcata cattttcaat taagatgcag ttacttcgct    60
gttttttcaat attttctgtt attgcttcag ttttagcaca ggaactgaca actatatgcg   120
agcaaatccc ctcaccaact ttagaatcga cgccgtactc tttgtcaacg actactattt   180
tggccaacgg gaaggcaatg caaggagttt ttgaatatta caaatcagta acgtttgtca   240
gtaattgcgg ttctcacccc tcaacaacta gcaaaggcag ccccataaac acacagtatg   300
tttttaagga caatagctcg acgattgaag gtagataccc atacgacgtt ccagactacg   360
ctctgcaggc tagtggtggt ggtggttctg gtggtggtgg ttctggtggt ggtggttctg   420
ctagccaggc tgtggtgact caggagccgt cagtgactgt gtccccagga gggacagtca   480
ttctcacttg tggctccagc actggagctg tcaccagtgg tcattatgcc aactggttcc   540
agcagaaacc tggccaagcc cccagggcac ttatatttga caccgacaag aaatatccct   600
ggacccctgg ccgattctca ggctccctcc ttggggtcaa ggctgccctg accatctcgg   660
atgcgcagcc tgaagatgag gctgagtatt actgtttgct ctccgacgtt gacggttatc   720
tgttcggagg aggcacccag ctgaccgtcc tctccggaat tctagaacaa aagcttattt   780
ctgaagaaga cttgtaatag ctcggcggcc gca                                813
```

<210> SEQ ID NO 3
<211> LENGTH: 123
<212> TYPE: PRT
<213> ORGANISM: Artificial Sequence
<220> FEATURE:
<223> OTHER INFORMATION: scFv sequence

<400> SEQUENCE: 3

Glu Ala Glu Ala Tyr Gln Ala Val Val Thr Gln Glu Pro Ser Val Thr
1               5                   10                  15

Val Ser Pro Gly Gly Thr Val Ile Leu Thr Cys Gly Ser Ser Thr Gly
            20                  25                  30

Ala Val Thr Ser Gly His Tyr Ala Asn Trp Phe Gln Gln Lys Pro Gly
        35                  40                  45

Gln Ala Pro Arg Ala Leu Ile Phe Glu Thr Asp Lys Lys Tyr Pro Trp
    50                  55                  60

Thr Pro Gly Arg Phe Ser Gly Ser Leu Leu Gly Val Lys Ala Ala Leu
65                  70                  75                  80

Thr Ile Ser Asp Ala Gln Pro Glu Asp Glu Ala Glu Tyr Tyr Cys Leu
                85                  90                  95

Leu Ser Asp Val Asp Gly Tyr Leu Phe Gly Gly Gly Thr Gln Leu Thr
            100                 105                 110

Val Leu Ser Thr Gly His His His His His
        115                 120

<210> SEQ ID NO 4
<211> LENGTH: 123
<212> TYPE: PRT
<213> ORGANISM: Artificial Sequence
<220> FEATURE:
<223> OTHER INFORMATION: scFv

<400> SEQUENCE: 4

Glu Ala Glu Ala Tyr Gln Ala Val Val Thr Gln Glu Pro Ser Val Thr
1               5                   10                  15

Val Ser Pro Gly Gly Thr Val Ile Leu Thr Cys Gly Ser Ser Thr Gly
            20                  25                  30

Ala Val Thr Ser Gly His Tyr Ala Asn Trp Phe Gln Gln Lys Pro Gly
            35                  40                  45

Gln Ala Pro Arg Ala Leu Ile Phe Asp Thr Asp Lys Lys Tyr Pro Trp
    50                  55                  60

Thr Pro Gly Arg Phe Ser Gly Ser Leu Leu Gly Val Lys Ala Ala Leu
65                  70                  75                  80

Thr Ile Ser Asp Ala Gln Pro Glu Asp Glu Ala Glu Tyr Tyr Cys Leu
                85                  90                  95

Leu Ser Asp Val Asp Gly Tyr Leu Phe Gly Gly Gly Thr Gln Leu Thr
                100                 105                 110

Val Leu Ser Thr Gly His His His His His
            115                 120

<210> SEQ ID NO 5
<211> LENGTH: 123
<212> TYPE: PRT
<213> ORGANISM: Artificial Sequence
<220> FEATURE:
<223> OTHER INFORMATION: scFv

<400> SEQUENCE: 5

Glu Ala Glu Ala Tyr Gln Ala Val Val Thr Gln Glu Pro Ser Val Thr
1               5                   10                  15

Val Ser Pro Gly Gly Thr Val Ile Leu Thr Cys Gly Ser Ser Thr Gly
                20                  25                  30

Ala Val Thr Ser Gly His Tyr Ala Asn Trp Phe Gln Gln Lys Pro Gly
            35                  40                  45

Gln Ala Pro Arg Ala Leu Ile Phe Glu Thr Asp Lys Lys Tyr Pro Trp
    50                  55                  60

Thr Pro Gly Arg Phe Ser Gly Ser Leu Leu Gly Val Lys Ala Ala Leu
65                  70                  75                  80

Thr Ile Ser Asp Ala Gln Pro Glu Asp Glu Ala Glu Tyr Tyr Cys Ser
                85                  90                  95

Leu Ser Asp Val Asp Gly Tyr Leu Phe Gly Gly Gly Thr Gln Leu Thr
                100                 105                 110

Val Leu Ser Thr Gly His His His His His
            115                 120

<210> SEQ ID NO 6
<211> LENGTH: 123
<212> TYPE: PRT
<213> ORGANISM: Artificial Sequence
<220> FEATURE:
<223> OTHER INFORMATION: scFv

<400> SEQUENCE: 6

Glu Ala Glu Ala Tyr Gln Ala Val Val Thr Gln Glu Pro Ser Val Thr
1               5                   10                  15

Val Ser Pro Gly Gly Thr Val Ile Leu Thr Cys Gly Ser Gly Thr Gly
                20                  25                  30

Ala Val Thr Ser Gly His Tyr Ala Asn Trp Phe Gln Gln Lys Pro Gly
            35                  40                  45

Gln Ala Pro Arg Ala Leu Ile Phe Asp Thr Asp Lys Lys Tyr Pro Trp
    50                  55                  60

Thr Pro Gly Arg Phe Ser Gly Ser Leu Leu Gly Val Lys Ala Ala Leu
65                  70                  75                  80

Thr Ile Ser Asp Ala Gln Pro Glu Asp Glu Ala Glu Tyr Tyr Cys Ser
                85                  90                  95

```
Leu Ser Asp Val Asp Gly Tyr Leu Phe Gly Gly Gly Thr Gln Leu Thr
            100                 105                 110

Val Leu Ser Thr Gly His His His His His His
        115                 120

<210> SEQ ID NO 7
<211> LENGTH: 251
<212> TYPE: PRT
<213> ORGANISM: Artificial Sequence
<220> FEATURE:
<223> OTHER INFORMATION: scFv

<400> SEQUENCE: 7

Gln Val Gln Leu Val Glu Ser Glu Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Arg Ile Asp Gly Asp Gly Ser Ser Thr Asn Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Arg Tyr Phe Gly Ser Val Ser Pro Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Ser Gly Gly Gly Gly Ser Asp
    130                 135                 140

Ile Arg Val Thr Gln Ser Pro Ser Ser Val Ser Ala Ser Val Gly Asp
145                 150                 155                 160

Arg Val Thr Ile Ser Cys Arg Ala Ser Gln Gly Ile Ala Thr Trp Leu
                165                 170                 175

Gly Trp Tyr Gln Gln Lys Pro Gly Lys Pro Pro Gln Leu Leu Ile Tyr
            180                 185                 190

Ser Ala Ser Thr Leu Gln Thr Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Val Ala Thr Tyr Tyr Cys Gln Glu Gly Ser Thr Phe Pro Leu Thr
225                 230                 235                 240

Phe Gly Gly Gly Thr Lys Val Asp Ile Lys Ser
                245                 250

<210> SEQ ID NO 8
<211> LENGTH: 130
<212> TYPE: PRT
<213> ORGANISM: Artificial Sequence
<220> FEATURE:
<223> OTHER INFORMATION: scFv

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30
```

```
His Tyr Tyr Trp Gly Trp Ile Arg Gln Pro Pro Gly Lys Gly Pro Glu
        35                  40                  45

Trp Ile Gly Ser Met Tyr Tyr Ser Gly Arg Thr Tyr Tyr Asn Pro Ala
    50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
            115                 120                 125

Val Ser
    130

<210> SEQ ID NO 9
<211> LENGTH: 109
<212> TYPE: PRT
<213> ORGANISM: Artificial Sequence
<220> FEATURE:
<223> OTHER INFORMATION: scFv

<400> SEQUENCE: 9

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Ala Gly Gln Ala Pro Val Leu Val Ile Tyr
        35                  40                  45

Lys Asp Thr Glu Arg Pro Ser Gly Ile Pro Glu Arg Phe Ser Gly Thr
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ser Tyr
                85                  90                  95

Val Phe Phe Gly Gly Gly Thr Lys Val Thr Val Leu Ser
            100                 105
```

QUENCHED DENDRIMERIC DYES FOR FLORESCENCE DETECTION

CROSS REFERENCE TO RELATED APPLICATIONS

This application is a National Stage of International Patent Application No. PCT/US2010/024320, filed Feb. 16, 2010, which claims the benefit of U.S. Provisional Patent Application No. 61/207,929, filed Feb. 18, 2009, which is herein incorporated by reference in its entirety.

This invention was made with government support under the National Institutes of Health Nos. 5U54-RR022241 and R01-NIH 1R01GM086237. The government has certain rights in this invention.

The Sequence Listing associated with this application is filed in electronic format via EFS-Web and is hereby incorporated by reference into the specification in its entirety. The name of the text file containing the Sequence Listing is 112943_ST25.txt. The size of the text file is 12,989 bytes, and the text file was created on Oct. 19, 2011.

Sensitivity of fluorescence detection is often a limitation in obtaining useful information from signals emitted by fluorescent reagents in biomedical research, diagnostics, and drug discovery. The sensitivity of fluorescence detection depends on (1) the number of copies of the fluorescent reagent in the detection system, (2) the efficiency of the detection instrument, and (3) the fluorescence brightness of the fluorescent reagent relative to background fluorescence that arises from endogenous biological fluorophores in the sample and from non-specific association of the fluorescent reagent with the sample. The brightness of the fluorescent reagent, in turn, depends on the quantum efficiency of the dyes in the reagent that produce the fluorescence signal and the light absorbing capability (quantified by the extinction coefficient) of the dyes. This invention is concerned with two important advances in fluorescence detection that are obtained simultaneously as a result. One component of the advance is creation of fluorescent reagents with large effective extinction coefficients that provide larger fluorescence signals at the wavelength of reagent excitation. The other aspect of the advance is that the new reagents are selectively activated to a fluorescent state by a targeted activating agent, otherwise producing low non-specific fluorescence when present in the sample.

SUMMARY

The present invention designs high extinction quenched "dyedrons" that can be activated by conversion of a single acceptor/quencher in the molecular assembly to a fluorescent state. The quencher is activated by noncovalent binding to a unique complementary fluorogen activator, such as an expressible fluorogen activating peptide (FAP). In this way, the quencher serves as the homogeneous switch, receiving energy efficiently from each of the donor molecules of the dendronic antenna, and releasing it as fluorescence only when activated by binding. The sum of the extinction of the multiple dyes on the antenna provides dramatic enhancements in the effective brightness of the probe in standard imaging systems. This approach provides a set of probes with exceptional brightness, specifically targeted to an expressed tag that activates the fluorescence of the dyedron.

BRIEF DESCRIPTION OF THE DRAWINGS

FIG. 3 presents donor excitation and acceptor emission properties targeted. Cy-3 or similar spectral variants will be used for the Donor Arrays, and linked either directly or through an intermediate acceptor to the fluorogen quencher.

FIG. 4A depicts the DNA sequence of a construct encoding the L5-MG E52D pPNL6 fusion protein (SEQ ID NO: 1). FIGS. 4B and 4C depict the construct pPNL6 L5-MG E52D.

FIG. 12A provides the peptide sequences for Dyedron-activating scFvs used in this study (SEQ ID NOS: 3-6). Hyphens designate the core sequences. Additional FAPs are provided in FIG. 12B (SEQ ID NOS: 7-9).

FIG. 13. Improvement of TCM fluoromodules by directed evolution.

DETAILED DESCRIPTION

Figure 1A:
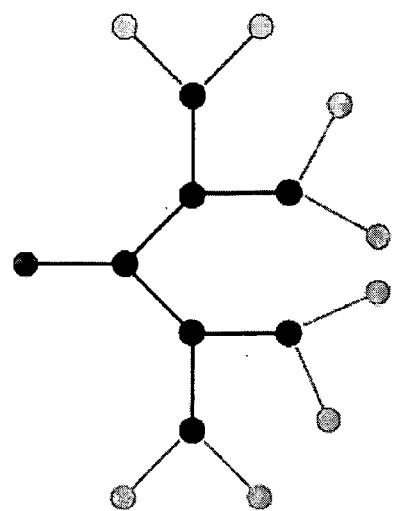
FIG. 1 shows the general concept of quenched dyedron fluorescence activation. A. The quenched dyedron consists of a dendron (black) decorated with two types of dyes, the surface groups with a fluorescent donor (light gray), and the head group coupled to a single quencher (dark gray). B. The binding of the quencher to a specific fluorogen activating peptide (FAP) converts the quencher to an efficient fluorophore/acceptor. C. This activation provides bright emission from the acceptor, coupled with the summed excitation of the donor array, yielding single constructs with 5 to 140-fold higher brightness than existing expressed tags.
Figure 1B:
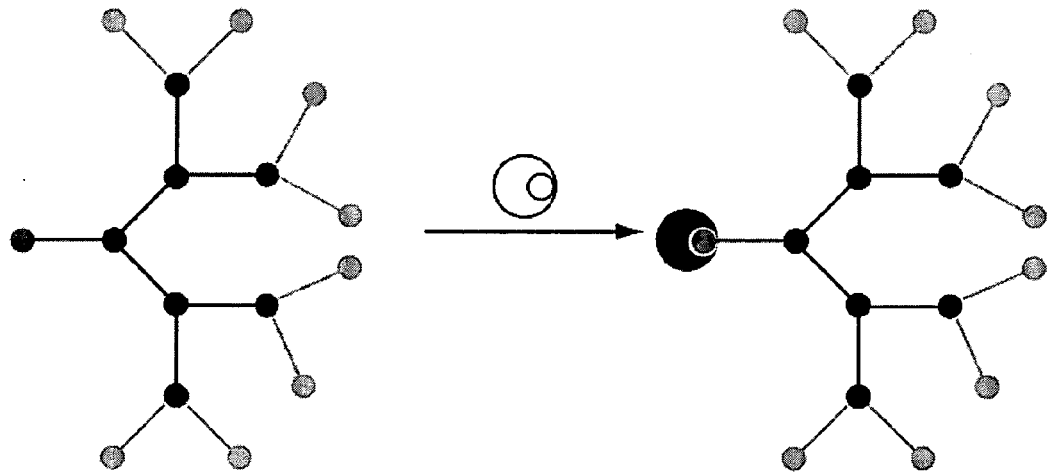
Figure 1C:
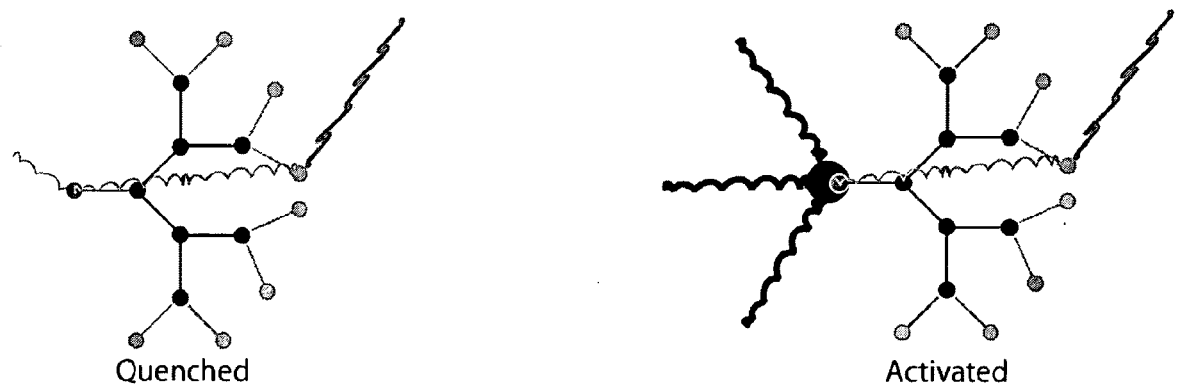
Figures 1, 4D:
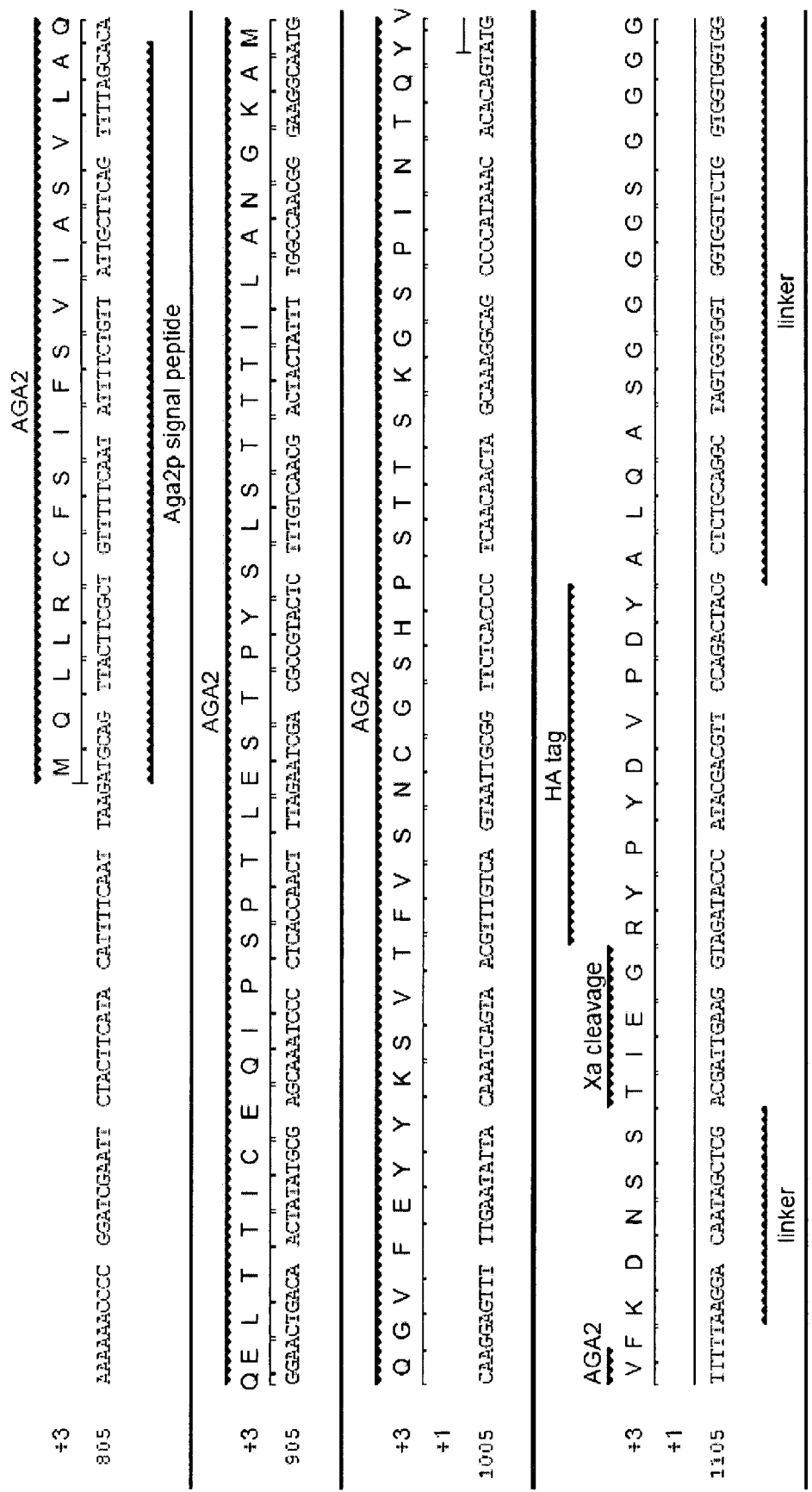
FIG. 4D depicts region of the construct encoding L5-MG E52D mapped onto the nucleotide sequence of the relevant portion of pPNL6 L5-MG E52D (SEQ ID NOS: 1 and 2).

FIG. 1 outlines the approach in the present invention. Dendrons are chemically well defined nanoarchitectures that can be decorated at the surface with a defined and consistent number of molecules. Unlike typical polymer systems, the dendrons are molecularly monodisperse, and each and every dendron possesses the same number and arrangement of functional groups. In addition, work by Balzani and colleagues has demonstrated that a single noncovalently hosted eosin molecule (an acceptor) is capable of quenching the fluorescence of a fully dansyl modified polypropyleneimine dendron up to generation 4 (32 dansyl molecules). Based on this observation, it was reasoned that asymmetric dendrons could be designed to operate as antenna molecules by decoration of the periphery with strongly absorbing dye molecules, and that these could be switched on and off by modulating the quantum yield of a single directly linked quenching molecule. The activation method is reminiscent of many current "beacon" sensor approaches, but does not rely on cleavage of the linker.

Figures 2, 4D:
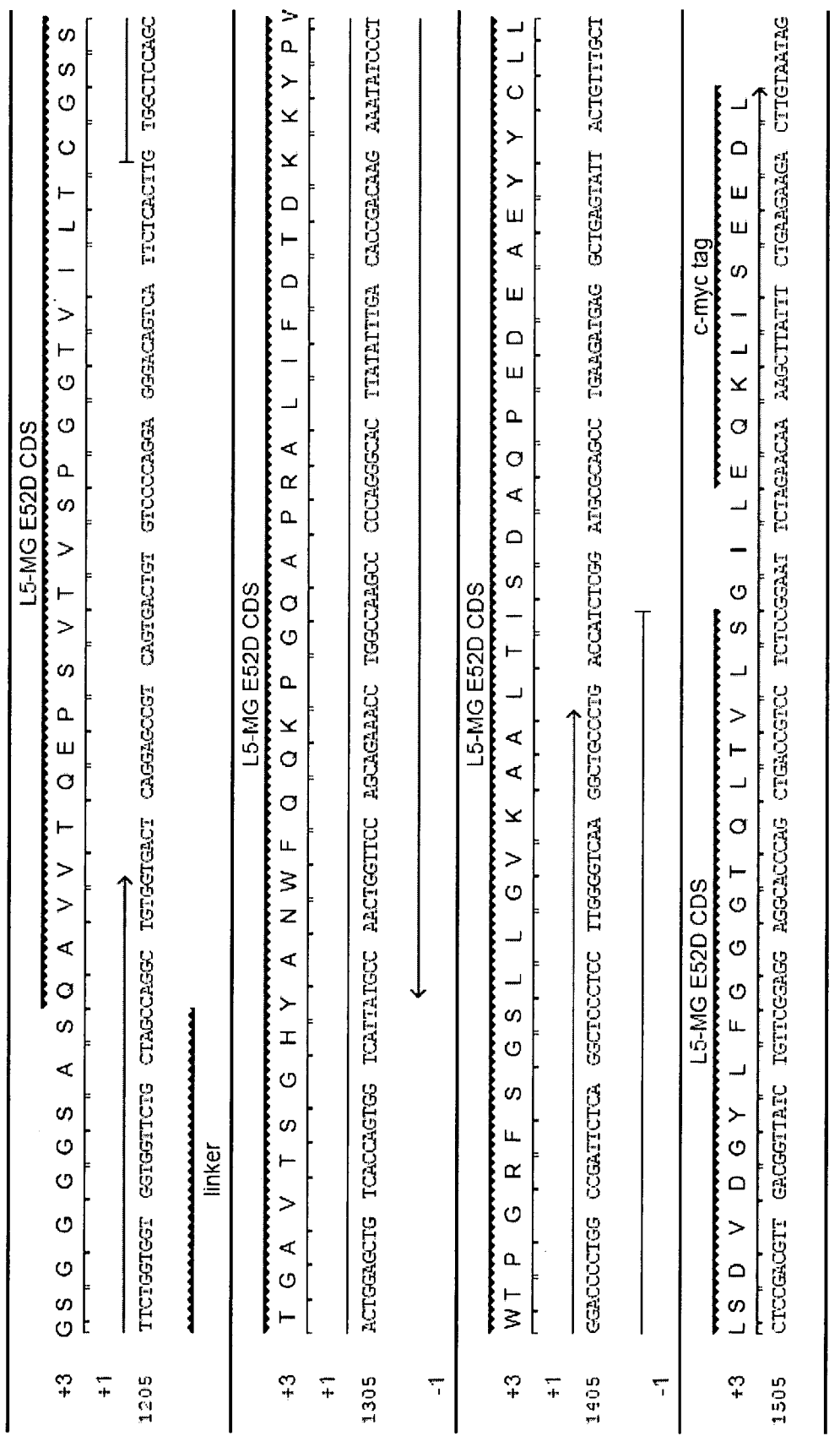
FIG. 2 displays schematics of donor array modules having molar absorptivities, $\epsilon > 10^6$ Left: generation 2 PAMAM dyedron, showing cationic tertiary amines (⊕) in the core; Right: Newkome dyedron with uncharged internal amides (diamonds).

These modules are formed from a donor array linked to a quenching moiety. The properties of donor array, linking unit, and quencher can be characterized and optimized independently. Dendrons are used to form dyedrons with standard available dye molecules, as these readily afford multiple amino groups at the surface and a single sulfhydryl at the head, simplifying preparation of singly-quenched dyedrons. However, a selection of monomers is available to prepare array scaffolds with a range of polarities and carrying a range of charge (FIG. 2). These dendron scaffolds can be assembled like tinker-toys (e.g., click chemistry) to achieve optimal donor dye density and orientation. If highly fluorescent donor arrays are too large or too spectrally remote for efficient quenching by the acceptor, an intermediate acceptor dye can be included at the head of the dendron to collect the excitation energy from the array and relay it to the quencher (acceptor) fluorogen. The spectral properties and spatial orientation of these intermediate acceptors can be manipulated to provide better transfer and Stokes-shifts, especially by fluorogens further red-shifted than malachite green (Targeted properties outlined in FIG. 3).

As illustrated in the examples below, single chain variable fragment (scFv) molecules were selected that are specific for nonfluorescent organic dye molecules, and which cause these dyes to be fluorescent only when they are bound to the protein module in the presence of free dye in solution. Using clones of high affinity (low nanomolar), this binding survives many wash steps, while with clones of low affinity (micromolar), the presence of the dye is required to maintain fluorescence signal. scFv modules are available in yeast display libraries and other display libraries, which can be used to generate specific binding partners for a wide variety of molecules and proteins. One key advantage of this genetically encoded system is that the selected antibodies can be used as expressible protein tags. This allows a relatively small unit (typically ~25 kDa molecular weight for a "whole" scFv, or as small as 11 kDa for a "single domain" scFv) to be expressed as a fusion protein with a specific partner in the cellular context, though the scFv can be attached to a specific partner, such as a cellular protein, ligand, receptor, antibody, etc. by any effective means.

In one embodiment, the invention is a new biological probe strategy that will produce signals that are from 5 to 140-fold brighter than single dyes or fluorescent proteins. Because these dyedrons are significantly red-shifted, signal to background is further enhanced at least 10-fold. In overall detectable signal-to-background ratio, these probes would represent a 100-1000 fold improvement over traditional labels, and a 5-50 fold improvement over the best available QDs. Because these probes are selectively activated by an expressed sequence, remaining otherwise dark, they do not have the wash-out or background problems that plague intrinsically fluorescent molecules, and are not limited by the properties of an independently selected "specificity module" (such as an antibody).

Extended exposure of cells to illumination from high-intensity arc-discharge lamps or lasers can damage cellular physiology, hence enhancement of extinction should be helpful in reducing the excitation powers used. Single molecule studies have relied on red-shifted excitation lasers and sources to obtain longer timescale images without phototoxic effects. While the general rule is "redder is better" due to the lack of biological chromophores (autofluorescence) as one moves away from the blue-green region of the spectrum, the 561 nm laser has gained use in TIRF microscopy for living cells. This laser is well suited to dynamic measurements of living cells, and provides a high signal-to-noise ratio for single molecule experiments. In addition, this laser excites dyes like Cy3 and Alexa 568 quite well, and these probes are known to be good energy transfer donors. For this reason, the probes are designed to excite at 561 nm, and to emit in far red wavelengths from 650 to 800 nm. This will produce probes with optimal signal over background.

As described herein, a fluorogenic dyedron compound is provided, along with a dyedron activation complex, a dyedron activator, and related methods. A dyedron comprises at least two donors (also referred to herein as donor moieties), one or more activatable acceptors and a linking group. A dyedron complex comprises the dyedron and an activator of the acceptor. The emission spectrum of the donor overlaps with the absorption spectrum of the acceptor to achieve fluorescent resonance energy transfer. If the donor spectrum and the acceptor spectrum do not overlap or overlap poorly, a mediator having a spectrum that overlaps with the donors and acceptor, may be used to bridge the spectral gap between the donors and acceptor. When unbound by the activator, the dyedron fluoresces at a different intensity (preferably with lower, insignificant or effectively no fluorescence) or different wavelength than when the acceptor is bound by the activator.

A donor, and where applicable a mediator to bridge a spectral and/or distance gap between a donor and an acceptor, is any molecule or group that can act as a FRET activator to an acceptor. Although donors and acceptors are often referred to herein as independent chemical entities (e.g., Cy3 or Cy5) it is understood that those moieties are attached to the compound, and also are referred to as "donor moieties" and "acceptor moieties". Compounds described herein as being useful as donors and acceptors may be attached to the dyedron by any useful means, according to well-known chemical methods. For example, the compounds can be linked to a dendron or other linker via a pendant carboxyl or amine group that either is depicted in the structures below, or can be added as a linker by any of a variety of methods.

As used herein a donor is a moiety or group that forms part of the dyedron compound. A donor can comprise one type of molecule (e.g., Cy3) or two or more types of donors (e.g., Cy3 and Cy5). Two or more donors may be combined to further shift the emission spectrum of the dyedron away from the absorption spectrum of the donor. In one example, utilizing a cascade approach, a first donor has an absorbance spectrum and an emission spectrum that, at their greatest wavelength does not overlap or overlaps poorly with the absorbance spectrum of the acceptor. In such a case, a mediator that has an absorbance spectrum that overlaps with the emission spectrum of the first donor and an emission spectrum that overlaps with the absorbance spectrum of the acceptor, such that illumination of the dyedron at a wavelength within the absorbance spectrum of the first donor will result in emission by the acceptor.

Of note, a suitable donor need not be fully fluorescent, only capable of efficiently transferring energy to the acceptor to cause the acceptor to fluoresce, fluoresce to a greater extent, or fluoresce at a different wavelength in the presence of (e.g., bound by) an activator when it is excited. Non-limiting examples of suitable donors include: cyanine dyes, fluoresceins, umbelliferones (coumarin compounds), pyrenes, resorufin, rhodamines, hydroxy esters, aromatic acids, styryl dyes, tetramethyl rhodamine dyes, oxazines, thiazines, metal-substituted pthalocyanines and porphyrins, and polycyclic aromatic dyes such as perylenediimides derivatives. Alternatives include the Alexa Dyes (sulfonated coumarin, rhodamine, xanthene (such as fluorescein), and cyanine dyes.) from Molecular Probes, the HiLyte Fluors from AnaSpec, DyLight Fluors from Pierce (Thermo Fisher Scientific), and the ATTO Dye series available from ATTO-TEC and Sigma-Aldrich. Non-limiting examples of FRET pairs or groups suitable for use in dyedrons include (listed in order of donor then acceptor, or, where applicable, donor, mediator and acceptor): Cy3 and MG; Cy3 and acetylenic MG; Cy3, Cy5 and MG; Cy3 and DIR; Cy3, and Cy5 and ICG.

The donors do not necessarily have to be fluorescent. For example, the donor can be an azo dye, or a nitro-modified dye with very low quantum yield, provided the excited state lifetime is long enough to allow intramolecular energy transfer to the proximal acceptor, many of which are available commercially.

The acceptor may be any molecule which produces a detectable signal change in response to a change in environment, namely by binding by an activator, as such, it is deemed "activatable". Likewise, because the acceptor is activatable, the dyedron is considered to be activatable. For example; the signal change may be an increase or decrease in signal intensity, or a change in the type of signal produced (e.g., a shift in wavelength of the emission of the dyedron). For example, suitable reporters include molecules which produce optically detectable signals; for example, fluorescent and chemiluminescent molecules. In certain embodiments, the reporter molecule is a long wavelength fluorescent molecule which permits detection of the reporter signal through a tissue sample; for instance, non-invasive detection of the reporter in conjunction with in vivo applications.

According to certain embodiments, the acceptor is a non-rigidized aromatic system comprising aromatic rings and/or heteroaromatic rings bridged, for example, by a monomethine group.

The acceptor may be a pH sensitive fluorescent dye (pH sensor dye) which shows a spectral or fluorescent intensity change upon interaction with an activator. Interaction of the activator with the acceptor may lead to a shift in the pH of the microenvironment surrounding the acceptor due to the composition of acidic and basic residues on the activator. In turn, the shift in the pH microenvironment leads to a detectable spectral or fluorescent intensity change in the signal of the pH sensitive fluorescent dye molecule associated with the activator. In exemplary embodiments, a pH sensitive dye is selected with an appropriate pKa to lead to an optimal spectral change upon binding to the activator. A variety of pH sensitive dyes suitable for use in are commercially available. In exemplary embodiments, pH sensitive dyes include, for example, fluorescein, umbelliferones (coumarin compounds), pyrenes, resorufin, hydroxy esters, aromatic acids, styryl dyes, tetramethyl rhodamine dyes, and cyanine dyes, and pH sensitive derivatives thereof.

The acceptor may be a polarity sensitive fluorescent dye (polarity sensor dye) which shows a spectral change upon interaction with an activator. Interaction of the activator with a target molecule may lead to a shift in the polarity of the microenvironment surrounding the acceptor due to the composition of polar and/or non-polar residues on the activator. In turn, the change in the polarity of the microenvironment leads to a detectable spectral change in the signal of the polarity sensitive fluorescent dye molecule associated with the activator. A variety of polarity sensitive dyes suitable for use are commercially available. In exemplary embodiments, polarity sensitive dyes include, for example, merocyanine dyes, 5-((((2-iodoacetyl)amino)ethyl)amino)naphthalene-1-sulfonic acid (1,5-IAEDANS), and CPM, and polarity sensitive derivatives of merocyanine dyes, IAEDANS, and CPM.

The acceptor may be a fluorescent dye that is sensitive to changes in the microviscosity of the local environment (restriction sensor dye). Interaction of the activator with an acceptor may lead to a change in the microviscosity in the local environment surrounding the acceptor. In turn, the change in microviscosity may lead to a detectable spectral change in the signal of the mobility sensor dye molecule associated with the activator. For example, an increase of microviscosity upon target binding will restrict the dye and increase the quantum yield of the emitted fluorescence signal. A variety of restriction sensor dyes suitable for use are commercially available. In exemplary embodiments, restriction sensor dyes include, for example, monomethine and trimethine cyanine dyes, and microviscosity sensitive derivatives of monomethine and trimethine cyanine dyes.

In certain embodiments, the acceptor is a dye that exhibits a change in its spectral properties when specifically bound to an activator. A nucleic acid, e.g. an aptamer, may be designed to specifically bind such a dye, for example Malachite Green (see R. Babendure, et al. (2003) J. Am. Chem. Soc. 125: 14716). Such dyes, when in complex with the nucleic acid or protein that is specific for them, change their spectral properties. For example, Malachite Green and its analogs, which is not normally fluorescent, becomes strongly fluorescent when bound to an scFv specific for it. Many di- and tri-arylmethine analogs are good candidates for acceptors and FAP binders described herein. Many di- and tri-arylmethines have been prepared and are reviewed by Thomas Gessner, "Triarylmethane and diarylmethane Dyes", in Ullmann's Encyclopedia of Industrial Chemistry, Wiley (2005). Certain of these unbridged di- and tri-arylmethine dyes and similar dyes described elsewhere and yet to be synthesized, are believed to provide good acceptor dyes structures in dyedrons once they have been appropriately modified according to the goals stated herein.

Analogs of Malachite Green (I) and Phenolphthalein (II) are shown below as representatives.

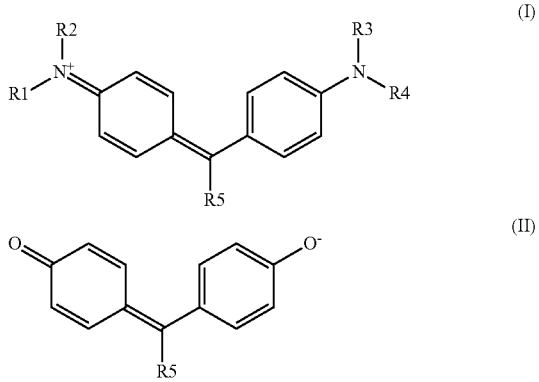

It may be preferred that the R1-R4 groups of the Malachite Green analogs are modified during development of dyedrons in order to control the (1) the wavelength of light absorption and fluorescence, (2) the degree of activation of the acceptor dye, the water solubility of the dyedron, (3) the non-specific binding of the dyedron to cellular components, and (4) the ability or inability of the dyedron to cross biological membranes. The R5 group may be a substituted aryl group as in the Malachite green and Phenolphthalein classes of triarylmethine dyes. The R5 group of the diarylmethine dyes may be some other chemical substituent that accomplishes the goals just stated and in addition to provide a site for linkage of the donor dyes to the energy acceptor part of the dyedron. Other non-phenolic or non-amino groups that do not alter the resonance charge delocalization system that is responsible for the light absorption and emission systems of the dye may be substituted on the aryl rings the di- and triarylmethine structures to achieve the above goals. These groups may be selected from one or more of the atoms or groups listed below as "T". Examples of R1-R4 groups that may be useful for the above goals are —H, —CH$_3$, (CH$_2$)$_n$-T, and substituted aryl where the substituent are selected from atoms or groups listed below as "T" and n=0-6. In these structures "T" may be selected from —H, —OH, COO—, SO$_3^-$, —PO$_4^-$, amide, halogen, substituted single or multiple aryl, ether, polyether, PEGn (where n=1-30), heterocycles containing N, S or O atoms, substituted acetylenic groups, cyano, and carbohydrate groups. In one embodiment of the invention one of R1-R4 contains a linker attached to the donor dyes.

Examples of R5 groups for triarylmethine dyes are listed below where the substituents may be selected from those listed under "T" above. If present, the heteroatoms, X and Y, may be selected from N, O, S, Se, and C(CH$_3$)$_2$. In one embodiment of this invention one of the substituents is a linker attached to the donor dyes.

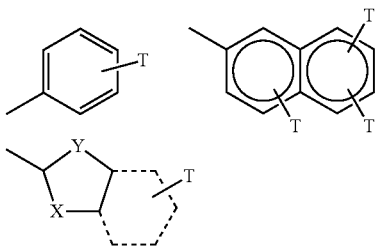

Examples of R5 groups for diarylmethine acceptor dyes may be selected from those listed under "T" above. In a preferred embodiment of this invention one of the substituents is a linker attached to the donor dyes.

The di and triarylmethine dyes may also include additional fused rings as long as the nitrogen or oxygen atoms that are the terminal components of the resonance charge delocalization system that is responsible for the light absorption and emission systems remains intact. These fused ring compounds may be useful to adjust the absorption and emission wavelengths of the acceptor in a desirable direction. One simple example is shown below where the substituents are selected from list "T" above.

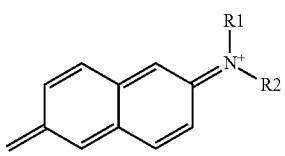

Below are members of cyanine dye family that contain substituted cyanines, merocyanines, styryl and oxonol dyes that are monomethine or contain additional methine groups. According to one embodiment, the acceptor is a diarylmethine or triarylmethine. For example, the acceptor has the structure:

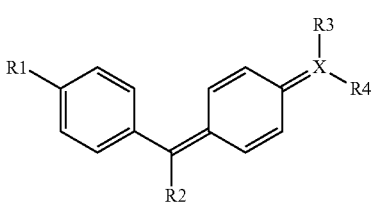

in which R1 is aromatic, heteroaromatic, hydroxyl, amino, N-alkyl, N-alkanolyl (alcohol, e, g. N-hydroxyethyl), R2 is H, cyano, aromatic, heteroaromatic, acetylenic, alkyl, X is N, O, or S and R3 and R4 is alkyl, aryl, hydroxyethyl. The acceptor typically would be attached to the linker/dendron by R2. In certain embodiments, R1 is di-$C_{1-3}$ alkylamino, e.g., —$N(CH_3)_2$, R2 is a substituted phenylacetylene, substituted, e.g., with an amino or substituted amino group, such as —N—$(CH_3)_2$; —N—$(CH_3)((CH_2)_nO(CH_2)_mCOOH)$ in which n and m are independently 1, 2, 3 or 4; or —N—$(CH_3)((CH_2)_2O(CH_2)_3COOH)$, phenyl, —N-alkyl-substituted phenyl, —$O(CH_2)_nR5$ substituted phenyl where n is 1-5 and R5 is carboxyl or amino, and R3 and R4 are independently $C_{1-3}$ alkyl, alkoxyl, alkanolyl, phenyl, $C_{1-3}$ alkyl-substituted phenyl. In one embodiment, R1 is —$N(CH_3)_2$, R2 is one of —$O(CH_2)_3R5$-substituted phenyl and

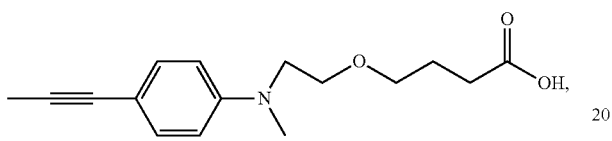

and/or R3 and R4 are $CH_3$. The acceptor is attached to the dyedron via any one of R1-R4.

In other embodiments, the acceptor is a linker-modified derivative of one of:

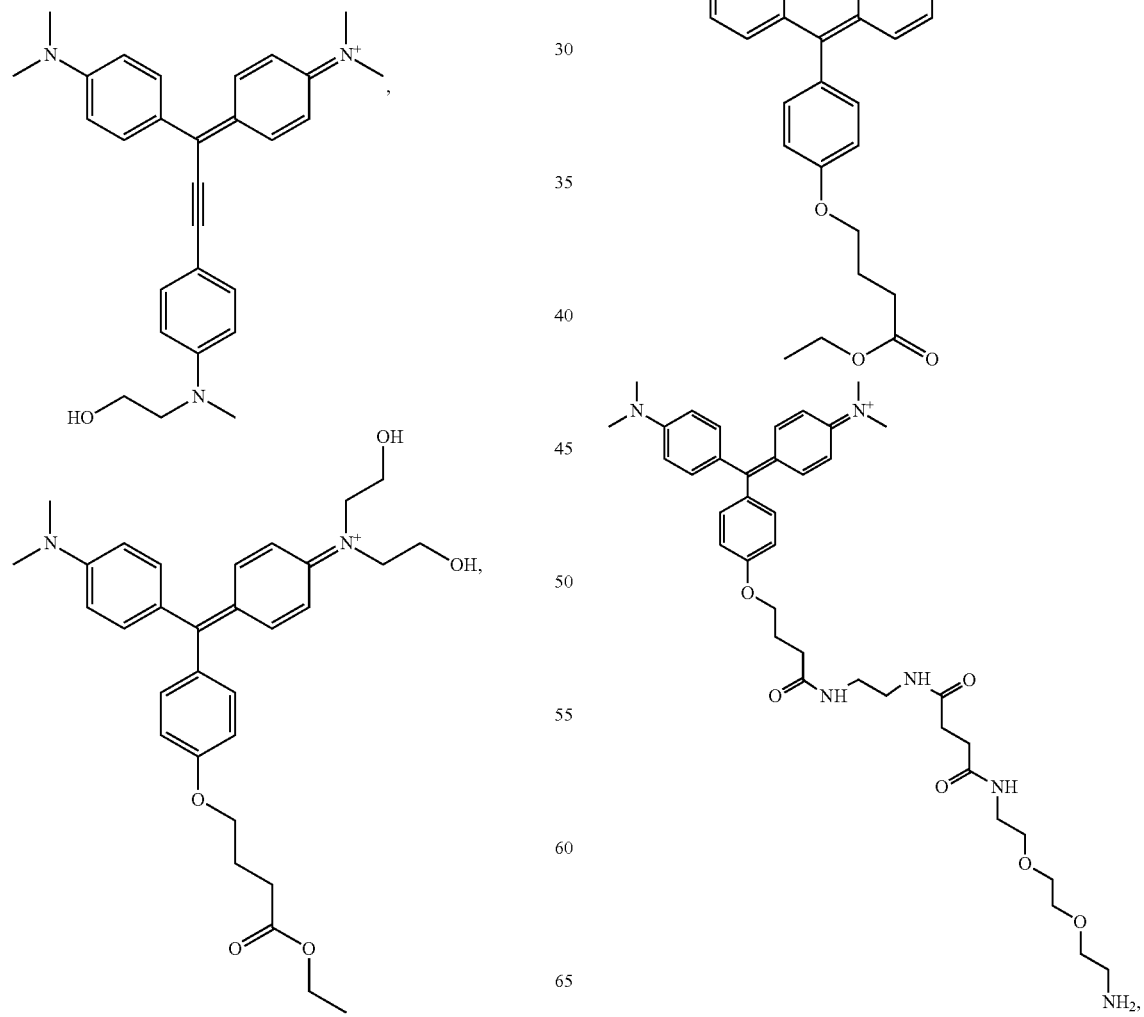

-continued

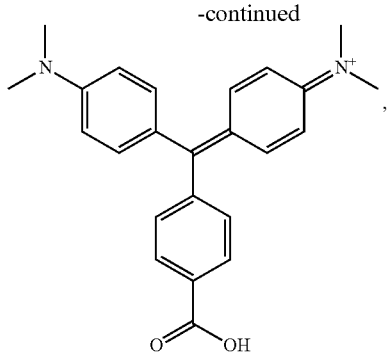

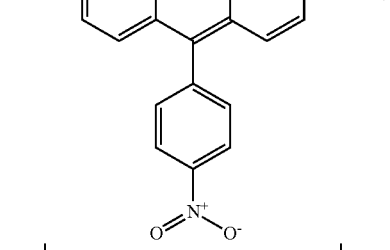, and

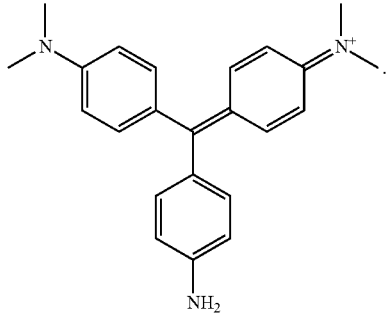

In certain embodiments, the acceptor is represented by structure IV, V and VI:

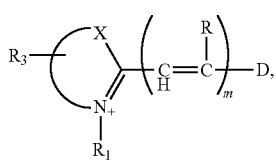    IV

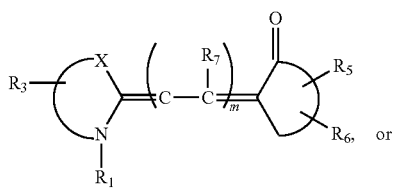    V

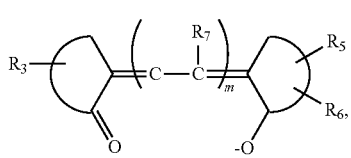    VI wherein: the curved lines represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur; D, if present, is

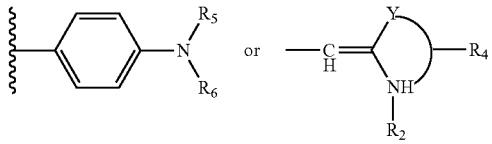

m is 1, 2, 3 or 4, and for cyanine, oxonol and thiazole orange, m can be 0; X and Y are independently selected from the group consisting of O, $S_3$ and —$C(CH_3)_2$—; at least one R1, R2, R3, R4, R5, R6, or R7 is selected from the group consisting of: a moiety that controls water solubility and non-specific binding, a moiety that prevents the reporter molecule from entering the cell through the membrane, a group that comprises, optionally with a linker, biotin a hapten, a His-tag, or other moiety to facilitate the process of isolating the selection entity, a fluorescent label optionally comprising a linker, a photoreactive group, or a reactive group such as a group containing isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-proprionamide, glyoxal, haloacetamido, or aldehyde; further-providing that R1 and R2 may be joined by a —$CHR_8$—CHRs- or —$BF_2$— biradical; wherein; $R_8$ independently for each occurrence is selected from the group consisting of hydrogen, amino, quaternary amino, aldehyde, aryl, hydroxyl, phosphoryl, sulfhydryl, water solubilizing groups, alkyl groups of twenty-six carbons or less, lipid solubilizing groups, hydrocarbon solubilizing groups, groups promoting solubility in polar solvents, groups promoting solubility in nonpolar solvents, and -E-F; and further providing that any of R1, R2, R3, R4, R5, R6, or R7 may be substituted with halo, nitro, cyan, —$CO_2$alkyl, —$CO_2H$, —$CO_2$aryl, $NO_2$, or alkoxy, wherein:

F is selected from the group consisting of hydroxy, protected hydroxy, alkoxy, sulfonate, sulfate, carboxylate, and lower alkyl substituted amino or quartenary amino;

E is spacer group of formula —$(CH_2)_n$- wherein n is an integer from 0-5 inclusively;

alternatively, E is a spacer group of formula —$(CH_2—O—CH_2)_n$— wherein n is an integer from 0-5, inclusively In other embodiments, wherein m=0 in structures IV, V and VI, the following general structures VII, VIII and IX are afforded:

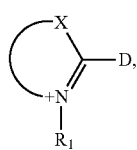    VII

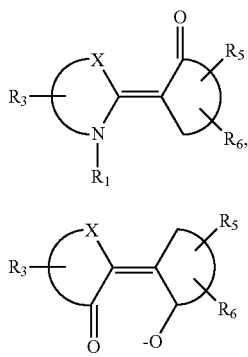

wherein: the curved lines represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur; D, if present, is

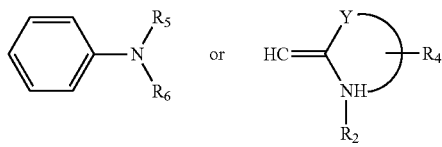

X and Y are independently selected from the group consisting of O, S, and —C(CH$_3$)$_2$—; at least one R1, R2, R3, R4, R5, R6, or R7 is selected from the group consisting of: a moiety that controls water solubility and non-specific binding, a moiety that prevents the reporter molecule from entering the cell through the membrane, a group that comprises, optionally with a linker, biotin, a hapten, a His-tag, or other moiety to facilitate the process of isolating the selection entity, a fluorescent label optionally comprising a linker, a photoreactive group, or a reactive group such as a group containing isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-proprionamide, glyoxal, haloacetamido, or aldehyde; further-providing that R1 and R2 may be joined by a —CHR$_8$—CHRs- or —BF$_2$— biradical; wherein;

R$_8$ independently for each occurrence is selected from the group consisting of hydrogen, amino, quaternary amino, aldehyde, aryl, hydroxyl, phosphoryl, sulfhydryl, water solubilizing groups, alkyl groups of twenty-six carbons or less, lipid solubilizing groups, hydrocarbon solubilizing groups, groups promoting solubility in polar solvents, groups promoting solubility in nonpolar solvents, and -E-F; and further providing that any of R1, R2, R3, R4, R5, R6, or R7 may be substituted with halo, nitro, cyan, —CO$_2$alkyl, —CO$_2$H, —CO$_2$aryl, NO$_2$, or alkoxy wherein:

F is selected from the group consisting of hydroxy, protected hydroxy, alkoxy, sulfonate, sulfate, carboxylate, and lower alkyl substituted amino or quartenary amino;

E is spacer group of formula —(CH$_2$)n- wherein n is an integer from 0-5 inclusively;

Alternatively, E is a spacer group of formula —(CH$_2$—O—CH$_2$)$_n$— wherein n is an integer from 0-5, inclusively;

The following are more specific examples of reporter molecules according to structure IV, V and VI:

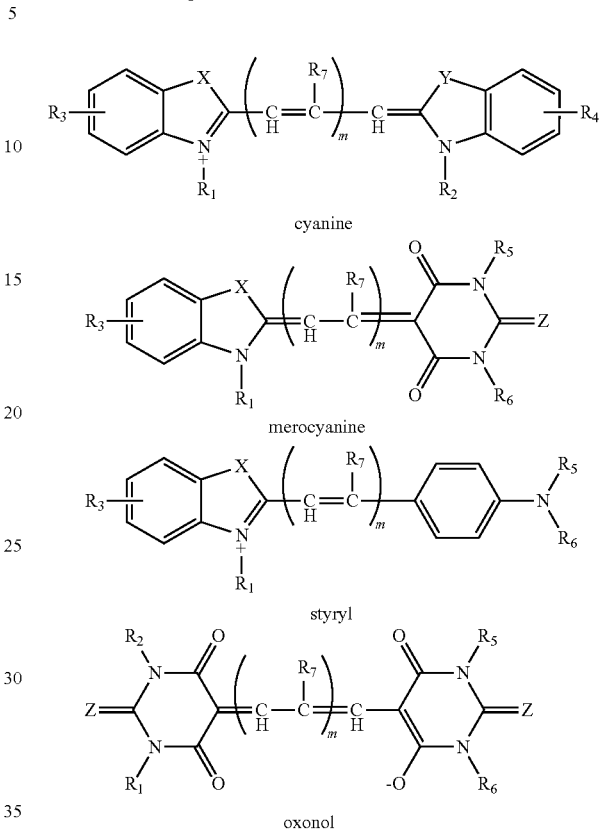

In these structures X and Y are selected from the group consisting of O, S and —CH(CH$_3$)$_2$—;

Z is selected from the group consisting of O and S; m is an integer selected from the group consisting of 0, 1, 2, 3 and 4 and, preferably an integer from 1-3. In the above formulas, the number of methine groups determines in part the excitation color.

The cyclic azine structures can also determine in part the excitation color. Often, higher values of m contribute to increased luminescence and absorbance. At values of m above 4, the compound becomes unstable. Thereupon, further luminescence can be imparted by modifications at the ring structures. When m=2, the excitation wavelength is about 650 nm and the compound is very fluorescent. Maximum emission wavelengths are generally 15-100 nm greater than maximum excitation wavelengths.

The polymethine chain of the luminescent dyes of this invention may also contain one or more cyclic chemical groups that form bridges between two or more of the carbon atoms of the polymethine chain. These bridges might serve to increase the chemical or photostability of the dye and might be used to alter the absorption and emission wavelength of the dye or change its extinction coefficient or quantum yield. Improved solubility properties may be obtained by this modification.

In various embodiments, the change of the acceptor dye upon interaction of the acceptor and the activator, and optionally the selectivity component with a target molecule, may include, for example, a shift in absorption wavelength, a shift in emission wavelength, a change in quantum yield, a change in polarization of the dye molecule, and/or a change in fluorescence intensity. The change can be two-fold, ten-fold, one hundred-fold, one thousand-fold or even higher. Any method suitable for detecting the spectral change associated with a given acceptor may be used, and suitable instruments for detection of a sensor dye spectral change, include, for example, fluorescent spectrometers, filter fluorometers, microarray readers, optical fiber sensor readers, epifluorescence microscopes, confocal laser scanning microscopes, two photon excitation microscopes, and flow cytometers.

The activator can be associated with a selectivity component. For example, the acceptor may be covalently attached to the selectivity component. The activator may be covalently attached to the selectivity component using standard techniques. For example, the activator may be directly attached to the selectivity component by forming a chemical bond between one or more reactive groups on the two molecules. For example, a thiol reactive group on the activator is attached to a cysteine residue (or other thiol containing molecule) on the selectivity component. Alternatively, the activator may be attached to the selectivity component via an amino group on the selectivity component. In another embodiment, the activator and selectivity component are presented on a contiguous fusion protein. In other embodiments, the activator may be attached to the selectivity component via a linker group. Suitable linkers include, for example, chemical groups, an amino acid or chain of two or more amino acids, a nucleotide or chain of two or more polynucleotides, polymer chains, and polysaccharides. In one example, the activator is attached to the selectivity component using a linker having a maleimide moiety. Linkers may be homofunctional (containing reactive groups of the same type), heterofunctional (containing different reactive groups), or photoreactive (containing groups that become reactive on illumination). A variety of photoreactive groups are known, for example, groups in the nitrene family.

One or more activators may be attached at one or more locations on the selectivity component. For example, two or more molecules of the same activator may be attached at different locations on a single selectivity component molecule. Alternatively, two or more different activators may be attached at different locations on a single selectivity component molecule. For example, 2, 3, 4, 5, 6, 7, 8, 9, 10 or more activators are attached at different sites on the selectivity component. The one or more activators may be attached to the selectivity component so as to maintain the activity of the activators and the selectivity component.

In certain embodiments, the activator further comprises a moiety that is specific for the selectivity component. For example, the activator may be linked to a substrate, a hapten, an antibody fragment or other binding reagent, etc. that is specific for the selectivity component. The activator may be covalently attached to the moiety using standard techniques. In certain embodiments the activator may be directly attached to the moiety by forming a chemical bond between one or more reactive groups on the two molecules. In other embodiments, the activator may be attached to the moiety via a linker group. Suitable linkers include, for example, chemical groups, an amino acid or chain of two or more amino acids, a nucleotide or chain of two or more polynucleotides, polymer chains, and polysaccharides. Linkers may be homofunctional (containing reactive groups of the same type), heterofunctional (containing different reactive groups), or photoreactive (containing groups that become reactive on illumination).

The donor and acceptor are connected by a linker that typically has at least three branches, at least two for the two or more donors and at least one for the acceptor. The linker can be a low polydispersity or monodisperse (PD=1) dendron, or a branched or star group or polymer. Star polymers can be prepared by standard polymerization methods, including free-radical methods and, preferably, for low polydispersity, a living radical polymerization method, such as Atom Transfer Radical Polymerization (ATRP). It is preferred in many instances that the linking group is a dendron with a defined architecture for many reasons, including efficient activation of the acceptor and consistency in product function. In one embodiment, the linking group is a dendron, such as a PAMAM, polyethyleneimine (PEI) and polyproyleneimine (PPI) dendrons. Other dendrons include Newkome dendrons, 2,2-bis(methylol)propionic acid (bis-MPA) and polyphenylene dendrons. Many dendrons are available commercially and their synthesis chemistries are well-characterized. Dendrons can be prepared by "click chemistry," involving repeated addition of small units. Dendrons can be constructed divergently—from the inside out, or convergently—from the outside in.

For PAMAM dendrons, for example, ammonia or ethylene diamine is used as the core molecule. In the presence of methanol it reacts with methyl acrylate and then ethylenediamine is added:

$$NH_3 + 3CH_2CHCOOCH_3 \rightarrow N(CH_2CH_2COOCH_3)_3 \qquad (1)$$

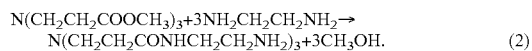
$$N(CH_2CH_2COOCH_3)_3 + 3NH_2CH_2CH_2NH_2 \rightarrow \\ N(CH_2CH_2CONHCH_2CH_2NH_2)_3 + 3CH_3OH. \qquad (2)$$

At the end of each branch there is a free amino group that can react with two methyl acrylate monomers and two ethylenediamine molecules. Each complete reaction sequence results in a new dendron generation. The half-generation PAMAM dendrons (e.g., 0.5, 1.5, 2.5) possess anionic surfaces of carboxylate groups. The number of reactive surface sites is doubled with every generation. For poly(propylene imine) dendrons, for example, butylenediamine (BDA) can be used as the core molecule. The repetitive reaction sequence involves Michael addition of acrylonitrile to a primary amino group followed by hydrogenation of nitrile groups to primary amino groups (see, e.g., Klajnert, B. et al., Dendrimers: Properties and Applications, *Acta Biochimica Polonica*, (2001) 48(1):199-208).

PAMAM dendrons may be synthesized as shown below. Dendronic material formed from PAMAM are commercially available from Sigma-Aldrich, St. Louis, Mo. (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups). Dendronic material formed from polypropylenimine is commercially available under the trade designation "DAB-AM" from Aldrich Chemical. For example, DAB-Am-4 is a generation 1 polypropylenimine tetraamine dendron with 4 primary amino groups, DAB-Am-8 is a generation 2 polypropylenimine octaamine dendron with 8 primary amino groups, DAB-Am-16 is a generation 3 polypropylenimine hexadecaamine with 16 primary amino groups, DAB-Am-32 is a generation 4 polypropylenimine dotriacontaamine dendron with 32 primary amino groups, and DAB-Am-64 is a generation 5 polypropylenimine tetrahexacontaamine dendron with 64 primary amino groups. Dendronic material formed from 2,2-Bis(hydroxyl-methyl)propionic acid (MPA) also is available from Sigma Aldrich. Other commercial sources include Dendritic Nanotechnologies, Inc. of Mount Pleasant, Mich., Dendritech, Inc. of Midland, Mich., and Polymer Factory of Nacka, Sweden, among others.

In one example, dendrons useful in dyedron synthesis comprise a cleavable core, such that the dendron can be cleaved into separate parts (e.g., halves). An example of such a dendron is a cysteamine-core PAMAM dendrimer. In one example, the periphery of the resultant dendron comprises two or more active groups to which donors can be attached and the "head" comprises a different active group to which an acceptor can be attached. This allows for the discrete functionality and facile preparation of the dyedrons comprising two or more donors linked to a single acceptor.

The activator component of the dyedron system described herein is a binding reagent, binding partner, ligand, FAP, or the like that interacts in any manner with the acceptor, such as by binding the acceptor, to cause the acceptor to become fluorescent, become increasingly fluorescent and/or shift its emission spectrum in response to illumination within the absorption spectrum of the dyedron (typically the absorbance spectrum of the donors). Optimally, absent binding of the activator to the acceptor, the acceptor will not fluoresce, or fluoresce insubstantially at a detection wavelength. The acceptor may fluoresce at another wavelength, but should not fluoresce in a manner that interferes with, or interferes substantially with, detection of fluorescence at the detection wavelength. It should be recognized that there may be low-level fluorescence in the absence of binding of the acceptor by the activator, but that background fluorescence should be significantly less than the level of fluorescence obtained when the acceptor is bound by the activator. Preferably, the "gain" in fluorescence of activator-bound dyedron to non-activator-bound dydrimer is at least 100-fold, 1000-fold, 10,000-fold, or even greater. In an optimal embodiment, the acceptor will not fluoresce unless bound by the activator, or, as is more likely in the real world, will not substantially fluoresce unless bound by the activator. In practical use, there will be a certain level of background fluorescence, though it is preferably insubstantial.

As described in the examples herein, one non-limiting embodiment of the activator is an FAP (fluorogen activating peptide), a peptide produced by any useful means that binds to the fluorogen and/or the dyedron compound so as to increase the fluorescence of the acceptor at a given stimulatory wavelength and intensity. As described in the examples, one embodiment of the FAP is an scFv fragment, obtained from a yeast cell surface display library, and which activates the acceptor so that it fluoresces. The use of a yeast display library, and identification of a specific clone that expresses an FAP, permits directed evolution of the specific clone to produce derivatives with more desirable activity in a given dyedron system. An example of that is described below in relation to parent scFV L5-MG and evolved derivatives FAPs L5-MG E52D, L5-MG L91S, and L5-MG E52D L91S.

As would be readily evident to those of ordinary skill in the art, there are a multitude of methods for generating suitable activators. As shown herein as proof of concept, selection and evolution using yeast display libraries is an effective mechanism for generating useful FAPs. It should be evident that activators can be peptides, but also can be other molecules, such as nucleic acids and derivatives thereof, such as aptamers. Molecular libraries, such as libraries of small molecules, natural molecules, synthetic molecules, etc, also can readily be screened for activation of the acceptor by simply exposing the dyedron to a compound and determining if the compound can effectively activate the dyedron as described herein. The dyedron may be screened against libraries of random polypeptides, or libraries of binding agents, such as scFv fragments or other antibody fragments. Expression libraries of protein/peptide fragments or aptamers, expressed by bacteria, yeast, phage, etc. can be screened by colony fluorescence, fluorescence-activated cell sorting (FACS) or by affinity to surface-bound dyedron and subsequent amplification of retained phage, cells, etc. The growth, propagation, selection, and mutation of display/expression libraries is well known. Many commercial display/expression libraries are available and use thereof are well within the skill of the ordinary artisan.

International Patent Application Publication No. WO 2008/092041, incorporated herein by reference in its entirety, describes in detail not only the preparation of the L5-MG FAP, but a large number of other methods by which activators (selectivity component as described in that publication) are selected, evaluated and used. In that reference, a yeast cell surface display library of recombinant human scFvs, obtained from Pacific Northwest National Laboratory was obtained and clones were initially sorted by one or more rounds of FACS, isolating cells that activate a desired fluorogen. Later, the FACS-screened cells were further enriched by affinity selection or further cell sorting.

The activator may be any molecule which is capable of selectively interacting with the acceptor to cause the acceptor/dyedron to fluoresce or increase fluorescence. Non-limiting examples of the activator include: polypeptides, nucleic acids (such as oligonucleotides, cDNA molecules or genomic DNA fragments), carbohydrates, or other suitable organic or inorganic molecules.

The activator also may comprise or be attached to a selectivity component that binds, interacts with, or duplicates one or more components of a cell or organism. Non-limiting examples of selectivity components include: a protein or polypeptide, an antibody or other binding agent, and aptamer, a ligand, an agonist or antagonist, a metabolite or chemical moiety, a nucleic acid, such as DNA, RNA, etc., a cell, a microorganism (such as bacteria, fungi and viruses), a hormone, a receptor, a cytokine, a drug molecule, a carbohydrate, a pesticide, a dye, an amino acid, a small organic or inorganic molecules, or a lipid. Exemplary target molecules for the selectivity component include, for example, molecules involved in tissue differentiation and/or growth, cellular communication, cell division, cell motility, and other cellular functions that take place within or between cells, including regulatory molecules such as growth factors, cytokines, morphogenetic factors, neurotransmitters, and the like. In certain embodiments, target molecules may be bone morphogenic protein, insulin-like growth factor (IGF), and/or members of the hedgehog and Wnt polypeptide families. Other examples of selectivity components include: pathway and network proteins (for example, enzymes such as kinases or phosphatases), antibody fragments, non-antibody receptor molecules, aptamers, template imprinted materials, and organic or inorganic binding elements. Selectivity components having limited crossreactivity are generally preferred.

The activator and selectivity component may be part of a bifunctional compound, such as a fusion (chimeric) protein, or a combination of mono-functional components, such as a cross-linked composition in which an activator is linked by a linking group to a selectivity component. The activator and selectivity component may be similar chemical entities, as in the case of a bifunctional chimeric protein, two linked scFv fragments or an scFv activator linked to a protein, antibody or other polypeptide. They also may be different chemical entities, as in the case of the activator being a polypeptide, such as an scFv fragment, and the selectivity component is a nucleic acid, such as an aptamer, a template imprinted material, a metabolite, a lipid, a polysaccharide, a virion, etc.

In certain embodiments, the activator and/or the selectivity component are an antibody or an antibody fragment. For example, activators may be monoclonal antibodies, or derivatives or analogs thereof, including without limitation: Fv fragments, single chain Fv (scFv) fragments, Fab' fragments, F(ab')$_2$ fragments, single domain antibodies, camelized antibodies and antibody fragments, humanized antibodies and antibody fragments, and multivalent versions of the foregoing; multivalent activators including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule.

In one embodiment, the activator and/or the selectivity component is an antibody. Preparation of antibodies may be accomplished by any number of well-known methods for generating monoclonal antibodies. These methods typically include the step of immunization of animals, typically mice; with a desired immunogen (e.g., a desired target molecule—or fragment thereof). Once the mice have been immunized, and preferably boosted one or more times with the desired immunogen(s), monoclonal antibody-producing hybridomas may be prepared and screened according to well known methods (see, for example, Kuby, Janis, IMMUNOLOGY, Third Edition, pp. 131-139, W.H. Freeman & Co. (1997), for a general overview of monoclonal antibody production).

Production of antibodies and other binding reagents have become extremely robust. In vitro methods that combine antibody recognition and phage display techniques allow one to amplify and select antibodies or other binding reagents with very specific binding capabilities. See, for example, Holt, L. J. et al., "The Use of Recombinant Antibodies in Proteomics," Current Opinion in Biotechnology 2000, 11:445-449, incorporated herein by reference. These methods typically are much less cumbersome than preparation of hybridomas by traditional monoclonal antibody preparation methods. Binding epitopes may range in size from small organic compounds such as bromo uridine and phosphotyrosine to oligopeptides on the order of 7-9 amino acids in length.

In another embodiment, the activator and/or the selectivity component may be an antibody fragment. Selection and preparation of antibody fragments may be accomplished by any number of well-known methods. Phage display, bacterial display, yeast display, mRNA display and ribosomal display methodologies may be utilizes to identify and dome desired technology may be used to generate antibody fragment activators that are specific for a desired target molecule, including, for example, Fab fragments, F$_V$s with an engineered intermolecular disulfide bond to stabilize the V$_H$-VL pair, scFvs, or diabody fragments.

In certain embodiments, the activator comprises a polypeptide sequence having at least about 85%, at least about 90%, at least about 95%, about 96%, about 97%, about 98%, about 99% or about 100% sequence identity to any of the polypeptide sequences of SEQ ID NOS: 3-9 (FIGS. 12A and 12B). Vectors to produce the activator may be prepared as described below and in WO 08/092,041, with the nucleic acid encoding the polypeptide of SEQ ID NO: 3 or other activator sequences (SEQ ID NOS: 4-9), inserted in frame between flanking HA and c-myc epitopes of the pPNL6 plasmid and its homologs (for example, SEQ ID NO: 2 in FIG. 4), and used to transfect host cells as described herein and in WO 08/092,041.

Production of scFv antibody fragments using display methods, including phage, bacterial, yeast, ribosomal and mRNA display methods can be employed to produce the activator and/or selectivity component, as described herein. As described below, yeast display methods were used to produce an activator described below. Yeast display methods are described, for example, in Boder, et al. (2000) Proc. Natl. Acad. Sci. USA 97:10701-5; Swers, et al. (2004) Nucl. Acids. Res. 32:e36; and Yeast Display scFv Antibody Library User's Manual, Pacific Northwest National Laboratory, Richland, Wash. 99352, Revision Date: MF031112.

Ribosome display also is a useful method for producing the activator and/or the selectivity component. Ribosome display is a technique used to perform in vitro protein evolution to create proteins that can bind to a desired ligand. The process results in translated proteins that are associated with their mRNA progenitor which is used, as a complex, to bind to an immobilized ligand in a selection step. The mRNA encodes random polypeptides, and the diversity can far exceed that of phage and yeast display systems. The mRNA-protein hybrids that bind well to a ligand are then reverse transcribed to cDNA and their sequence amplified via PCR. The end result is a nucleotide sequence that can be used to create tightly binding proteins. (see, e.g., Hanes J, Plückthun A (1997) *Proc Natl Acad Sci USA* 91:4937-4942; He M, Taussig M J (1997) *Nucleic Acids Res* 25:5132-5134; and In Vitro Protein Expression Guide, PROMEGA (2005), pp-29-33, Chapter 6, Ribosome Display))

Ribosome display either begins with a DNA sequence or naive library of sequences coding for a specific protein. The sequence is transcribed, and then translated in vitro into protein. However, the DNA library coding for a particular library of binding proteins is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. What results is a complex of mRNA, ribosome, and protein which can bind to surface-bound ligand. This complex is stabilized with the lowering of temperature and the addition of cations such as $Mg^{2+}$.

During the subsequent binding, or panning, stages, the ribosome complex is introduced to surface-bound ligand. This can be accomplished several ways, for example using an affinity chromatography column with a resin bed containing ligand, a 96-well plate with immobilized surface-bound ligand, or magnetic beads that have been coated with ligand. The complexes that bind well are immobilized. Subsequent elution of the binders via high salt concentrations, chelating agents, or mobile ligands which complex with the binding motif of the protein allow dissociation of the mRNA. The mRNA can then be reverse transcribed back into cDNA, undergo mutagenesis, and iteratively fed into the process with greater selective pressure to isolate even better binders.

As it is performed entirely in vitro, there are two main advantages of ribosomal display methods over other selection technologies. First, the diversity of the library is not limited by the transformation efficiency of bacterial cells, but only by the number of ribosomes and different mRNA molecules present in the test tube. Second, random mutations can be introduced easily after each selection round, as no library must be transformed after any diversification step. This allows facile directed evolution of binding proteins over several generations.

In certain display methods, such as phage and yeast display, a library of V$_H$ and V$_L$ chains are prepared from mRNA of B-cells either naïve or immunized animals (such as a mouse, rabbit, goat or other animal), or even from polyclonal or monoclonal hybridoma. The mRNA is reverse-transcribed by known methods using either a polyA primer or murine immunoglobulin-specific primer(s), typically specific to sequences adjacent to the desired V$_H$ and V$_L$ chains, to yield cDNA. The desired V$_H$ and V$_L$ chains are amplified by polymerase chain reaction (PCR) typically using $V_H$ and $V_L$ specific primer sets, and are ligated together, separated by a linker $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In display vectors, the $V_H$-linker-$V_L$ sequence is cloned into a surface protein (e.g., for M13, the surface proteins g3p (pHI) or g8p, most typically g3p). Display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacteria cells is the Recombinant Phage Antibody System (RPAS), commercially available from GE Healthcare, Piscataway, N.J., and the pSKAN Phagemid Display System, commercially available from MoBiTec (Boca Scientific, Boca Raton, Fla.). Phage display systems, their construction and screening methods are described in detail in, among others, U.S. Pat. Nos. 5,702,892, 5,750,373, 5,821,047 and 6,127,132, each of which are incorporated herein by reference in their entirety.

Typically, once a population of clones, such as phage, yeast, bacteria, ribosomes, etc., are produced that display a desired polypeptide, such as an antibody fragment, epitope specific clones are selected by their affinity for the desired immunogen and, optionally, their lack be used for physically separating immunogen-binding clones from non-binding clones. Typically the immunogen is fixed to a surface and the clones are contacted with the surface. Non-binding clones are washed away while binding clones remain bound. Bound clones are eluted and propogated to amplify the selected clones. A number of iterative rounds of affinity selection typically are used, often increasingly higher stringency washes, to amplify immunogen binding clones of increasing affinity. Negative selection techniques also may be used to select for lack of binding to a desired target. In that case, un-bound (washed) clones are amplified. In the context of the present invention, fluorescence of bound dyedron can be used as a selectable marker for identifying clones. High throughput methods, such as FACS, may initially be employed to select clones, followed, optionally by detection of fluorescence in plated colonies by fluorescent imaging techniques.

Although it is preferred to use spleen cells and/or B-lymphocytes from animals preimmunized with a desired immunogen as a source of cDNA from which the sequences of the $V_H$ and $V_L$ chains are amplified by RT-PCR, naive (un-immunized with the target immunogen) splenocytes and/or B-cells may be used as a source of cDNA to produce a polyclonal set of VH and $V_L$ chains that are selected in vitro by affinity, typically by the above-described phage display (phagemid) method. When naive B-cells are used, during affinity selection, the washing of the first selection step typically is of very high stringency so as to avoid loss of any single clone that may be present in very low copy number in the polyclonal phage library. By this naive method, B-cells may be obtained from any polyclonal source, B-cell or splenocyte cDNA libraries also are a source of cDNA from which the VH and $V_L$ chains may be amplified. For example, suitable murine and human B-cell, lymphocyte and splenocyte cDNA libraries are commercially available from Agilent Technologies/Stratagene and from Invitrogen. Phagemid antibody libraries and related screening services are provided commercially by MorphoSys USA, Inc., of Charlotte, N.C. (CysDisplay).

The activator and/or the selectivity component do not have to originate from biological sources, such as from naive or immunized immune cells of animals or humans. The activator and/or the selectivity component may be screened from a combinatorial library of synthetic peptides. One such method is described in U.S. Pat. No. 5,948,635, incorporated herein by reference, which described the production of phagemid libraries having random amino acid insertions in the pill gene of M13. These phage may be clonally amplified by affinity selection as described above.

Panning in a culture dish or flask is one way to physically separate binding clones from non-binding clones Panning may be carried out in 96 well plates in which desired immunogen structures have been immobilized. Functionalized 96 well plates, typically used as ELISA plates, may be purchased from Pierce of Rockwell, Ill. Dyedron may be synthesized directly on $NH_2$ or COOH functionalized plates in an N-terminal to C-terminal direction. Other affinity methods for isolating clones having a desired specificity include affixing dyedron to beads. The beads may be placed in a column and clones may be bound to the column, washed and eluted according to standard procedures. Alternatively, the beads may be magnetic so as to permit magnetic separation of the binding particles from the non-binding particles. The immunogen also may be affixed to a porous membrane or matrix, permitting easy washing and elution of the binding clones.

In certain embodiments, it may be desirable to increase the specificity of the activator for a given target molecule or reporter molecule using a negative selection step in the affinity selection process. For example, activator-displaying clones may be contacted with a surface functionalized with dyedrons or fluorogens distinct from the target molecule or reporter molecule. Clones are washed from the surface and non-binding clones are grown to clonally expand the population of non-binding clones thereby deselecting clones that are not specific for the desired target molecule. In certain embodiments, random synthetic peptides may be used in the negative selection step. In other embodiments, one or more immunogens having structural similarity to the acceptor or donors may be used in the negative selection step.

Screening of activators will best be accomplished by high throughput parallel selection, as described in Holt et al. Alternatively, high throughput parallel selection may be conducted by commercial entities, such as by MorphoSys USA, Inc.

In certain embodiments, it may be desirable to mutate the binding region of the activator and/or selectivity component and select for activators and/or selectivity components with superior binding characteristics as compared to the un-mutated activator. This may be accomplished by any standard mutagenesis technique, such as by PCR with Taq polymerase under conditions that cause errors. In such a case, the PCR: primers could be used to amplify scFv- or binding reagent-encoding sequences of (e.g.) phagemid plasmids under conditions that would cause mutations. The PCR product may then be cloned into a (e.g.) phagemid vector and screened for the desired specificity, as described above.

In other embodiments, the activators and/or selectivity components may be modified to make them more resistant to cleavage by proteases. For example, the stability of the activators of the present invention that comprise polypeptides may be increased by substituting one or more of the naturally occurring amino acids in the (L) configuration with D-amino acids. In various embodiments, at least 1%, 5%, 10%, 20%, 50%, 80%, 90% or 100% of the amino acid residues of the activators may be of the D configuration. The switch from L to D amino acids neutralizes the digestion capabilities of many of the ubiquitous peptidases found in the digestive tract. Alternatively, enhanced stability of the activators of the invention may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of the activators may be achieved by intercalating one or more dextrorotatory amino acids (such as, dextrorotatory phenylalanine or dextrorotatory tryptophan) between the amino acids of the activator, hi exemplary embodiments, such modifications increase the protease resistance of the activators without affecting their activity or specificity of interaction with a desired target molecule or reporter molecule.

In certain embodiments, the antibodies or variants thereof, may be modified to make them less immunogenic if and when administered to a subject. For example, if the subject is human, the antibody may be "humanized"; where the complimentarity determining region(s) of the hybridoma-derived antibody has been transplanted into a human monoclonal antibody, for example as described in U.S. Pat. No. 6,407, 213. Also, transgenic mice, or other mammals, may be used to express humanized antibodies. Such humanization may be partial or complete.

In another embodiment, the activator is a Fab fragment. Fab antibody fragments may be obtained by proteolysis of an immunoglobulin molecule using the protease papain. Papain digestion yields two identical antigen-binding fragments, termed "Fab fragments", each with a single antigen-binding site, and a residual "Fc fragment". In still another embodiment, the activator is a F(ab')2 fragment. F(ab')$_2$ antibody fragments may be prepared from IgG molecules using limited proteolysis with the enzyme pepsin. In other embodiments, the selectivity component may be a network or pathway protein such as an enzyme, for example, a phosphatase or kinase. Such proteins may be mutated to create a binding site for a reporter and/or target molecule. For example, a method of creating a selectivity component biosensor from network and pathway proteins in cells and tissues may comprise mutating a specific region on a selected protein to create an activator portion for activat binding site for a reporter or target molecule. The region selected for mutation may be randomly or partially randomly mutated by creating mutations in selected regions of the gene that codes for the protein that is to be converted into a activator. The gene with the mutated region(s) may be incorporated by transfection into a system capable of expressing the protein in a way that allows reporter molecule (or target molecule) binding and fluorescence sensitivity to the activity (if a reporter molecule) to be assayed. For example, the DNA with the mutated region may be training the acceptor of the dyedron (see, e.g., Boder, et al. (2000) Proc. Natl. Acad. Sci USA 97:10701-5 and Swers, et al. (2004) Nucl. Acids. Res. 32:e36). By isolating and identifying by selection methods the genetic sequence of the particular protein within the mutated population that functions optimally as an activator and a selectivity component. In other embodiments, a library of mutants is generated from a degenerate oligonucleotide sequence. There are many ways by which the library may be generated from a degenerate oligonucleotide sequence. Chemical synthesis of a degenerate gene sequence may be carried out in an automatic DNA synthesizer, and the synthetic genes may then be ligated into an appropriate vector for expression. One purpose of a degenerate set of genes is to provide, in one mixture, all of the sequences encoding the desired set of potential protein sequences. The synthesis of degenerate oligonucleotides is well known in the art (see for example, Narang, S A (1983) Tetrahedron 39:3: Itakura et al., (1981) Recombinant DNA. Proc. 3rd Cleveland Sympos. Macromolecules, ed. AG Walton, Amsterdam: Elsevier pp. 273-289; Itakura et al., (1984) Annu. Rev. Biochem 53:323; Itakura et al., (1984) Science 198:1056; Ike et al. (1983) Nucleic Acid Res. 11:477). Such techniques have been employed in the directed evolution of other proteins (see, for example, Scott et al., (1990) Science 249:386-390; Roberts et al., (1992) Proc. Natl. Acad. Sci. USA 89:2429-2433; Devlin et al., (1990) Science 249: 404-406; Cwirla et al., (1990) Proc. Natl. Acad. Sci. USA 87: 6378-6382; as well as U.S. Pat. Nos. 5,223,409, 5,198,346, and 5,096,815).

Alternatively, other forms of mutagenesis may be utilized to generate a combinatorial library. For example, mutants may be generated and isolated from a library by screening using, for example, alanine scanning mutagenesis and the like, by linker scanning mutagenesis; by saturation mutagenesis; by PCR mutagenesis; or by random mutagenesis. Linker scanning mutagenesis, particularly in a combinatorial setting, is an attractive method for identifying activators.

In still other embodiments, the activator may be an aptamer, also known as a nucleic acid ligand. Aptamers are oligonucleotides that are selected to bind specifically to a desired molecular structure. Aptamers typically are the products of an affinity selection process similar to the affinity selection of phage display (also known as in vitro molecular evolution). The process involves performing several tandem iterations of affinity separation, e.g., using a solid support to which the desired immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids and phosphorothioate nucleic acids. Aptamers, may be prepared using the "SELEX" methodology which involves selection of nucleic acid ligands which interact with a target in a desirable manner combined with amplification of those selected nucleic acids. The SELEX process, is described in U.S. Pat. Nos. 5,475,096 and 5,270,163 and PCT Application No. WO 91/19813. These references, each specifically incorporated herein by reference, are collectively called the SELEX patents.

The SELEX process provides a class of products which are nucleic acid molecules, each having a unique sequence, and each of which has the property of binding specifically to a desired target compound or molecule. In various embodiments, target molecules may be, for example, proteins, carbohydrates, peptidoglycans or small molecules. SELEX methodology can also be used to target biological structures, such as cell surfaces or viruses, through specific interaction with a molecule that is an integral part of that biological structure.

The basic SELEX method has been modified to achieve a number of specific objectives. For example, U.S. Pat. No. 5,707,796 describes the use of the SELEX process in conjunction with gel electrophoresis to select nucleic acid molecules with specific structural characteristics, such as bent DNA. U.S. Pat. No. 5,580,737 describes a method for identifying highly specific nucleic acid ligands able to discriminate between closely related molecules, termed CounterSELEX. U.S. Pat. No. 5,567,588 describes a SELEX-based method which achieves highly efficient partitioning between oligonucleotides having high and low affinity for a target molecule. U.S. Pat. Nos. 5,496,938 and 5,683,867 describe methods for obtaining improved nucleic acid ligands after SELEX has been performed.

In certain embodiments, nucleic acid ligands as described herein may comprise modifications that increase their stability, including, for example, modifications that provide increased resistance to degradation by enzymes such as endonucleases and exonucleases, and/or modifications that enhance or mediate the delivery of the nucleic acid ligand (see, e.g., U.S. Pat. Nos. 5,660,985 and 5,637,459). Examples of such modifications include chemical substitutions at the ribose and/or phosphate and/or base positions, hi various embodiments, modifications of the nucleic acid ligands may include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil; backbone modifications, phosphorothioate or alkyl phosphate modifications, methylations, unusual base-pairing combinations such as the isobases isocytidine and isoguanidine and the like. Modifications may also include 3' and 5' modifications such as capping. In exemplary embodiments, the nucleic acid ligands are RNA molecules that are 2'-fluoro (2'-F) modified on the sugar moiety of pyrimidine residues.

The activators and/or selectivity component may be template imprinted material. Template imprinted materials are structures which have an outer sugar layer and an underlying plasma-deposited layer. The outer sugar layer contains indentations or imprints which are complementary in shape to a desired target molecule or template so as to allow specific interaction between the template imprinted structure and the target molecule to which it is complementary. Template imprinting can be utilized on the surface of a variety of structures, including, for example, medical prostheses (such as artificial heart valves, artificial limb joints, contact lenses and stents), microchips (preferably silicon-based microchips) and components of diagnostic equipment designed to detect specific microorganisms, such as viruses or bacteria. Template-imprinted materials are discussed in U.S. Pat. No. 6,131,580, which is hereby incorporated by reference in its entirety.

In certain embodiments, an activator may contain a tag or handle which facilitates its isolation, immobilization, identification, or detection and/or which increases its solubility. In various embodiments, the tag may be a polypeptide, a polynucleotide, a carbohydrate, a polymer, or a chemical moiety and combinations or variants thereof. In certain embodiments, exemplary chemical handles, include, for example, glutathione S-transferase (GST); protein A, protein G, calmodulin-binding peptide, thioredoxin, maltose binding protein, HA, myc, poly arginine, poly His, poly His-Asp or FLAG tags. Additional exemplary tags include polypeptides that alter protein localization in vivo, such as signal peptides, type III secretion system-targeting peptides, transcytosis domains, nuclear localization signals, etc.

In another embodiment, an activator and/or selectivity component may be modified so that its rate of traversing the cellular membrane is increased. For example, the activator may be attached to a peptide which promotes "transcytosis," e.g., uptake of a polypeptide by cells. The peptide may be a portion of the HIV transactivator (TAT) protein, such as the fragment corresponding to residues 37-62 or 48-60 of TAT, portions which have been observed to be rapidly taken up by a cell in vitro (Green and Loewenstein, (1989) Cell 55:1179-1188). Alternatively, the internalizing peptide may be derived from the *Drosophila* antennapedia protein, or homologs thereof. The 60 amino acid long homeodomain of the homeoprotein antennapedia has been demonstrated to translocate through biological membranes and can facilitate the translocation of heterologous polypeptides to which it-is coupled. Thus, activators may be fused to a peptide consisting of about amino acids 42-58 of *Drosophila* antennapedia or shorter fragments for transcytosis (Derossi et al. (1996) and J Biol Chem 271:18188-18193). The transcytosis polypeptide may also be a non-naturally-occurring membrane-translocating sequence (MTS), such as the peptide sequences disclosed in U.S. Pat. No. 6,248,558.

In still other embodiments, the activator/selectivity component is bivalent, comprising both the activator and selectivity component in one contiguous polypeptide sequence in the form of a fusion (chimeric) protein comprising any suitable polypeptide activator and selectivity component. As above, the fusion protein may comprise at least one domain which increases its solubility and/or facilitates its purification, identification, detection, targeting and/or delivery. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, and targeting moieties, i.e. proteins specific for a target molecule, etc. In various embodiments, a polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. Linker sequences between an activator and/or selectivity component polypeptide may be included in order to facilitate construction of the fusion protein or to optimize protein expression or structural constraints of the fusion protein. Exemplary, proof of concept fusion proteins are described below.

In other embodiments, the activators and selectivity component is expressed within the cell or organism or subject to be analyzed as a fusion protein (see the examples below). The expression methods described below may also be used to express an activator and selectivity component in a host cell that is then isolated and purified for use as described herein and as is know to those of ordinary skill in the relevant arts.

Generally, a nucleic acid encoding activators and selectivity component can be introduced into a host cell, such as by transfection or infection, and the host cell is cultured under conditions allowing expression of the activator. Methods of introducing nucleic acids into prokaryotic and eukaryotic cells are well known in the art. Suitable media for mammalian and prokaryotic host cell culture are well known in the art. In some instances, the nucleic acid encoding the subject polypeptide is under the control of an inducible promoter, which is induced once the host cells comprising the nucleic acid have divided a certain number of times. For example, where a nucleic acid is under the control of a beta-galactose operator and repressor, isopropyl beta-D-thiogalactopyranoside (IPTG) is added to the culture when the bacterial host cells have attained a density of about $OD_{600}$ 0.45-0.60. The culture is then grown for some more time to give the host cell the time to synthesize the polypeptide. Cultures are then typically frozen and may be stored frozen for some time, prior to isolation and purification of the polypeptide.

Thus, a nucleotide sequence encoding all or part of an activator and selectivity component may be used to produce a recombinant form of an activators and selectivity component via microbial or eukaryotic cellular processes. Ligating the sequence into a polynucleotide construct, such as an expression vector, and transforming, infecting, or transfecting into hosts, either eukaryotic (yeast, avian, insect or mammalian) or prokaryotic (bacterial cells), are standard procedures. Similar procedures, or modifications thereof, may be employed to prepare recombinant polypeptides by microbial means or tissue-culture technology in accord with the subject invention.

By "expression" it is meant the overall flow of information from a gene (without limitation, a functional genetic unit for producing a gene product, typically encoded on DNA or RNA, for some viruses, and comprising a transcriptional promoter, and other cis-acting elements, such as response elements and/or enhancers, an expressed sequence that typically encodes a protein (open-reading frame or ORF) or functional/structural RNA, and a polyadenylation sequence), to produce a gene product (typically a protein, optionally post-translationally modified or a functional/structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected of transduced into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene. All nucleotide sequences described herein are provided in a 5'-to-3' direction and all amino acid sequences described herein are provided in an N-terminal-to-C-terminal direction.

Other embodiments of nucleic acid sequences encoding the activator and selectivity component, as well as vectors, host cells, cultures thereof, and methods of making fusion proteins are described below or in WO 2008/092041. A nucleic acid encoding an activator and/or selectivity component can be operably linked to a bacterial promoter, e.g., the anaerobic *E. coli*, NirB promoter or the *E. coli* lipoprotein lip; *Salmonella* pagC promoter, *Shigella* ent promoter, the tet promoter on TnIO, or the ctx promoter of *Vibrio cholera*. Any other promoter can be used. The bacterial promoter can be a constitutive promoter or an inducible promoter. A signal peptide sequence may be added to the construct, such that the activator is secreted from cells. Such signal peptides are well known in the art. In one embodiment, the powerful phage T5 promoter, that is recognized by *E. coli* RNA polymerase is used together with a lac operator repression module to provide tightly regulated, high level expression or recombinant proteins in *E. coli*. In this system, protein expression is blocked in the presence of high levels of lac repressor. A huge variety of methods and genetic constructs are available commercially and are otherwise known by or available to those of ordinary skill in the art, for production of recombinant proteins and polypeptides. In vitro protein synthesis using, e.g., eukaryotic lysates, such as rabbit reticulocyte lysates, rabbit oocyte lysates, human cell lysates, insect cell lysates and wheat germ extracts or even synthetic methods, as are broadly known, can be employed to produce the polypeptides described herein.

Plant expression vectors can be used. For example, viral promoters such as the 35S RNA and 19S RNA promoters of CaMV, or the coat protein promoter of TMV may be used; alternatively, plant promoters such as the small subunit of RUBISCO; or heat shock promoters, e.g., soybean hsp 17.5-E or hsp 17.3-B may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, New York, Section VIII, pp. 421-463; and Grierson & Corey, 1988, Plant Molecular Biology, 2d Ed., Blackie, London, Ch. 7-9. Alternately, insect systems can be employed to produce the polypeptides described herein. In one such system, *Autographa californica* nuclear polyhedrosis virus (AcNPV) is used as a vector to express foreign genes. The virus grows in *Spodoptera frugiperda* cells. (see, e.g., Smith, U.S. Pat. No. 4,215,05). In another embodiment of an insect system, the DNA encoding the subject polypeptide is cloned into the pBlueBacIII recombinant transfer vector (Invitrogen, San Diego, Calif.) downstream of the polyhedrin promoter and transfected into Sf9 insect cells (derived from *Spodoptera frugiperda* ovarian cells, available from Invitrogen, San Diego, Calif.) to generate recombinant virus. In another embodiment, the subject polypeptides are prepared in transgenic animals, such that in certain embodiments, the polypeptide is secreted, e.g., in the milk of a female animal.

Viral vectors as are broadly known in the relevant arts, many of which are available commercially, may also be used for efficient in vitro introduction of a nucleic acid into a cell. Infection of cells with a viral vector has the advantage that a large proportion of the targeted cells can receive the nucleic acid. Additionally, polypeptides encoded by genetic material in the viral vector, e.g., by a nucleic acid contained in the viral vector, are expressed efficiently in cells that have taken up viral vector nucleic acid. Examples of useful viral vector systems include retrovirus, adenovirus and adeno-associated virus vectors are generally understood to be useful for the transfer of exogenous genes in vivo, particularly into mammals. These vectors provide efficient delivery of genes into cells, and the transferred nucleic acids typically are stably integrated into the chromosomal DNA of the host (see Miller, A. D. (1990) Blood 76:271).

Another viral gene delivery system utilizes adenovirus-derived vectors. Suitable adenoviral vectors derived from the adenovirus strain Ad type 5 d1324 or other strains of adenovirus (e.g., Ad2, Ad3, Ad7, etc.) are well known to those skilled in the art. Recombinant adenoviruses can be advantageous in certain circumstances in that they are capable of infecting non-dividing cells and can be used to infect a wide variety of cell types, including airway epithelium, endothelial cells, hepatocytes and muscle cells. Furthermore, the virus particle is relatively stable and amenable to purification and concentration, and, as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors. Most replication-defective adenoviral vectors currently in use and therefore favored by the present invention are deleted for all or parts of the viral E1 and E3 genes but retain as much as 80% of the adenoviral genetic material. Expression of the inserted genetic material can be under control of, for example, the E1A promoter, the major late promoter (MLP) and associated leader sequences, the E3 promoter, or exogenously added promoter sequences.

Yet another viral vector system useful for delivery of genetic material encoding the subject polypeptides is the adeno-associated virus (AAV). Adeno-associated virus is a naturally occurring defective virus that requires another virus, such as an adenovirus or a herpes virus, as a helper virus for efficient replication and a productive life cycle. It is also one of the few viruses that may integrate its DNA into non-dividing cells, and exhibits a high frequency of stable integration. Vectors comprising as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470 and Flotte et al. (1993) J. Biol. Chem. 268:3781-3790). Other viral vector systems may be derived from herpes virus, vaccinia virus, and several RNA viruses.

In addition to viral transfer methods, such as those illustrated above, non-viral methods can also be employed to cause expression of nucleic acids encoding the subject polypeptides, e.g. in a cell in vitro or in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of genetic material by the targeted cell. Exemplary gene delivery systems of this type include liposomal derived systems, polylysine conjugates, and artificial viral envelopes. For example, genetic material can be entrapped in liposomes bearing positive charges on their surface (e.g., lipofectins) and, optionally, which are tagged with antibodies against cell surface antigens of the target tissue (Mizuno et al. (1992) No Shinkei Geka 20:547-551; PCT publication WO91/06309; Japanese patent application 1047381; and European patent publication EP-A-43075). For example, lipofection of papilloma-infected cells can be carried out using liposomes tagged with monoclonal antibodies against PV-associated antigen (see Viae et al. (1978) J Invest Dermatol 70:263-266; see also Mizuno et al. (1992) Neurol. Med. Chir. 32:873-876).

The gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, genetic material encoding the subject chimeric polypeptides can be used to transfect hepatocytic cells in vivo using a soluble polynucleotide carrier comprising an asialoglycoprotein conjugated to a polycation, e.g., polylysine (see U.S. Pat. No. 5,166,320). It will also be appreciated that effective delivery of the nucleic acid constructs via mediated endocytosis can be improved using agents which enhance escape of the gene from the endosomal structures. For instance, whole adenovirus or fusogenic peptides of the influenza HA gene product can be used as part of the delivery system to induce efficient disruption of DNA-comprising endosomes (Mulligan et al. (1993) Science 260-926; Wagner et al. (1992) Proc. Natl. Acad. ScL USA 89:7934; and Christiano et al. (1993) Proc. Natl. Acad. Sci. USA 90:2122).

According to certain embodiments of the dyedrons described herein, certain functional goals are desirable.

In one example, the goal is to produce a donor array preparation with the following characteristics: >$10^6$ molar extinction (561 nm) and $\Phi_{array}/\Phi_{free}$=0.7. Standard monoreactive NHS ester donor dyes (e.g. Cy3, Cy3.5, Alexa568, Atto-565) are coupled to multiple variations of commercially available bifunctional dendrimers (e.g. PAMAM, cystamine core), and their steady state absorbance and fluorescence properties are determined. Molecular characterization by FCS, electrophoresis, and mass spectroscopy confirms degree of labeling and molecular dispersity, and allows selection of the donor arrays with the highest extinction and quantum yield. If quantum yields are dramatically quenched, steric modifications of the dyes (e.g. PEG modification) or alternative dendronic scaffolds with distinct charge, polarity, and spacing properties can be prepared to reduce inter-dye interactions.

In another example, the design goal is >90% transfer efficiency. Bright donor arrays are coupled to dark quenchers (e.g., DABCYL, 4-((4-(dimethylamino)phenyl)azo)benzoic acid]) and FRET (Förster resonance energy transfer or fluorescence resonance energy transfer) acceptors (e.g., Cy5, Alexa 700, Cy7) to optimize the quenching properties by variation of linker length and to determine if intermediate acceptors (that is, a second donor is provided that overlaps spectra both with a first donor and the acceptor, where the emission spectrum of the first donor does not (or does not necessarily) overlap with the absorption spectrum of the acceptor) are required for more red-shifted fluorogens. If necessary, heterobifunctional intermediate acceptor dyes (i.e. NHS ester and iodoacetate functionalities) can be prepared to facilitate testing of intermediate acceptors (Bielinska, A. U., J. F. KukowskaLatallo, and J. R. Baker. 1997. The interaction of plasmid DNA with polyamidoamine dendrimers: mechanism of complex formation and analysis of alterations induced in nuclease sensitivity and transcriptional activity of the complexed DNA. Bba-Gene Struct Expr 1353:180-190).

In another example, the design goal is a low fluorescence of the acceptor linked to the dendron when not bound to the FAP or donors. The acceptor fluorogen is attached to the dendron scaffold using chemistry appropriate to the dyedron synthesis, and the fluorescence of the construct is tested in cell extracts and purified nucleic acid materials for background fluorescence under the conditions that would be used to detect the dyedron in the presence of the multiple donors. If the fluorescence activation is high, modifications of the acceptor charge, size, and hydrophobicity can be utilized to decrease the nonspecific interactions in a cellular context.

In another example the design goal for the dyedron/FAP Preparation and Validation is three ~60 nm spectrally spaced dyedron/FAP modules with $\Phi_{on}/\Phi_{off}$>1000 in cell lysate. Malachite green can serve as the initial fluorogen, as we already have selected modules that activate it with switching ratios of >15,000 fold in buffer. Additional fluorogens may be designed and synthesized. Unsymmetric polymethine dyes, and analogs of indocyanine green may be used as fluorogens, as can many of the polarity sensing dyes (e.g. merocyanine and styryl dyes) with far-red and near IR emission. Fluorogens are screened for nonspecific activation in cell lysate before modifying donor arrays. Quenching and activation by selected FAP modules are characterized in buffer and cell lysate to determine the activation ratio. FAP/Dyedron pairs with acceptable switching ratios are characterized by FCS and TIRF-single molecule microscopy.

According to certain embodiments, novel fluorogen activating peptides are isolated using methods that were established for the initial selections of fluorogen activating peptides from the yeast surface display library. Briefly, biotinylated versions of each fluorogen that have been synthetically prepared will be incubated with an expanded, induced aliquot of the Pacific Northwest National Laboratory yeast surface displayed scFv library (~$10^9$ distinct clones, $10^{11}$ cells for selection). Yeast that bind to the biotinylated dye are magnetically enriched in two steps, first with streptavidin conjugated magnetic bead, followed by expansion and a second round of enrichment with anti-biotin conjugated magnetic beads. These yeast are eluted from the beads, and then incubated with free dye (if amenable to direct detection on the flow cytometer—if not, biotinylated dye followed by a wash and streptavidin Alexa 488 labeling), and flow sorted to select a population of cells that are fluorogenic or that bind to the fluorogen. Fluorogenic clones not detectable on the cytometer can be detected by washing dye over an agar plate containing isolated induced colonies, and selecting the brightest colonies using a wide-field fluorescence imaging system for subsequent analysis. It was found that clones recovered from the library have a range of affinities and spectral properties, and that subsequent affinity maturation (by error-prone PCR) can result in changes in affinity, quantum yield, and selectivity. Clones are easily transferred from the surface display system to a yeast secretion system using established protocols. Promising clones can be sequenced, and unique clones are transferred to the pPNL9 secretion vector to produce protein for subsequent characterization of the ensemble and single molecule fluorescence and binding properties with the fluorogen.

Figure 5A:
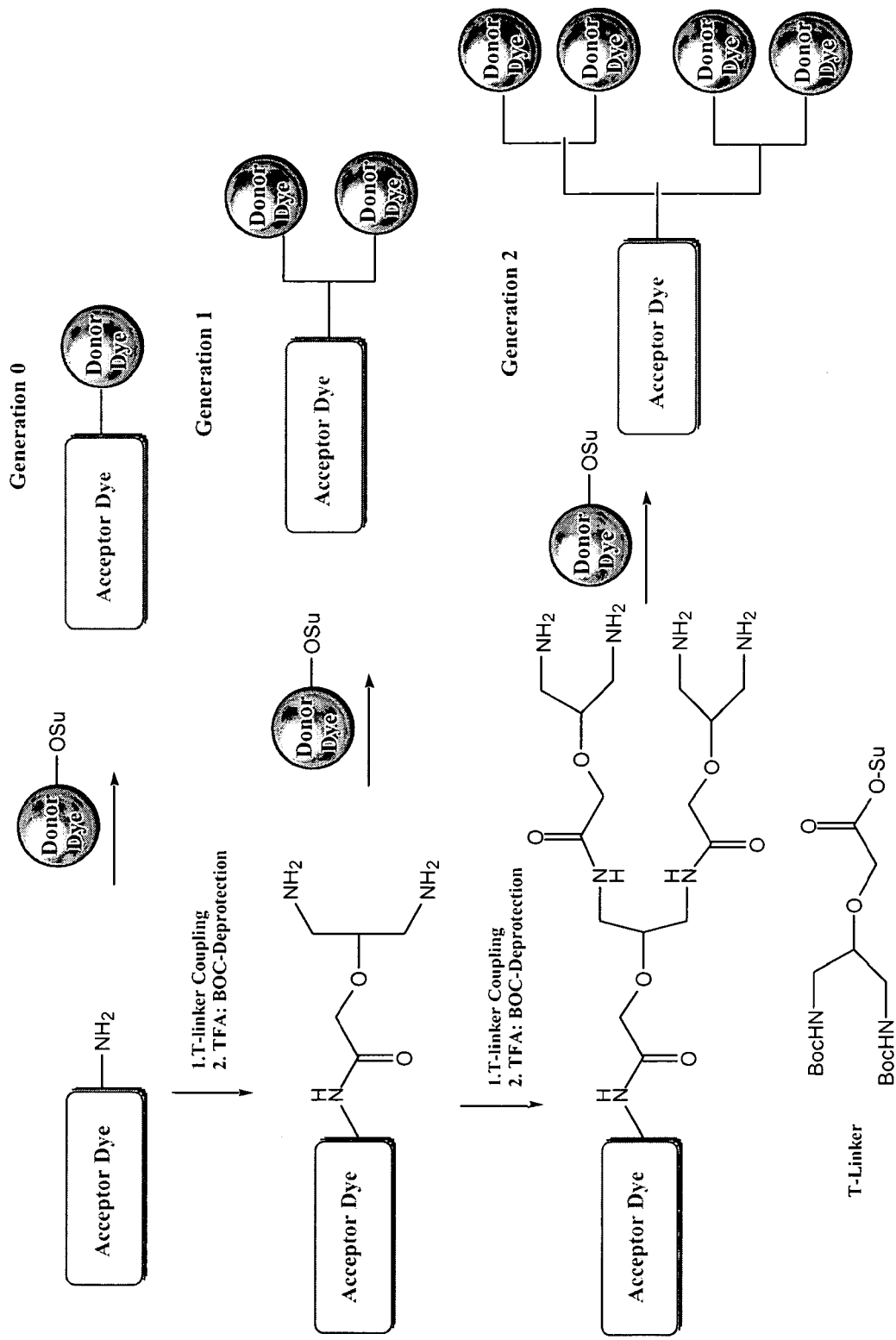
FIG. 5 shows dyedron synthesis based on a T-linker strategy (A) and a Tripod strategy (B) will provide synthetic routes for up to 9 donors linked to a single fluorogen quencher with a compact intramolecular spacing to ensure high FRET efficiency. For fluorogen-donor pairs with poorer spectral overlap a cascade design (C) with a mediator dye will enhance the FRET efficiency.
Figure 5B:
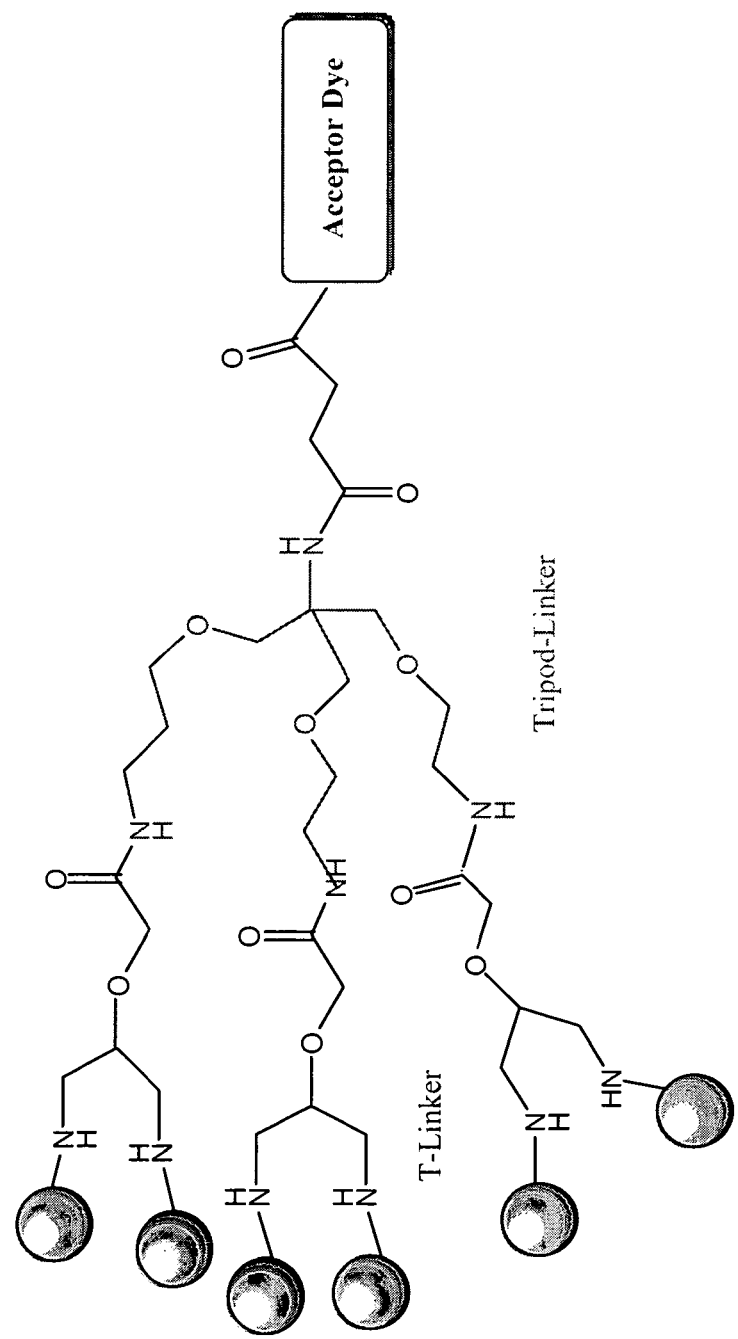
Figure 5C:
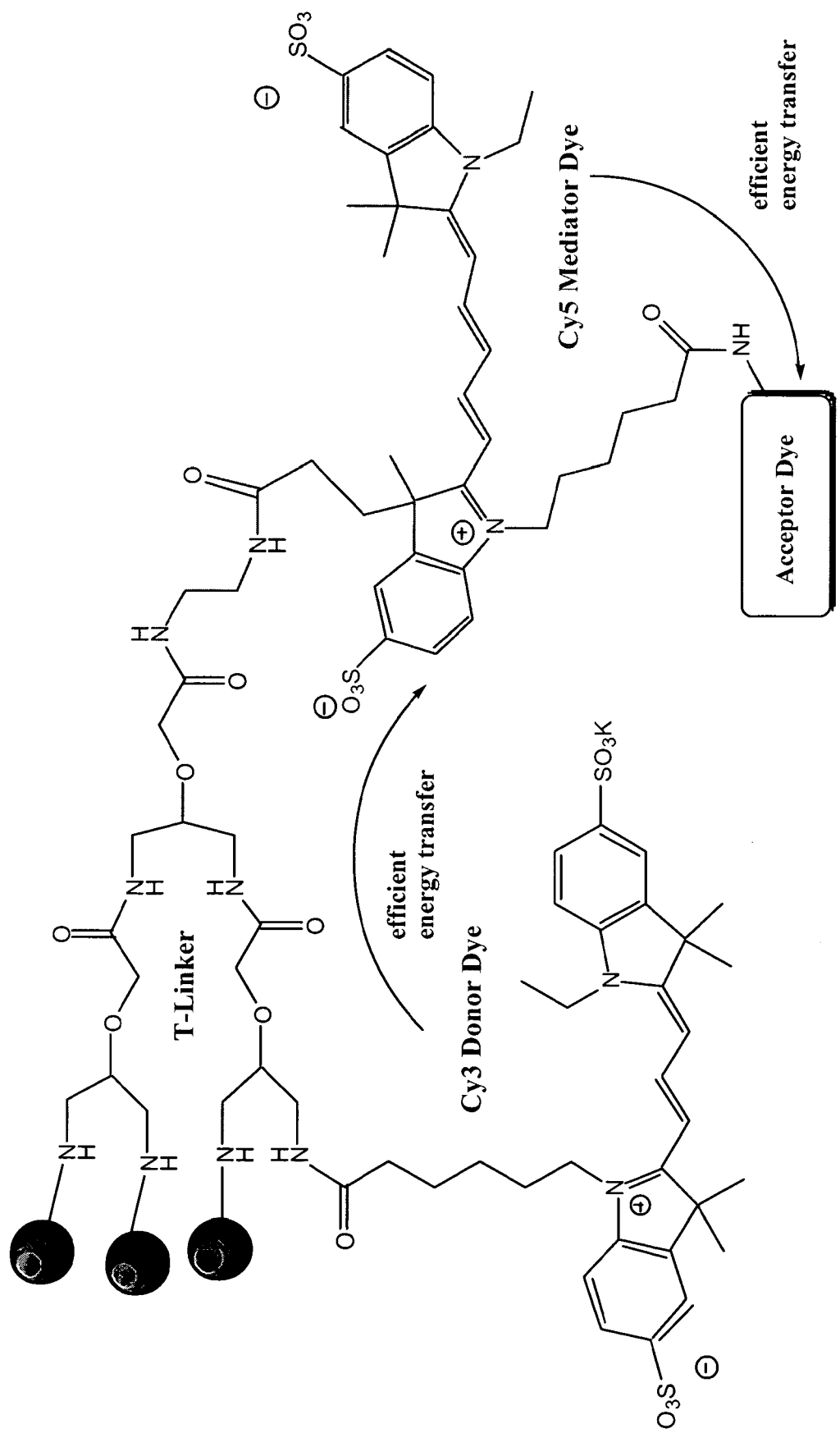
Figure 6A:
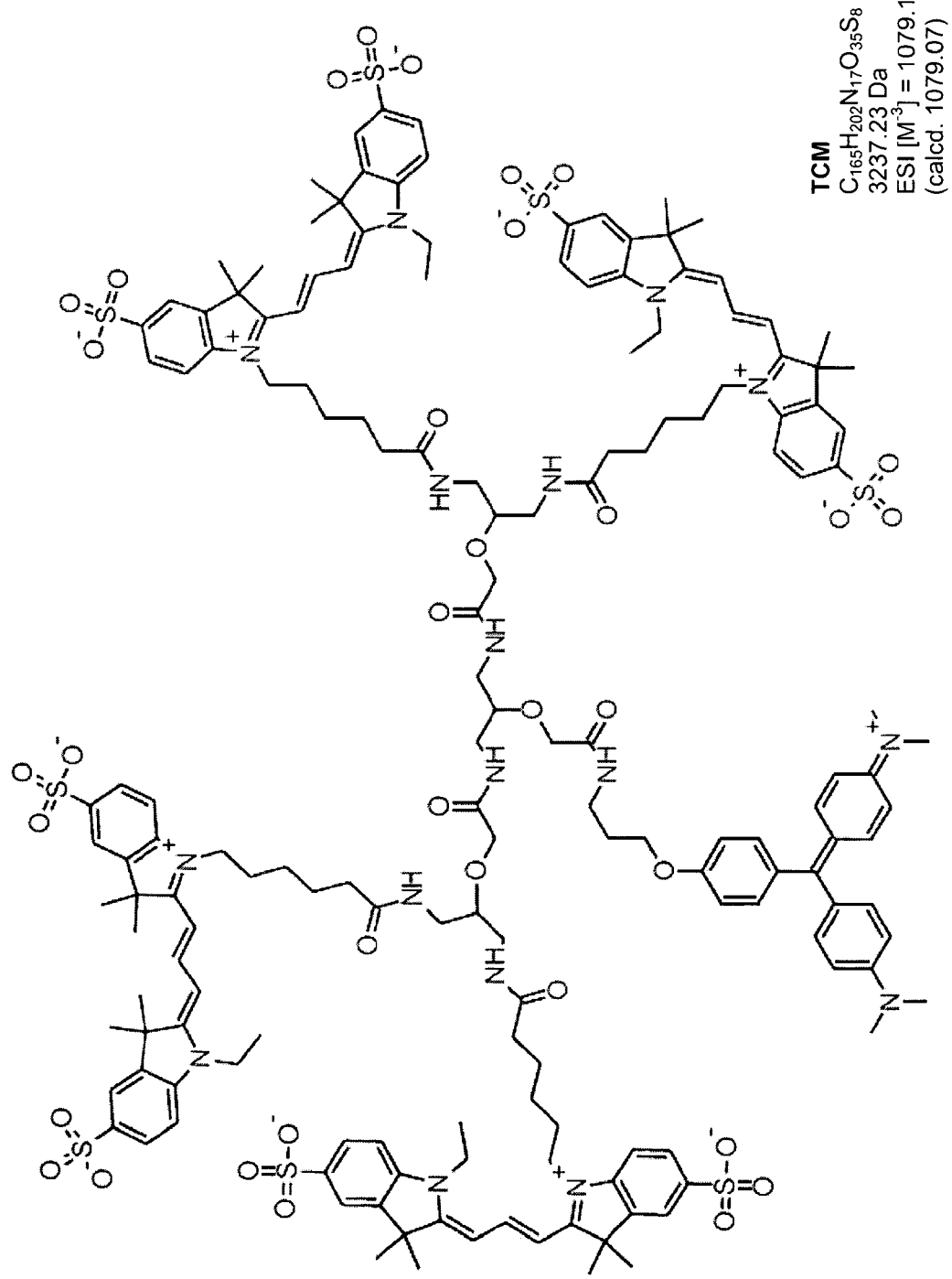
FIG. 6A-6D. Structure of dyedrons. Monoisotopic masses and confirmatory mass spectrometry ions are shown. TCM, Tetra-Cy3.29 malachite green; BCM, Bis-Cy3.29 malachite green; CM, Cy3.29 malachite green; M, malachite green diethyleneglycolamine.
Figure 6B:
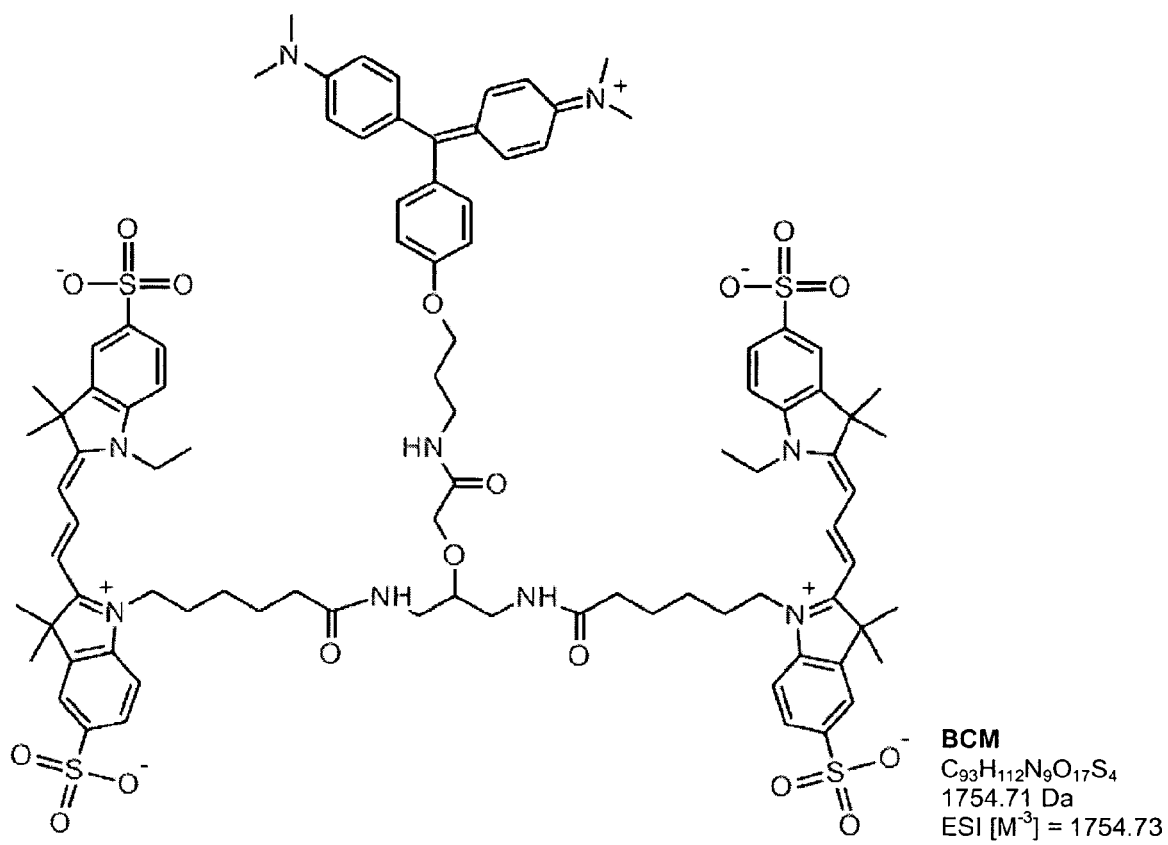
Figure 6C:
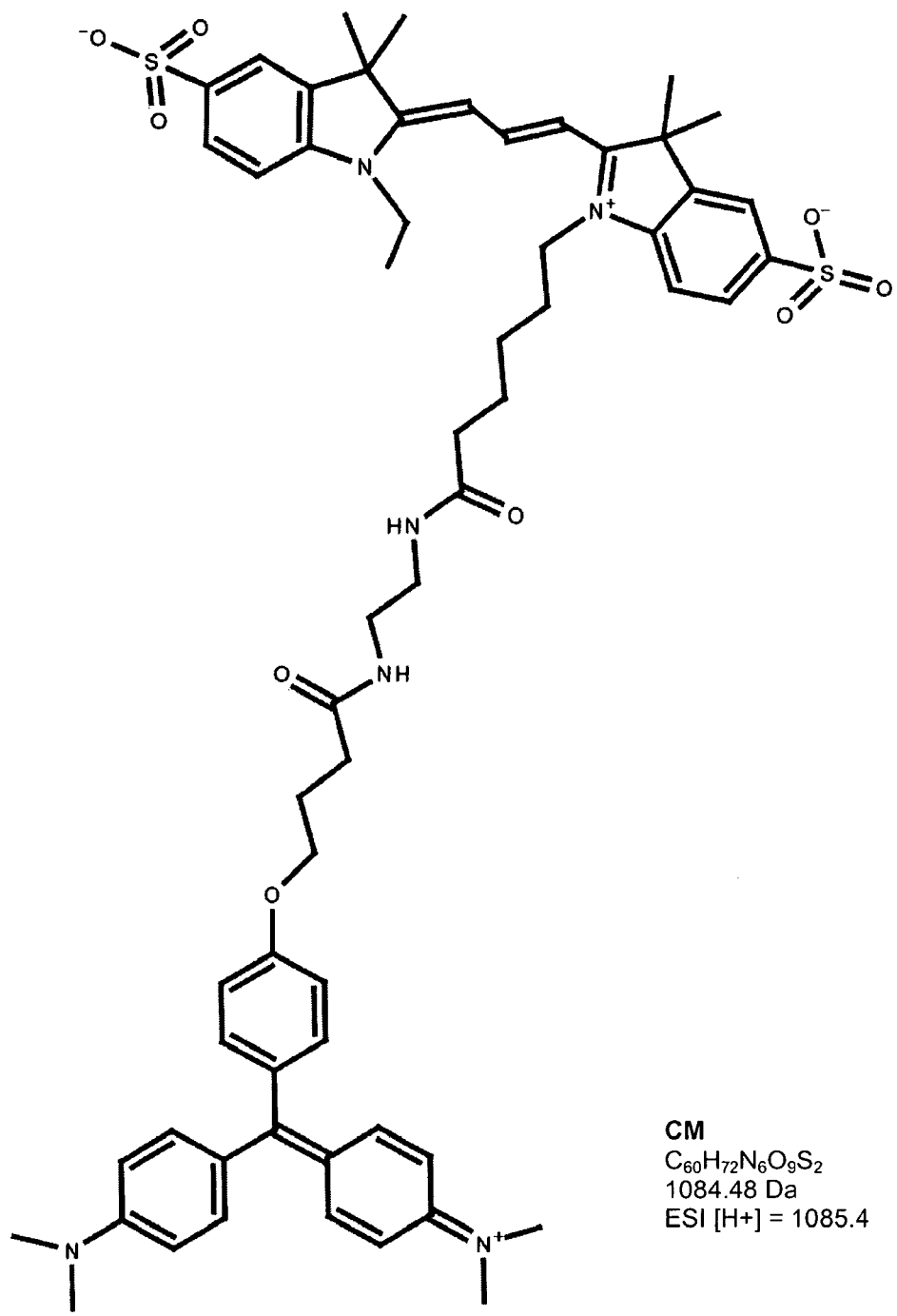
Figure 6D:
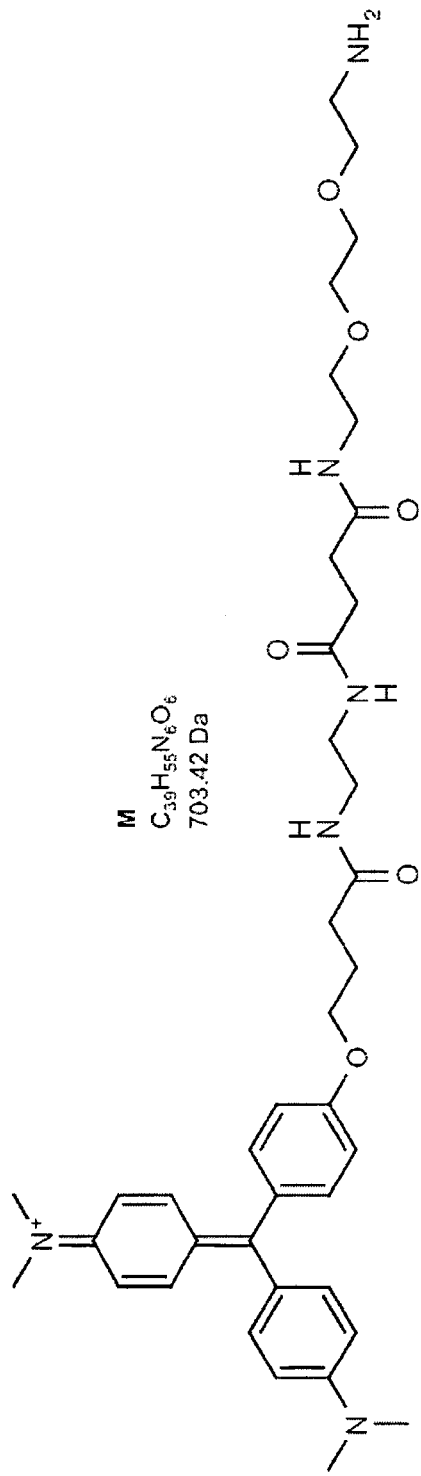

Dyedron Synthesis. Once a given fluorogen has generated a viable fluorogen activating peptide from the library, this fluorogen is incorporated into a dyedron (see, FIG. 5A). A synthetic strategy builds dyedrons by successive rounds of linker addition to a fluorogen head (a divergent synthesis strategy). The resulting intermediates are a series of fluorogenic pre-dyedrons with increasing numbers of branch-points and a specific number of functional amines at the periphery. These amines can be easily reacted with commercially available active esters of donor dyes. One advantage of this strategy is that a number of distinct donor fluorophores can be tested with each pre-dyedron, to determine which fluorophores have the most efficient energy transfer, show the lowest propensity for dye aggregation or nonspecific binding. This synthesis approach was demonstrated using T-linkers for linking up to 4 Cy3 molecules to a single MG molecule. Increases in the density and loading of donor dye can be achieved using tripod linkers rather than T-linkers. This geometry would allow synthesis of dyedrons with 6 or 9 donors and a compact size (see FIG. 5B). For the acetylenic malachite green, the DIR (dimethylindole red) and the MG fluorogens, the Forster radius is comparable, and the direct intramolecular FRET approach is likely to be similarly successful to the results shown for Cy3$_n$MG dyedrons. In the case of indocyanine green, however, the Forster radius is considerably shorter, and the overall FRET efficiency is likely to be reduced. If this is the case, a cascade approach with a mediator dye may be utilized (FIG. 5C) to ensure efficient FRET from the donors, and efficient FRET to the acceptors. In this case, the Cy5-ICG tandem may serve as the "starting fluorogen" for the above linker-expansion synthetic strategy.

Fluoromodule Optimization and Maturation. The properties of the fluorogen activating peptides selected against fluorogen alone are not necessarily optimized for binding and activation of the fluorogenic dyedrons. A reduction of the affinity of clones on addition of progressive numbers of donor dyes to a previously selected fluorogen was noted. To refine the properties of these FAPs specifically for binding and activating fluorogenic dyedrons, affinity maturation of fluorogen binding clones with high quantum yields and tight binding may be carried out by error-prone PCR methods, and the resulting library of mutants is selected for binding and activation of the dyedron, rather than the parent fluorogen. Clones that are capable of binding and activating fluorogenic dyedron at low concentration, and with high quantum efficiency, as determined by flow cytometry (ratio of expression measured with an HA epitope tag to measured brightness of the fluorogen provides a value that correlates to clone quantum yield) are collected and sequenced.

The dyedrons and dyedron systems described herein, and are useful for virtually any assay, imaging system that a fluorogen is useful for. As described in detail herein, the dyedrons are useful in real-time imaging in cells or an organism. As an example, an activator/selectivity component-containing polypeptide can be introduced into a cell by any means, including genetically, by transient or permanent transfection, transduction or transformation of a cell or organism with a nucleic acid comprising a gene for expressing the polypeptide. Alternately, the polypeptide can be introduced into a cell or organism. A fusion protein or complex comprising the activator and selectivity component, such as an antibody, can be used for in situ assays of, for example, fixed cells or tissue. In such an embodiment, the selectivity component is bound to a cell or tissue component, such as a protein, of a cell or tissue, and the activator binds the dyedron, such that the desired cell or tissue component can be localized in the cell or tissue. An activator bound to a selectivity component in a complex or as a fusion protein also can be used in a fluorescent assay akin to an ELISA or RIA, e.g., in a sandwich-type assay. Likewise, a probe comprising the activator and a selectivity component, such as an antibody or a nucleic acid, can be used in detection of a protein or nucleic acid in a western, northern or Southern blot or EMSA, or other electrophoresis methods.

Example 1

Synthesis of Dyedron

NMR spectra were obtained on a Bruker Avance 500 MHz Instrument. The electrospray ionization mass spectrometry (ESI-MS) experiments were run on a Finnigan LCQ quadrupole ion trap mass spectrometer using Xcalibur Ver. 1.2. Mass analysis of the final product "TCM" 13 was performed a ThermoFisher Scientific LCQ classic with Xcalibur version 1.3 software. The sample was desalted and concentrated with a homemade 3 cm C-18 capillary liquid chromatography column and electrosprayed directly into the mass spectrometer. The dye solution was pressure bomb loaded in 1 µL volumes and a 100% water to 20% methanol step "gradient" was used to elute the sample from the column at ~1µ/min.

Compact multi-chromophore dyedrons in FIGS. 6A-D were prepared by a strategy similar to the convergent syntheses of Frechet (Hawker, C. J.; Frechet, J. M. J. *Journal of the American Chemical Society* 1990, 112, 7638-7647), and purified by reverse phase liquid chromatography, yielding branched structures with 1, 2 and 4 Cy3 donor molecules covalently and stoichiometrically decorating the periphery of the molecule and a single MG quenching group at the base of the dyedron.

Figure 7A:
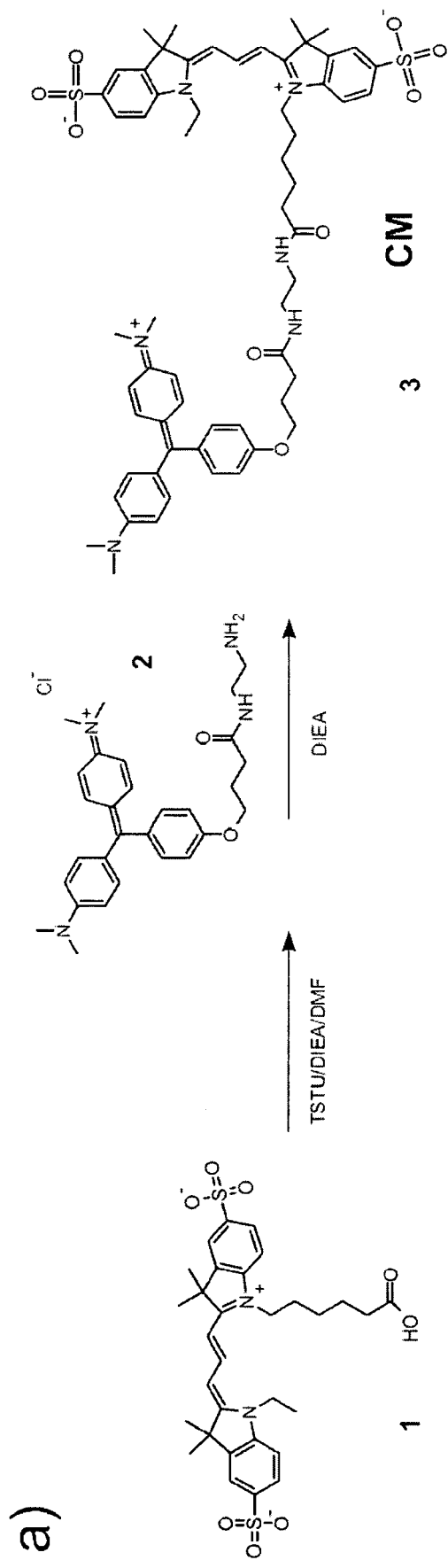
FIGS. 7A-7C. Dyedron synthesis overview. a) Cy3-malachite green (CM); (b) BisCy3-malachite green (BCM); (c) TetraCy3-malachite green (TCM). Bold numbers reference compounds described in Example 1.
Figures 1, 7B:
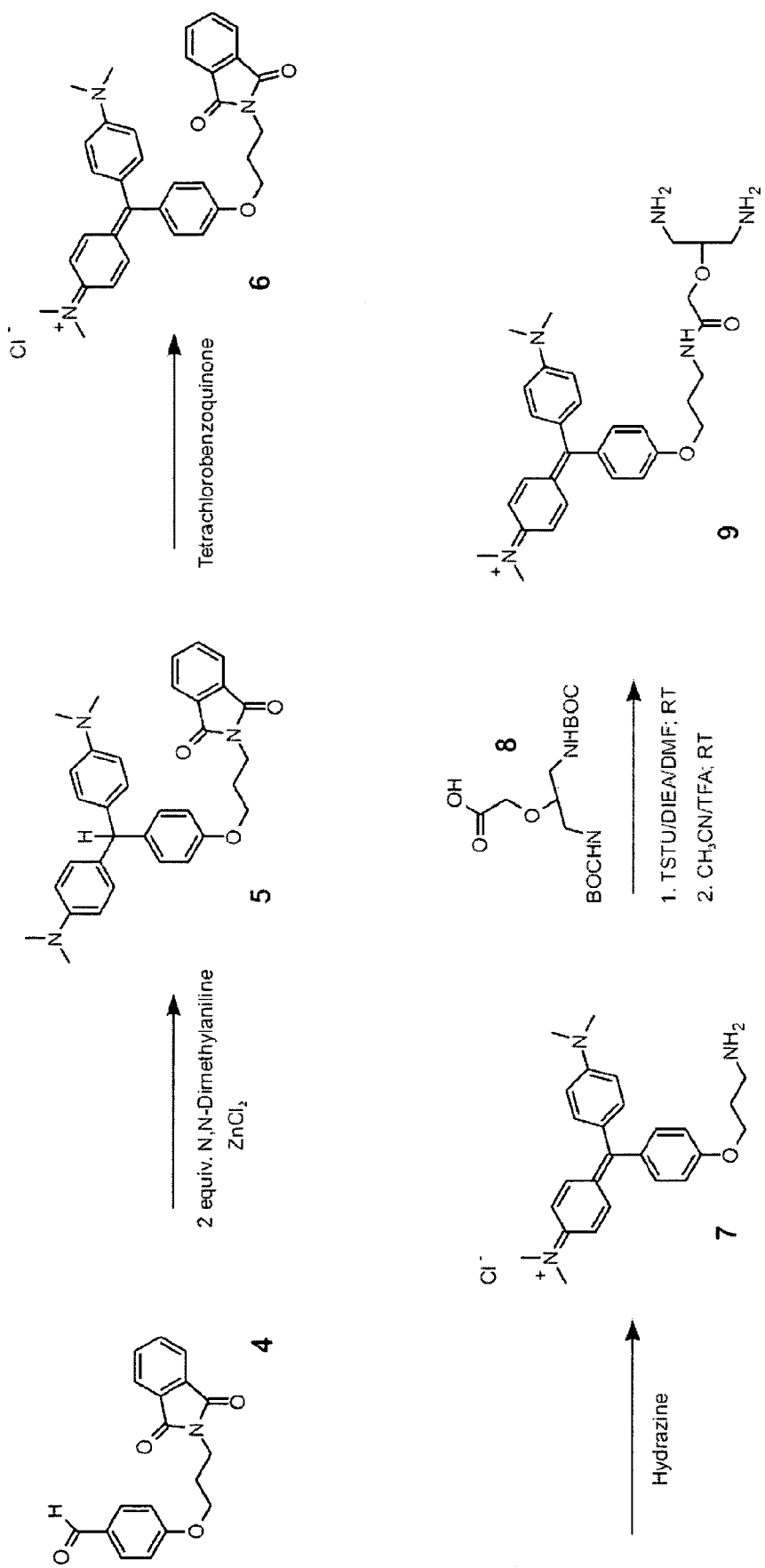
Figure 7B:
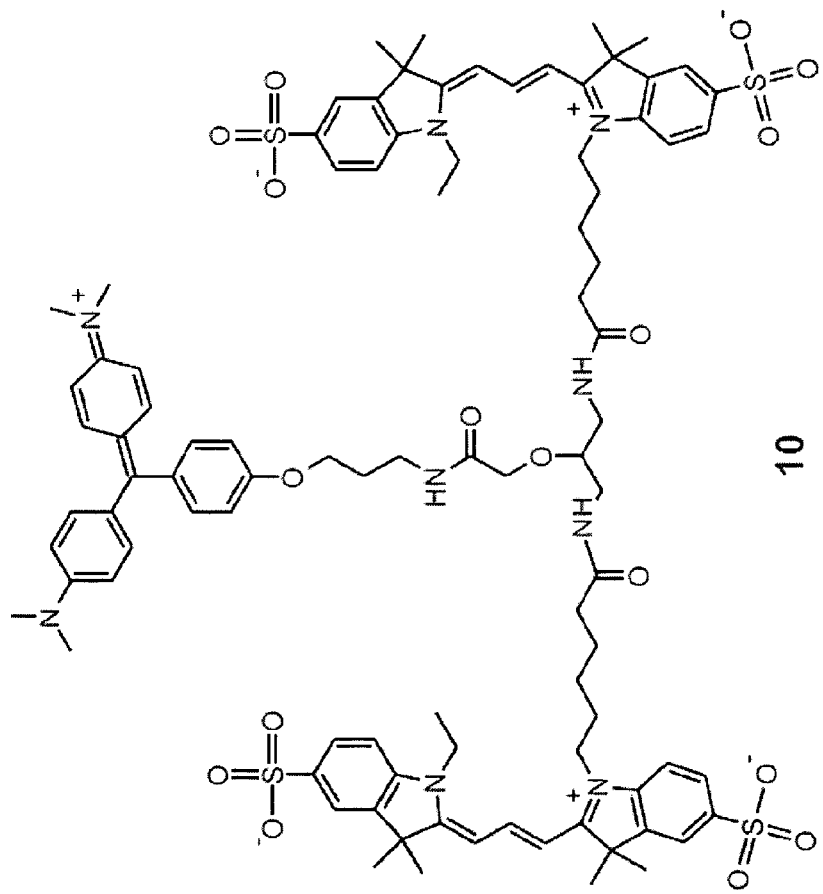
Figure 2:
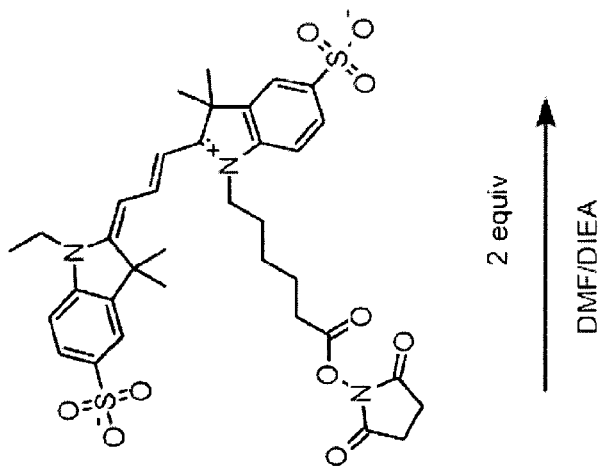
Figure 7C:
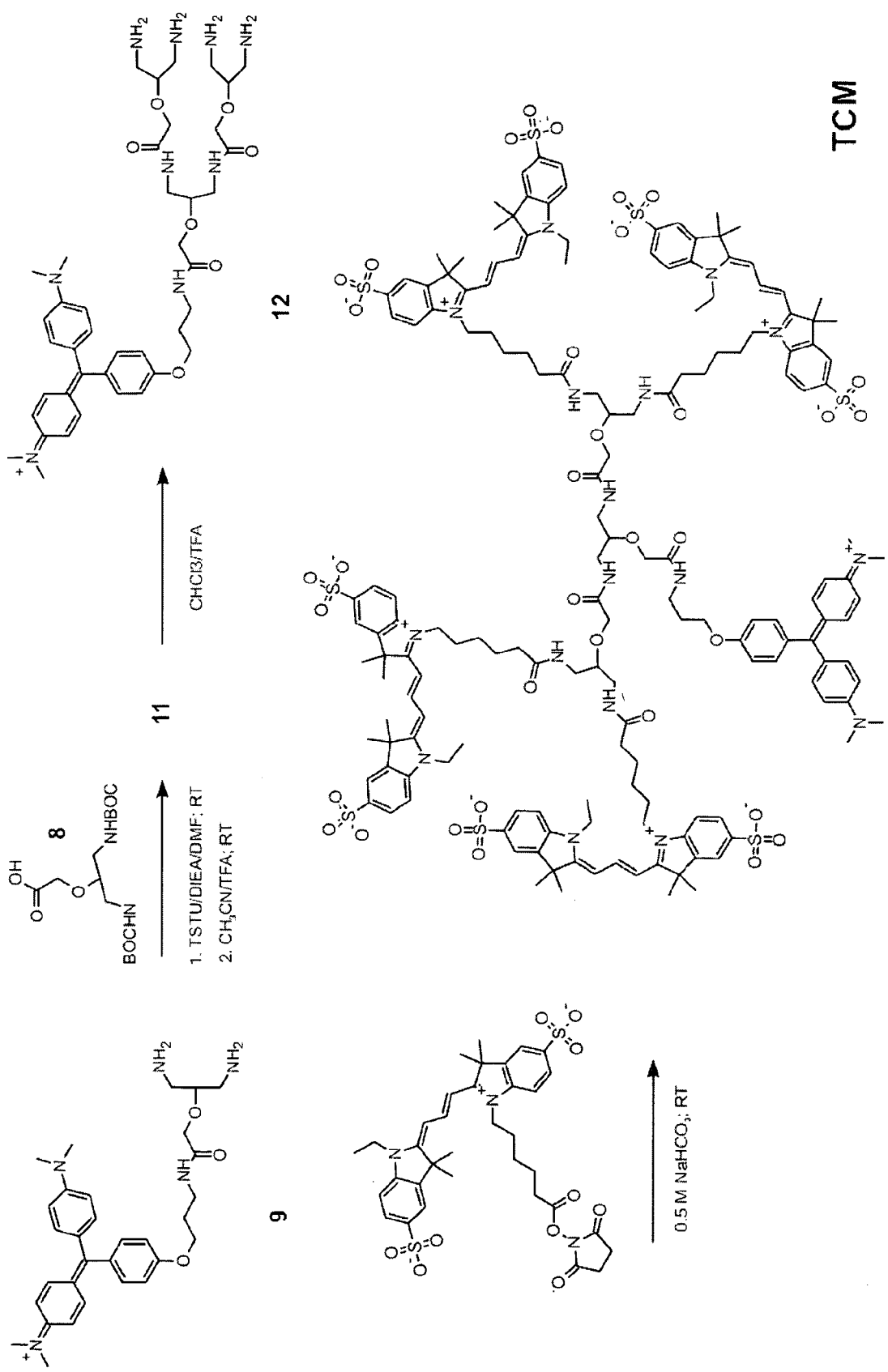

FIGS. 7A-7C depicts the following synthetic scheme for compounds CM, BCM and TCM. NMR spectra were obtained on a Bruker Avance 500 MHz Instrument. The electrospray ionization mass spectrometry (ESI-MS) experiments were run on a Finnigan LCQ quadrupole ion trap mass spectrometer using Xcalibur Version 1.2. Mass analysis of the final product "TCM" 13 was performed a ThermoFisher Scientific LCQ classic with Xcalibur version 1.3 software. The sample was desalted and concentrated with a home-made 3 cm C-18 capillary liquid chromatography column and electrosprayed directly into the mass spectrometer. The dye solution was pressure bomb loaded in 1 µL volumes and a 100% water to 20% methanol step "gradient" was used to elute the sample from the column at ~1 µL/min.

Compound 3 "Cy3.29-Malachite Green" (CM)

1-{6-[(2-{[4-(4-{[4-(dimethylamino)phenyl][4-(dimethyliminio)cyclohexa-2,5-dien-1-ylidene] methyl}phenoxy)butanoyl]amino}ethyl)amino]-6-oxohexyl}-2-[(1E,3Z)-3-(1-ethyl-3,3-dimethyl-5-sulfonato-1,3-dihydro-2H-indol-2-ylidene)prop-1-en-1-yl]-3,3-dimethyl-3H-indolium-5-sulfonate Cy3.29 1 (7 mg, 0.001 mmol) was dissolved in 0.2 mL of dry DMF. TSTU (6 mg, 0.002 mmol) followed by diisopropylethylamine "DIPEA" (3.5 µL; 0.002 mmol) was added. The reaction mixture was stirred for 1 hr at rt. N-[4-[[4-(Dimethylamino)phenyl](4-(-9-mino-6-aza-1-oxa-5-oxo-nonyl)phenyl)methylene]-2,5-cyclohexadien-1-ylidene]-N-methyl-methanaminium chloride 2 (5 mg; 0.001 mmol) (Dick, D. L.; Rao, T. V. S.; Sukumaran, D.; Lawrence, D. S. *Journal of the American Chemical Society* 1992, 114, 2664-2669) was added followed by (3.5 µL; 0.002 mmol) DIEA. The reaction mixture was stirred overnight at rt. Ethyl ether was added (10 mL) to precipitate the product. The organic phase was decanted. The residue dissolved in acetonitrile/water/1% TFA. The reaction mixture was separated by HPLC on a µ-Bondapak 10 µm 7.8×300 mm RP-18 column; eluent: 20-40% acetonitrile/water/0.1 TFA, linear gradient over 20 min/3 mL flow rate. Yield: 8 mg (74%).

$C_{60}H_{72}N_6O_9S_2$, ESI/MS: [H$^+$] m/z (monoisotopic ion): 1085.4. UV/VIS: ethanol $\lambda_{max}$=462; 558; 602; water $\lambda_{max}$=462; 534; 620; $^1$H-NMR (MeOD): 8.53 (1H, t, J=13.5 Hz, Cy3); 7.93 (1H, d, J=1.5 Hz, Cy3); 7.92 (1H, d, J=1.5 Hz, Cy3); 7.90 (2H, m, Cy3); 7.39 (2H, obscured, Cy3); 7.38 (4H, d, J=9.3 Hz, MG); 7.33 (2H, d, J=8.7, MG); 7.16 (2H, d, J=8.7 Hz); 7.02 (4H, d, J=9.3 Hz, MG); 6.53 (1H, d, J=13.5 Hz, Cy3); 6.50 (1H, d, J=13.5 Hz, Cy3); 4.21 (2H, m, Cy3); 4.16 (2H, m, MG); 4.15 (2H, m, Cy3); 3.31 (12H, s, MG); 2.80 (4H, s, linker); 2.40 (2H, t, J=7.4 Hz, MG); 2.19 (2H, t, J=7.2 Hz, Cy3), 2.11 (2H, m, MG); 1.84 (2H, m, Cy3); 1.74 (12Hs, Cy3); 1.68 (2H, m, Cy3), 1.44 (2H, m, Cy3); 1.41 (3H, t, J=7.2 Hz, Cy3).

Compound 5

4,4'-[(4-[3-(1,3-Dihydro-1,3-dioxo-2H-isoindol-2-yl) propoxyphenyl]methylene]bis[N,N-dimethyl-benzenamine 4-(3-Phthalimidopropoxy)benzaldehyde (Dick, D. L.; Rao, T. V. S.; Sukumaran, D.; Lawrence, D. S. *Journal of the American Chemical Society* 1992, 114, 2664-2669) 4 (6.18 g, 20 mmol), N,N-dimethyl aniline (4.87 g, 40 mmol) and zinc chloride (2.8 g, 20 mmol) were dissolved in anhydrous ethanol (250 mL). The reaction mixture was refluxed for 2 days. The product started to precipitate from the reaction mixture after 1 day. The hot reaction mixture was filtered to yield 5.78 g (50%) of a chartreuse colored solid, mp 184-188° C.

$C_{34}H_{35}N_3O_3$ MW: 533.67 g/mol; $^1$H-NMR: (CDCl$_3$) 7.85 (2H, m); 7.72 (2H, m); 6.99 (6H, m); 6.70 (6H, m); 5.32 (1H, s); 4.02 (2H, t, J=6.0 Hz); 3.92 (2H, t, J-6.8 Hz); 2.93 (12H, s); 2.18 (2H, m).

Compound 6 "MG-phthalimide"

[4-[[4-([3-(1,3-Dihydro-1,3-dioxo-2H-isoindol-2-yl)) propoxyphenyl][4-(dimethyl amino)phenyl]methylene]-2,5-cyclohexadien-1-ylidene]-N-methyl-methanaminium chloride"

4,4'-[(4-[3-(1,3-Dihydro-1,3-dioxo-2H-isoindol-2-yl)propoxyphenyl]methylene]bis[N,N-dimethyl-benzenamine 5 (533 mg, 1 mmol) was dissolved in ethylacetate (50 mL). Tetrachlorobenzoquinone (368 mg, 1.5 mmol) was added in small portions. The reaction mixture was refluxed for 2 hrs. After cooling to rt the green solid was filtered off and washed with ethyl acetate. Mp 167-172° C. Quantitative yield. $C_{34}H_{34}ClN_3O_3$ MW: 568.12 g/mol.

$^1$H-NMR: (CDCl$_3$) 7.87 (2H, m); 7.76 (2H, m); 7.37 (4H, d); 7.28 (2H, d); 6.97 (6H, m); 4.21 (2H, t); 3.97 (2H, t); 3.37 (12H, s); 2.28 (2H, quint).

Compound 7 "MG-amine"

[4-[[4-[(3-Aminopropoxy)phenyl][4-(dimethylamino)phenyl]methylene]-2,5-cyclohexadien-1-ylidene]-N-methyl-methanaminium chloride MG-phthalimide 6 (568.12, 1 mmol) was dissolved in 150 ml anhydrous ethanol. Anhydrous hydrazine (0.1 mL, 3 mmol) was added and the reaction mixture was heated at 55° C. for 3 hrs. The reaction mixture was cooled to rt and filtered. The filtrate was acidified with 1M HCl/ethanol. The solids were filtered off and the filtrate concentrated. The residue was purified by column chromatography on RP-18. Eluent: water/acetonitrile/0.1% TFA gradient 10-40% acetonitrile.

$^1$H-NMR: (MeOH) 7.45 (4H, d, J=9.1 Hz); 7.41 (2H, d, J=8.7 Hz); 7.24 (2H, d, J=8.6 Hz); 7.06 (4H, d, J=9.3 Hz); 4.32 (2H, t, J=7.2 Hz); 3.33 (12H, s); 3.25 (2H, t, J=7.2 Hz); 2.25 (2H, m).

Compound 9 "MG-T-bisamine"

N-[4-({4-[3-({[(1,3-diaminopropan-2-yl)oxy] acetyl}amino)propoxy]phenyl}[4(dimethyl amino) phenyl]methylene]-2,5-cyclohexadien-1-ylidene]-N-methyl-methanaminium chloride 2-[2-[[(1,1-Dimethylethoxy)carbonyl]amino]-1-[[[(1,1-dimethylethoxy)carbonyl]amino]methyl]ethoxy]-acetic acid 8 (Lagnoux, D.; Delort, E.; Douat-Casassus, C.; Esposito, A.; Reymond, J.-L. *Chemistry—A European Journal* 2004, 10, 1215-1226) (17.4 mg; 0.05 mmol) were dissolved in 0.1 mL dry DMF. TSTU (16 mg; 0.052 mmol) was added and DIPEA (17 μL; 0.01 mmol). The reaction mixture was stirred for 1 hr. MG-amine 7 (43.8 mg; 0.1 mmol) was added followed by DIPEA (17 μL; 0.01 mmol). The reaction mixture was stirred overnight. The product was precipitated by the addition of ether (3 mL). The precipitate was washed with ether. The residue was dissolved in acetonitrile (0.5 mL). Trifluoroacetic acid (0.1 mL) was added. The reaction mixture was stirred at rt overnight. The solvent was removed under vacuum and the residue was purified by HPLC; RP-18, acetonitrile/water/0.1% TFA; linear gradient 30%-100% acetonitrile; 25 min.

$C_{31}H_{42}N_5O_3Cl \times 2TFA$; $^1$H-NMR: (CD$_3$CN) 7.56 (1H, s, NHC(O)); 7.36 (4H, d, J=8.3 Hz); 7.30 (2H, d, J=7.8 Hz); 7.12 (2H, d, J=8.3 Hz); 6.95 (4H, d, J=8.6 Hz); 4.23 (2H, s); 4.14 (2H, t, J=6.8 Hz); 4.11 (1H, m); 3.40 (2H, m); 2.3-3.17 (4H, m); 3.25 (12H, s); 2.02 (2H, m).

Compound 10 "Bis-Cy3-Malachite Green" (BCM)

2,2'-{[2-(2-{[3-(4-{[4-(Dimethylamino)phenyl][4-dimethyliiminio)cyclohexa-2,5-dien-1-ylidene]methyl}phenoxy)propyl]amino}-2-oxoethoxy)propane-1,3-diyl]bis[imino(6-oxohexane-6,1-diyl)(3,3-dimethyl-5-sulfonato-1H-inodl-1-yl-2-ylidene)(1E,3E)prop-1-en-1-yl-3-ylidene]}bis(1-ethyl-3,3-dimethyl-3H-indolium-5-sulfonate)

MG-T 9 (6 mg, 0.01 mmol) dissolved in 0.1 mL of dry DMF was added to a solution of Cy3.29-OSu (28 mg, 0.04 mol) in 0.1 mL DMF. DIPEA (17 μL) was added. The reaction mixture was stirred at rt overnight. The reaction products were precipitated by the addition of ethyl ether (2 mL). The organic phase was decanted and the residue washed with another portion of ethyl ether. Water (2 mL) was added to the residue. The non-water soluble residue is washed several times with water to remove excess Cy3.29, dissolved in a mixture of acetonitrile/water=40/60 and purified by HPLC; RP-18(30% acetonitrile-100% acetonitrile; linear gradient over 25 min).

$C_{93}H_{112}N_9O_{17}S_4$ ESIMS (negative) [M$^{-1}$] m/z 1754.73 monoisotope. $^1$H-NMR: (MeOD) 8.53 (2H, dd, J=13.5 Hz, Cy3); 7.94 (2H, d, J=1.5 Hz, Cy3); 7.92 (2H, d, J=1.5 Hz, Cy3); 7.91 (2H, dd, J=8.3 Hz, 1.5 Hz, Cy3); 7.88 (2H, dd, J=8.3 Hz, 1.5 Hz, Cy3); 7.38 (2H, d, J=8.3 Hz, Cy3); 7.37 (2H, d, J=8.3 Hz, Cy3); 7.34 (4H, d, J=9.3 Hz, MG); 7.30 (2H, d, J=8.8 Hz, MG); 7.14 (2H, d, J=8.8 Hz, MG); 7.00 (4H, d, J=9.3 Hz MG); 6.54 (2H, d, J=13.5 Hz, Cy3); 6.52 (2H, d, J=13.5 Hz, Cy3); 4.22 (4H, m, Cy3); 4.18 (2H, m, MG); 4.16 (4H, m, Cy3); 4.03 (2H, s, linker); 3.44 (2H, obscured, MG); 3.29 (12H, s, MG); 3.43 (1H, m, linker); 3.25 (2H, m, linker); 3.16 (2H, m, linker); 2.23 (4H, t, J=7.4 Hz, Cy3); 2.05 (2H, m, MG); 1.84 (4H, m, Cy3); 1.74 (24H, s, Cy3); 1.67 (4H, m, Cy3); 1.43 (4H, m, Cy3); 1.42 (6H, t, J=7.2 Hz, Cy3).

Compound 11 "MG-TT-Boc"

N-(4-{(4-{[7-{[(tert-butoxycarbonyl)amino]methyl}-13-(6-{[(tert-butoxycarbonyl)amino]methyl}-11,11-dimethyl-3,9-dioxo-5,10-dioxa-2,8-diazadodec-1-yl)-2,2-dimethyl-4,10,16-trioxo-3,8,14-trioxa-5,11,17-triazaicosan-20-yl]oxy}phenyl)[4-(dimethylamino)phenyl]methylidene}cyclohexa-2,5-dien-1-ylidene)-N-methylmethanaminium chloride To a solution of 2-[2-[[(1,1-dimethylethoxy)carbonyl]amino]-1-[[[(1,1 dimethylethoxy)carbonyl]amino]methyl] ethoxy]-acetic acid 8 (Dick, D. L.; Rao, T. V. S.; Sukumaran, D.; Lawrence, D. S. *Journal of the American Chemical Society* 1992, 114, 2664-2669) (35 mg; 0.1 mmol) in 0.1 mL dry DMF, TSTU (32 mg; 0.12 mmol) was added and DIPEA (34 μL; 0.2 mmol). The reaction mixture was stirred for 1 hr. After completion of the reaction "MG-T" 9 (24 mg; 0.04 mmol) was added followed by DIPEA (34 μL; 0.1 mmol). The reaction mixture was stirred overnight at RT. The product was precipitated by the addition of ether (3 mL). The precipitate was dissolved in chloroform and purified by chromatography on silicagel (chloroform/5-30% methanol/0.1% ammonia). The product fractions were concentrated to give 40 mg (81%) of a dark green resin.

$C_{41}H_{62}N_9O_{17}{}^+Cl^-$ ESI:MS$^+$792.47 monoisotope. $^1$H-NMR: (CDCl$_3$, 500 MHz) δ 8.55 (2H, m, amide); 8.43 (1H, m, amide); 7.39 (4H, d, J=9.1 Hz); 7.30 (2H, d, J=8.4 Hz); 7.14 (2H, d, J=8.4 Hz); 6.90 (4H, d, J=8.9 Hz); 5.90 (4H, m, Boc-amide); 4.27 (2H, t, J=6.4 Hz); 4.13 (2H, s); 4.05 (4H, s); 3.53 (6H, m); 3.47 (2H, m); 3.35 (5H, m); 3.32 (12H, s, MG-N-methyl); 3.15 (4H, m); 2.15 (2H, m); 1.43 (36H, s, Boc).

Compound 12 "MG-TT"

N-(4-{[4-({15-amino-14-(aminomethyl)-8-[({[(1,3-diaminopropan-2-yl)oxy]acetyl}amino)methyl]-5,11-dioxo-7,13-dioxa-4,10-diazapentadec-1-yl}oxy)phenyl][4-(dimethylamino)phenyl]methylidene}cyclohexa-2,5-dien-1-ylidene)-N-methyl methanaminium chloride Trifluoroacetic acid (100 μL) was added to a solution of 40 mg of MG-TT-BOC 11 in chloroform (1 mL). The reaction mixture was stirred overnight. The product precipitates from the reaction mixture. The supernatant was discarded and the residue washed with chloroform (2×1 mL). The product was used as such in the next reaction step.

ESIMS (negative) [M$^{+1}$] m/z 792.5 monoisotope. $^1$H-NMR: (MeOD, 500 MHz) δ 7.42 (4H, d, J=9.1 Hz); 7.37 (2H, d, J=8.8 Hz); 7.18 (2H, d, J=8.8 Hz); 7.04 (4H, d, J=9.4 Hz); 4.30 (4H, s); 4.21 (2H, t, J=6.1 Hz); 4.14 (2H, s); 4.06 (2H, m); 3.64 (1H, m); 3.47 (2H, t, J=7.2 Hz); 3.46 (2H, dd; J=14.4 Hz, 4.9 Hz); 3.38 (2H, dd, J=14.1 Hz, 5.8 Hz); 3.33 (12H, s); 3.30 (4H, dd, J=14.4 Hz, 3.8 Hz); 3.17 (4H, dd, J=13.8 Hz, 7.1 Hz); 2.09 (2H, quint).

Compound 13 "TetraCy3-Malachite Green" (TCM)

Trisodium 2-{(1E,3E)-3-[1-(15-[2-({3-[4-({4-[chloro(dimethyl)-1$^5$-azanylidene]cyclohexa-2,5-dien-1-ylidene}[4-(dimethylamino)phenyl]methyl)phenoxy]propyl}amino)-2-oxoethoxy}-29-{(2E)-2-[(2E)-3-(1-ethyl-3,3-dimethyl-5-sulfonato-3H-indolin-2-yl)prop-2-en-1-ylidene]-3,3-dimethyl-5-sulfonato-2,3-dihydro-1H-indol-1-yl}-21-{[(6-(2E)-2-[(2E)-3-(1-ethyl-3,3-dimethyl-5-sulfonato-3H-indolium-2-yl)prop-2-en-1-ylidene]-3,3-dimethyl-5-sulfonato-2,3-dihydro-1H-indol-1-yl}hexanoyl)amino]methyl}-9-{[(6-(2Z)-2-[(2E)-3-(1-ethyl-3,3-dimethyl-5-sulfonato-3H-indolium-2-yl)prop-2-en-1-ylidene]-3,3-dimethyl-5-sulfonato-2,3-dihydro-1H-indol-1-yl}hexanoyl)amino]methyl}-6,12,18,24-tetraoxo-10,20-dioxa-7,13,17,23-tetraazanonacos-1-yl)-3,3-dimethyl-5-sulfonato-1H-indol-2(3H)-ylidene]prop-1-en-1-yl}-1-ethyl-3,3-dimethyl-3H-indolium-5-sulfonate To a solution of "MG-TT" 12 (16.5 mg, 0.02 mmol) in 0.5 M sodium bicarbonate/20% acetonitrile (0.5 mL) was added Cy3.29-OSu (100 mg, 0.15 mmol) a solid in small portions over a 6 hr period under stirring. The progression of the labeling reaction was monitored by HPLC RP18-water/acetonitrile; 10-100% linear gradient 30 min (detection at 550 nm and 630 nm). After the last addition, the reaction mixture was stirred for 1 hr at rt. The reaction mixture was passed through a Bio-gel P2 column (19 mm×500 mm) to separate non-reacted Cy3.29 from the reaction products. The fast-moving fractions were collected, concentrated and separated on a u-Bondapak RP-18 prep HPLC column (19 mm×300 mm) Flow: 10 mL/min water/acetonitrile (10-25% 30 min; 30%100% 30 min). Yield: 15 mg (22%). $C_{165}H_{202}N_{17}O_{15}S_8Na_3$ LC-ESIMS (negative) $[M^{-3}]$ m/z 1079.1, monoisotope; calcd. for $C_{165}H_{202}N_{17}O_{15}S_8^{-3}$ m/z 1079.07. $^1$H-NMR.

Example 2

Figure 8:
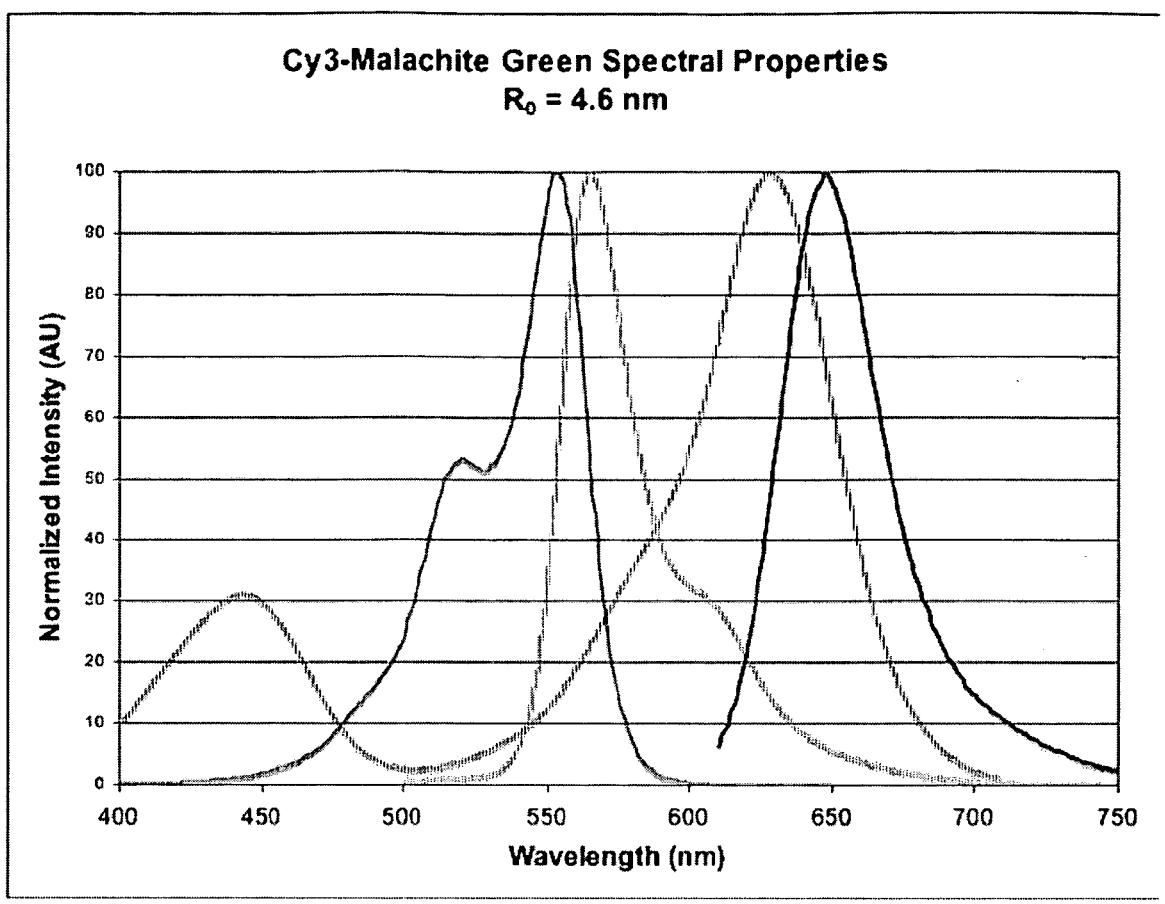
FIG. 8 shows representative spectral properties of a dyedron pair. The Cy3-Malachite Green pair excitation and emission spectra. The bold lines show the donor excitation and activated emission expected from the final activated dyedron.
Figure 9:
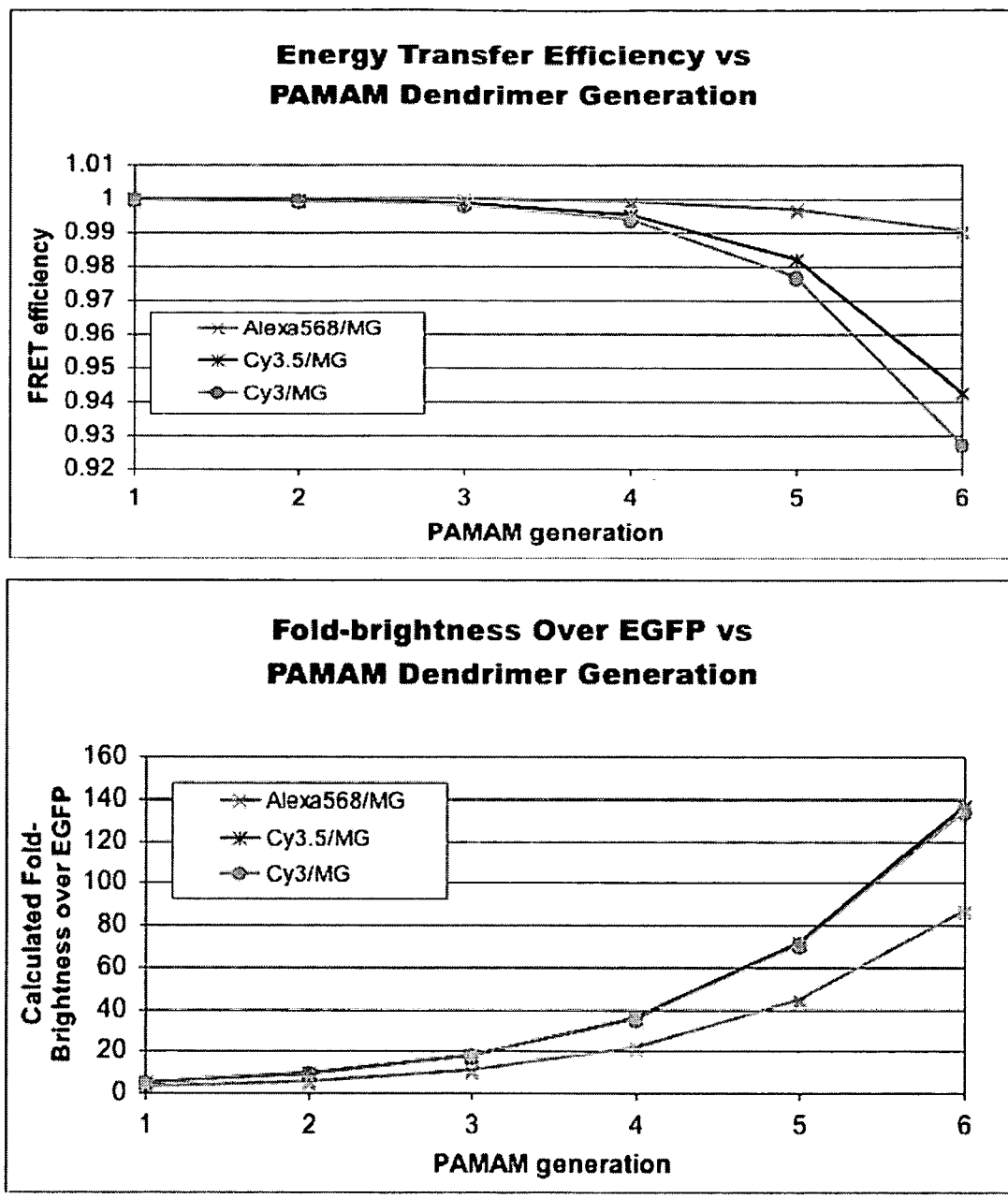
FIG. 9 shows calculated energy transfer efficiency (top) and fold-brightness over EGFP (bottom) of some quenched dyedrons based on a Forster transfer model.

The initial probe design is based on well-characterized organic fluorescent dyes and activatable fluorogens (FIG. 8). Malachite green is a nonfluorescent triphenylmethane dye, which is activated by a selected scFv to a highly fluorescent state (>15,000 fold) with emission maximum at 656 nm. The efficiency of our probes relies on significant energy transfer between the donor (Cy3) molecules and the fluorogen molecule. The Forster radii for all models were calculated from the formula put forward by Stryer. From these numbers and the average experimental properties of PAMAM dendrons, we were able to model the energy transfer efficiency (E) as a function of dendron generation for each of our potential dye pairs. FIG. 9—top shows the values of E as a function of generation for each pair. For each of these dye pair choices up to generation 4, the efficiency is in excess of 99%, providing reagents with the potential for dramatic switching with high extinction.

Assuming the properties of these probes will follow the solution dye properties, we analyzed the potential for enhanced excitation of the acceptor dye and for enhanced brightness in single molecule analysis (FIG. 9—bottom), as compared to EGFP. In this analysis, the molecular extinction coefficient of the donor dyes was multiplied by the number of functional groups in a given dendron generation. To give the effective extinction of the acceptor, this number was scaled by the FRET efficiency (E) calculated above. These values were scaled by the reported quantum yield of the acceptor molecule under activated conditions (MG-scFv QY=0.24). This gave a measure of the activated molecular brightness compared to EGFP (53,000 $M^{-1}cm^{+1}$ and QY=0.60) demonstrating that probes can be developed that are potentially 5-140× brighter than a single visible fluorescent protein, easily moving into range of single molecule detection in standard fluorescence microscopes. In addition, the shift of the excitation from blue to yellow dramatically reduces the autofluorescence, and the long stokes shift and far-red emission improves detection efficiency and effective signal-to-noise.

To test the impact of high loading on donor array fluorescence, two cystamine core PAMAM dendrimers (Gen2-16 $NH_2$ and Gen3-32 $NH_2$) were labeled with an excess of monoreactive Cy3-NHS ester. After removal of excess dye by gel filtration the resulting macromolecules were analyzed by electrophoresis, and found to have low net mobility. Because each Cy3 molecule carries one net negative charge, a fully modified dendron should have a net charge of −2. The lack of mobility observed in these conjugates suggests that they are substantially modified, although mass spectroscopy has not yet confirmed this. However, these conjugates allow for the assessment of the potential risk of donor quenching. Surprisingly, we found that the per-dye quantum efficiency reduced only slightly, in spite of significant crowding of the dyes (Table 1). In addition, no significant shifting or spectral changes was found, showing that these donor arrays do not form aggregates in solution.

TABLE 1

| Generation PAMAM | Dyes/Dendron | Estimated Diam. (nm) | F dendrimer F free | Relative Brightness |
|---|---|---|---|---|
| Free dye | 1 | 1.5 | 1 | 1 |
| Gen2 | 8 | 4.2 | 0.72 | 5.8 |
| Gen3 | 16 | 4.6 | 0.58 | 9.3 |

Figure 10:
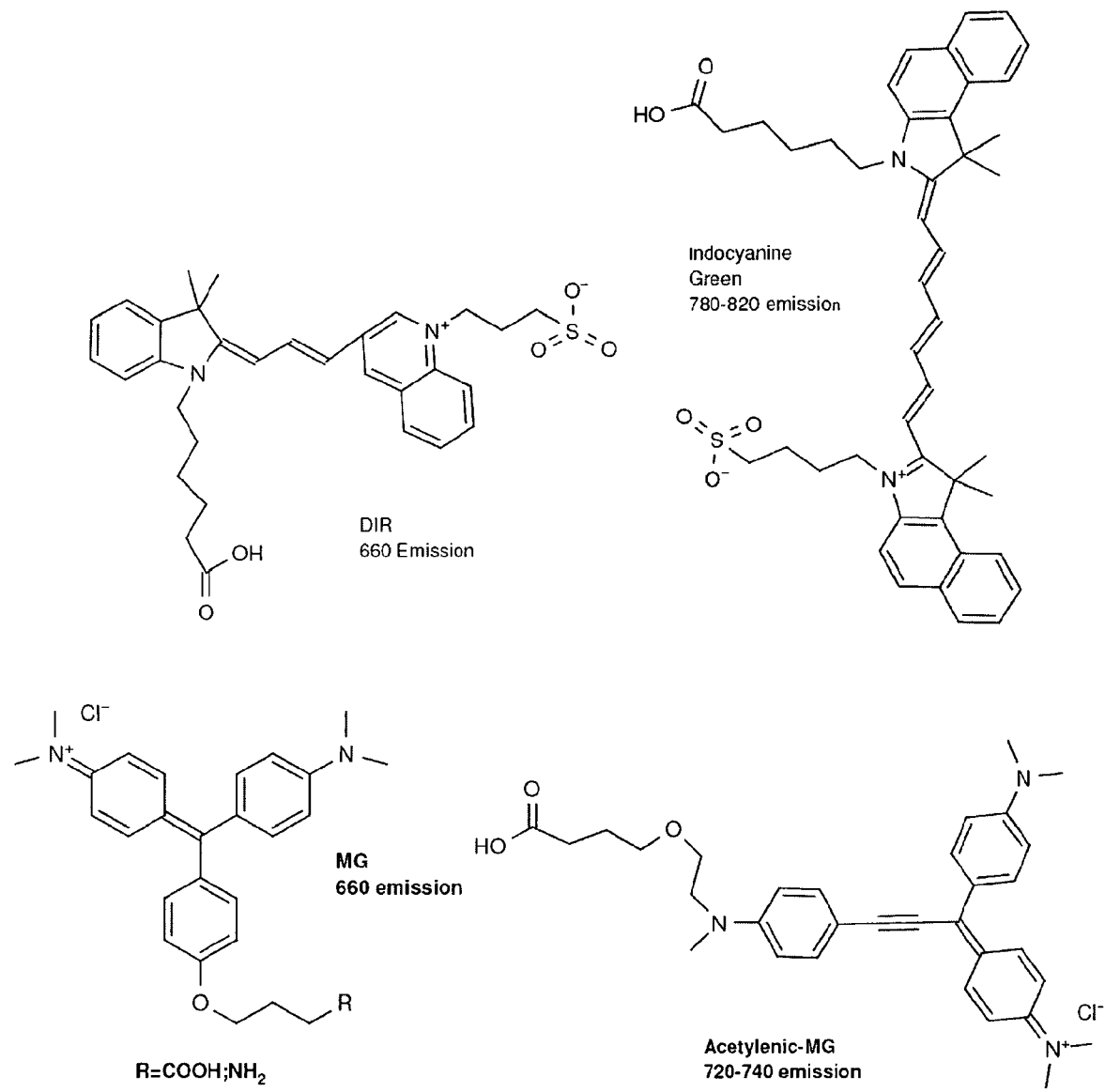
FIG. 10 shows examples of acceptors for fluorogenic dyedron synthesis and fluoromodule development.

The fluorogenic dyedrons are designed as energy transfer pairs between Cy3 and existing (and expected) fluorogens. Malachite green is an essentially nonfluorescent triphenylmethane dye, activated by a selected scFv to a highly fluorescent state (>15,000 fold) with an emission maximum at 656 nm. The probes rely on efficient energy transfer between the donor (Cy3) molecules and the fluorogen molecule. Redder fluorogens for development into fluoromodules with fluorogenic dyedrons in this project are shown in FIG. 10, and include an acetylenic derivative of malachite green (730 nm emission), DIR, and derivatives of indocyanine green (~800 nm emission), which can be attached to the linking dendron by their carboxyl groups. The acetylenic derivative of malachite green and derivatives of indocyanine green have been selected because they have very low quantum yields in water (≤0.003) and environmentally sensitive fluorescence properties, which is one of the strongest indicators of potential fluorogenicity.

Example 3

Methods

Buffer System.

A modified phosphate buffered saline system (PBS+) was used in all experiments unless noted (137 mM NaCl, 2.7 mM KCl, 10 mM $Na_2HPO_4$, 2 mM $KH_2PO_4$, 2 mM EDTA, 0.1% w/v Pluronic F-127 (Anatrace), pH 7.4).

Absorbance Spectra.

Spectra were taken on an HP Lambda45 spectrophotometer. The extinction coefficient for MG-2p in ethanol/5% HAc was determined to be 91,500 $M^{-1}cm^{-1}$ by calibrating against the half-salt of malachite green oxalate (ACROS) in the same solvent. The acidified ethanol/PBS+ absorbance ratio of MG-2p gave an extinction coefficient in PBS+ of 50,700 $M^{-1}cm^{-1}$. This value was then multiplied by the factor increases observed when binding MG-2p and the MG band of CM, BCM, and TCM dyedrons to L5-MG E52D (respectively 1.56, 1.78, 1.93, 1.80) to give effective MG extinction coefficients for each fluorogen. Ratioing the 552 nM dyedron absorbances to the effective MG coefficients gave the dyedron extinction coefficients reported in Table 2.

Fluorescence Spectra.

Figure 11:
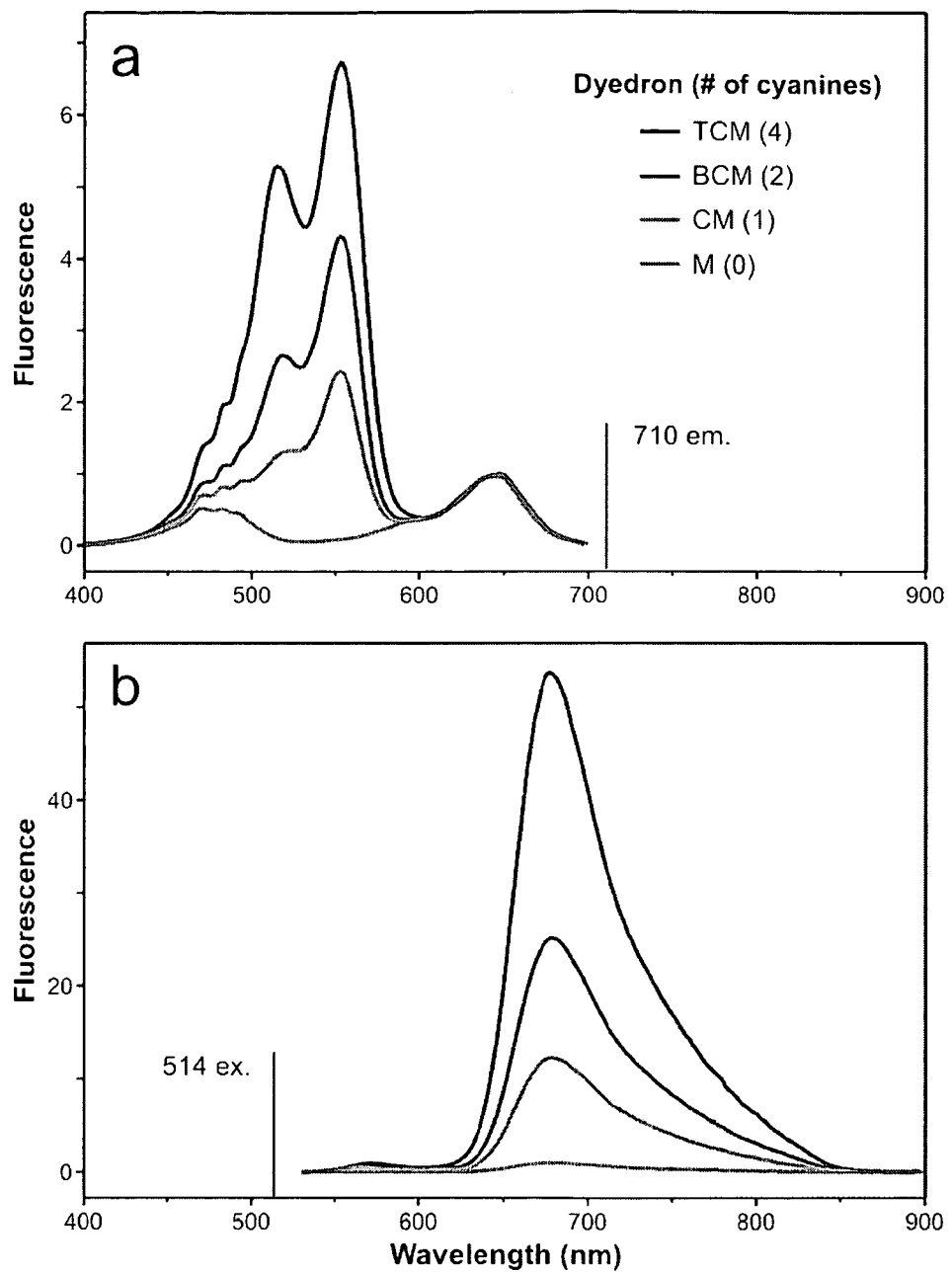
FIG. 11. a) Fluorescence excitation of dyedron/L5-MG E52D complexes (710 nm emission). Fluorescence is expressed as a multiple of the MG excitation peak at 648 nm, to which spectra have been normalized. b) Relative emission of dyedron/L5-MG E52D complexes (514 nm excitation). Spectra have been normalized to the MG excitation peak, and fluorescence is expressed as multiple of the MG emission maximum at 680 nm. Relative emission is sensitive to excitation wavelength.

Spectra were taken on a Quantamaster monochromator fluorimeter (Photon Technology International). To assess fluoromodules (FIG. 11), ~300 nM MG-2p or dyedron was equilibrated with 3 μM L5-MG E52D FAP for 2 hrs at RT prior taking spectra. Fluoromodule and free fluorogen spectra were corrected for PBS background and wavelength dependent photomultiplier sensitivity.

Quantum Yields.

Fluoromodules were assembled as above, and quantum yields based on the acceptor MG excitation band were determined as described using Cy5.18 as the calibration dye (Szent-Gyorgyi, C., et al., *Nature Biotechnology* 2008, 26, 235-240). Quantum yields determined with 620 nm excitation (Table 2) were essentially the same as unreported quantum yields determined with 590 nm excitation (<5% difference).

Microplate Fluorimetry.

Microplate fluorometry was carried out on a Tecan Safire2 microplate reader using 96 well microplates with 5×10$^6$ yeast cells/well. Fluorescence readings were normalized to the number of yeast surface displayed FAPs by analysis of immunolabeled scFv c-myc epitope using a FACSDiva flow cytometer (Szent-Gyorgyi, C., et al., *Nature Biotechnology* 2008, 26, 235-240).

Microscopy.

All images were taken on a Zeiss 510 MetaNLO confocal microscope (See Supporting Information table 3 for settings). Image analysis using the native 12-bit dynamic range of the microscope was carried out with Zeiss ZEN 2007 software. Freshly harvested and washed live yeast cells (20 μl of ~3×10$^7$ cells/ml suspension in PBS w/o Pluronic F-127 or EDTA) were immobilized on 35 mm culture dishes with 14 mm optical windows (MatTek Corporation, Ashland, Mass.) that had been precoated with 1 mg/ml concanavalin-A. Cells were allowed to bind for 10 minutes, and then overlain with 1 ml of PBS+ or scFv induction medium (Szent-Gyorgyi, C., et al., *Nature Biotechnology* 2008, 26, 235-240) containing the appropriate concentration of dyedron, and gently mixed for 30 minutes on a rotary shaker to ensure equilibration of dye and cells. HeLa cells were grown in DMEM on uncoated 35 mm culture dishes (see above). Microinjection and confocal microscopy were carried out in DMEM as described below. Compact multi-chromophore dyedrons in FIG. 6 were prepared as described in Example 1.

For detailed study of dyedron properties, we employed a 110 amino acid scFv (L5-MG E52D) derived from the original L5-MG clone (see, WO 2008/092041) by directed evolution to increase affinity and brightness when bound to MG; to demonstrate that directed evolution can generate dyedron/FAP fluoromodules with brightness significantly greater than dyes and fluorescent proteins, we subsequently characterized additional L5-MG derivatives L91S and E52D L91S (FIG. 12A). Additional FAPs are shown in FIG. 12B.

Peptide sequences of secreted L5-MG activator and evolved derivative scFvs are shown in FIG. 12A. The 110 amino acid antibody light chain variable region that comprises the dyedron binding unit is underlined. Amino acids acquired by directed evolution of L5-MG parent (Szent-Gyorgyi, C., et al., *Nature Biotechnology* 2008, 26, 235-240) that confer expression phenotypes (underlined); gray-highlighted amino acids are mutations that are not correlated with expression changes. L5-MG E52D was an initially characterized derivative that was chosen for systematic study of the dyedron series because in comparison to L5-MG, it is brighter and binds dyedrons more tightly when displayed on the cell surface (FIG. 13). Although the L91S derivative is considerably brighter than the E52D mutant, it binds the dyedron series rather poorly and is less suited for quantitative comparisons (FIG. 13). The subsequently characterized double mutant E52D L91S was found to retain the high binding affinity of E52D and improve upon the brightness of L91S (FIG. 13), and thus is the current FAP of choice for imaging and assay applications using dyedrons.

FIG. 13 depicts improvement of TCM fluoromodules by directed evolution. L5-MG FAP was subjected to mutagenesis, and yeast cell surface displayed FAPs screened for increased brightness and binding affinity using MG-2p. Yeast cells displaying L5-MG and derivatives carrying the depicted point mutations (FIG. 14) were assayed in PBS+ for TCM fluorescence (554 nm excitation/660 nm emission) in a 96-well microplate format. Data are normalized to number of expressed FAPs determined by FACS analysis of immunostained c-myc epitope.

Spectral Characterization of Dyedrons Bound to L5-Mg E52D

Free in solution, all dyedrons showed >99% quenching of Cy3 fluorescence by MG (Table 2), and essentially undetectable fluorescence in the spectral range associated with MG, consistent with the extremely low quantum yield of MG in the absence of an activating polypeptide (Babendure, J. R.; Adams, S. R.; Tsien, R. Y. *Journal of the American Chemical Society* 2003, 125, 14716-14717). Fluorescence quantum yield of the unbound TCM dyedron was <0.0005, so direct emission of the donors is efficiently quenched and does not interfere with detection of FAP-activated dyedron.

TABLE 2

Properties of L5-MG E52D activated dyedrons.

| Dyedron | M | CM | BCM | TCM |
|---|---|---|---|---|
| $\epsilon_{max}$ [nm]$^a$ | 642 | 552 | 551 | 552 |
| $\epsilon_{max}$ [M$^{-1}$cm$^{-1}$]$^a$ | 79,000 | 140,000 | 290,000 | 530,000 |
| $\phi MG^{a,b}$ | 0.055 | 0.057 | 0.047 | 0.054 |
| $\epsilon \times \phi / 10^3$ (brightness) | 4.4 | 8.0 | 14 | 29 |
|  | EGFP = 32$^c$ | | E52D L91S = 160$^d$ | |
| $F_{532}/F_{635}{}^a$ | 0.05 | 1.54 | 2.86 | 4.95 |
| $FACS_{532}/FACS_{635}{}^e$ | 0.07 | 2.17 | 3.27 | 6.89 |
| $K_D$ [nM]$^f$ | <1 | <1 | 4.0 | 15 |
| $F_{quenched}/F_{free}{}^g$ | N/A | 0.0084 | 0.0036 | 0.0037 |

$^a$Determined for soluble dyedron/L5-MG E52D complex.
$^b$Quantum yield for MG excitation peak determined with 620 nm excitation.
$^c$See Patterson, G. H.; Knobel, S. M.; Sharif, W. D.; Kain, S. R.; Piston, D. W. *Biophysical Journal* 1997, 73, 2782-2790.
$^d$From data in FIG. 13 as ratio of fluorescence of cell surface displayed L5-MG E52D L91S to L5-MG E52D at 30 nM TCM.
$^e$Numerator and divisor calculated from data as (median of stained population - median of unstained control).
$^f$Determined for dyedrons binding to yeast cell surface displayed L5-MG E52D.
$^g$Calculated as total absorbance normalized fluorescence (530-800 nm) of dyedron divided by total absorbance normalized fluorescence of Cy3.29. The MG absorbance peak was used for dyedron normalization.

The TCM dyedron, when injected into the cytoplasm of living mammalian cells, produced low levels of fluorescence, essentially undetectable compared to the positive signal under similar imaging conditions.

Binding affinity of dyedrons to yeast cell surface displayed scFv was determined as follows. Yeast JAR200 cells expressing L5-MG E52D were suspended at $10^7$ cells/ml in modified PBS+ buffer in the presence of the indicated dyedron concentrations. Fluorescence was read on a Safire2 plate fluorimeter. $K_D$ values reported in Table 2 were determined using GraphPad Prism 4 software fits to the one site hyperbolic binding curves shown here. Under these conditions, $K_D$ values below 1 nM cannot be determined precisely. Plateau fluorescence levels correspond closely to the relative fluorescence signals seen in flow cytometric analyses using 635 nm laser excitation of the MG band (Table 3).

TABLE 3

Flow cytometric quantification of dyedron binding to yeast displayed L5-MG E52D

|  |  | 532 laser |  | 635 laser |  |
|---|---|---|---|---|---|
|  | Dyedron | median | mean | median | mean |
| JAR200 | None | 59 | 89 | 64 | 102 |
| L5-MG | M | 335 | 435 | 2635 | 7089 |
| E52D | CM | 6170 | 15946 | 2793 | 7455 |
|  | BCM | 6912 | 17894 | 2047 | 5521 |
|  | TCM | 13761 | 35064 | 2141 | 5727 |
| JAR200 | None | 80 | 112 | 60 | 100 |
|  | M | 76 | 111 | 74 | 118 |
|  | CM | 95 | 123 | 65 | 108 |
|  | BCM | 84 | 113 | 64 | 105 |
|  | TCM | 98 | 126 | 64 | 107 |

Experiments employ yeast strain JAR200 (a G418 resistant EBY100 derivative) expressing L5-MG E52D scFv on the cell surface and control strain JAR200 that does not express scFv. Cells were suspended in PBS+ buffer with 300 nM of respective dyedron and analyzed on a FACS Diva flow cytometer using 532 nm and 635 nm lasers with a 675/50 bandpass emission filter. FACS Diva software was used for quantification. Mean values were taken over gated positive populations for scFv expressing cells: median values were taken over the entire cell population in all cases, accounting for lower values for cells experssing scFv.

Spectra of 100 nM dyedron in PBS+ buffer were taken as described and corrected for PBS+ background and wavelength dependent photomultiplier sensitivity. Fluorescence of free dydron is greatly reduced relative to L5-MG E52D FAP activated dydron. As a comparison, the maximal fluorescence of free TCM is 16,430 at 572 nm, but in the same experiment, the fluorescence of FAP-bound TCM is 1,675,000 at 676 nm.

At a single concentration of dye molecule in the presence of excess L5-MG E52D, MG-probe normalized excitation spectra (710 nm detection) reveal that contributions of the Cy3 excitation increase in direct proportion to Cy3 number, and show that these simple modifications substantially enhance the overall excitation cross-section of the construct as compared to MG alone (FIG. 11A and Table 2). The magnitude of cross-section enhancement correlates well with the absorbance of Cy3 ($\epsilon$=150,000 M$^{-1}$ cm$^{-1}$) (Mujumdar, R. B.; Ernst, L. A.; Mujumdar, S. R.; Lewis, C. J.; Waggoner, A. S. *Bioconjugate Chemistry* 1993, 4, 105-111). Quantum yields of all dyedrons at the MG excitation peak were essentially constant. Corresponding fluorescence emission spectra show almost complete transfer (>99%) of the Cy3 excitation to far red emission from the bound MG dye, and show substantial increases in the brightness of the probe constructs when used with increasing generations of the dyedron (FIG. 11B). Relative quantum yields at the Cy3 excitation and the MG excitation indicate that little donor excitation is lost to competing radiative and nonradiative processes (Table 4). These observations support the concept that even inherently non-fluorescent or self-quenched donors in dyedrons could produce highly efficient sensitizing structures for bright fluorescence (Berlier, J. E.; Rothe, A.; Buller, G.; Bradford, J.; Gray, D. R.; Filanoski, B. J.; Telford, W. G.; Yue, S.; Liu, J.; Cheung, C. Y. *Journal of Histochemistry and Cytochemistry* 2003, 51, 1699 and Hung, S.-C.; Ju, J.; Mathies, R. A.; Glazer, A. N. *Analytical Biochemistry* 1996, 243, 15-27).

TABLE 4

Relative quantum yield at common laser lines of dyedrons bound to L5-MGE52D

| Dyedron | 514 nm | 532 nm | 561 nm | 633 nm |
|---|---|---|---|---|
| M | ND | ND | 1.44 | 1.00 |
| CM | 1.24 | 1.08 | 1.41 | 1.00 |
| BCM | 0.92 | 0.86 | 1.31 | 1.00 |
| TCM | 0.96 | 0.93 | 1.09 | 1.00 |

Excitation/absorbance values were obtained by dividing excitation spectra (emission = 710 nm) by the corresponding absorbance spectra for interval 430-650 nm. Values were essentially constant over the 610-640 nm for each dyedron. Each 633 nm value was set to 1.00, to which values at other wavelengths were normalized.

When bound to E52D FAP, the absorbance of MG-2p and all dyedron MG acceptors increase nearly 2-fold and their absorbance maxima red-shift and coalesce at about 642 nm, suggesting that acceptor photophysical properties are specifically modulated by the FAP binding pocket and are largely independent of the donors. In contrast, absorbance spectra at donor wavelengths of FAP-bound dyedrons and free Cy3 have similar features, suggesting that Cy3 photophysics are not greatly altered.

Dyedron/L5-Mg E52D Fluoromodules Expressed on Live Cell Surfaces.

Figure 15:
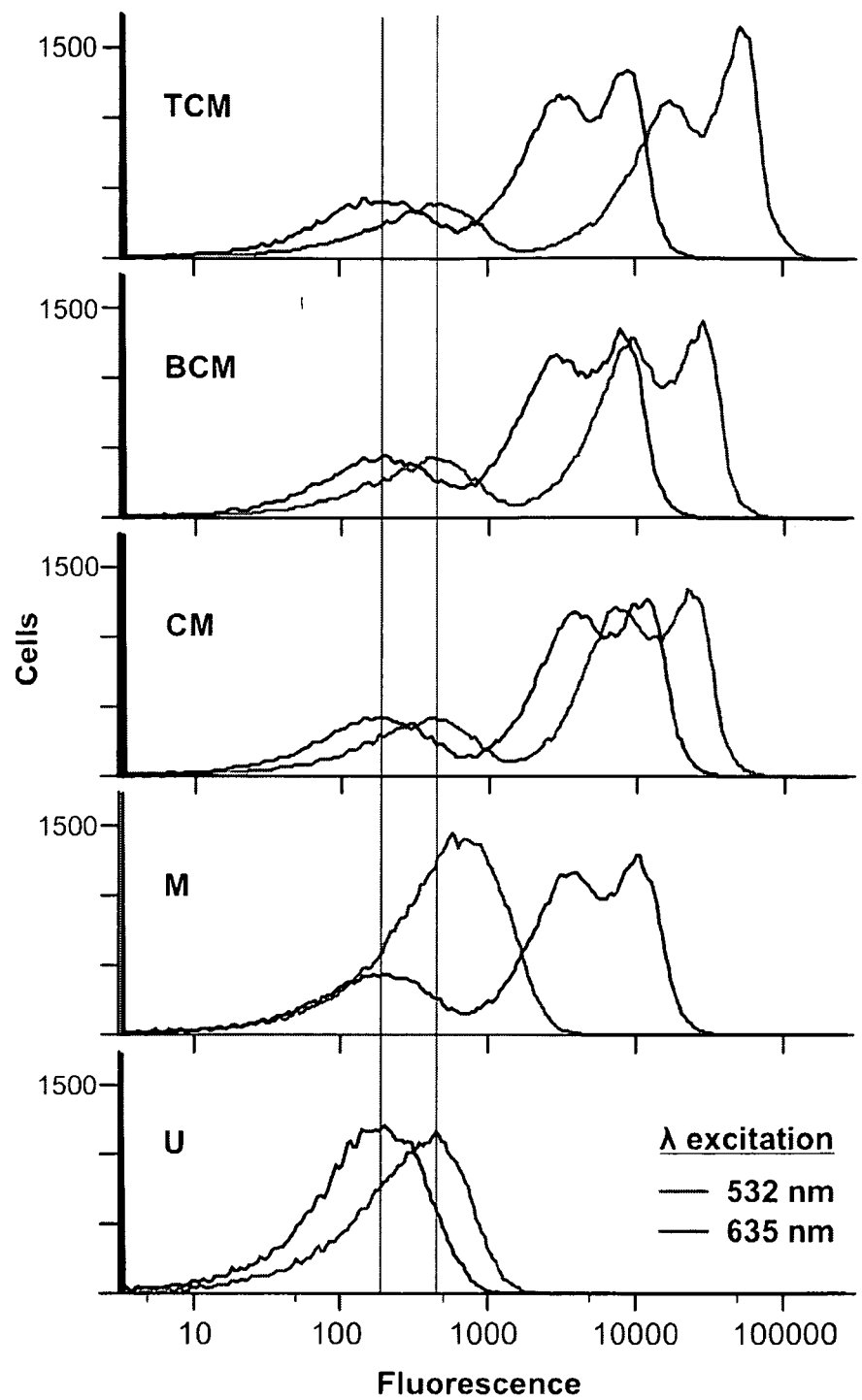
FIG. 15. Flow cytometric analysis of dyedron-labeled yeast by exciting donor (blue) or acceptor (red). *Saccharomyces cerevisiae* cells expressing L5-MG E52D on their surface were analyzed essentially as described in WO 08/092,041 and in Szent-Gyorgyi, C.; Schmidt, B. F.; Creeger, Y.; Fisher, G. W.; Zakel, K. L.; Adler, S.; Fitzpatrick, J. A. J.; Woolford, C. A.; Yan, Q.; Vasilev, K. V.; Berget, P. B.; Bruchez, M. P.; Jarvik, J. W.; Waggoner, A. *Nature Biotechnology* 2008, 26, 235-240. Two aliquots of each stained population and an unstained control (U) were respectively analyzed, exciting at 532 nm (donor) or 635 nm (acceptor), and collecting emission through a 675/50 nm bandpass (BP) filter. Each analysis comprised 100,000 cells. Stained samples contain a sub-population of non-fluorescent cells due to loss of scFv-encoding plasmid, whose signal corresponds to that of unstained samples (marked by thin lines). Controls show virtually no fluorescence generated by dyedrons on cell surfaces in the absence of expressed FAP (Table 3). Unstained cells excited at 532 nm are relatively brighter than those excited at 635 nm due to higher cellular autofluorescence at the shorter wavelength. Doublet stained peaks correspond to unbudded and budded yeast cells, and are typical for such experiments. Separation of the positive cells from negative cells remains essentially constant under 635 nm excitation but increases in proportion to the number of Cy3 donors under 532 nm excitation. The enhanced excitation in the dyedrons results in increased sensitivity in the flow cytometer.

In vitro spectroscopic properties of L5-MG E52D fluoromodules are recapitulated when dyedrons (300 nM) are directly added to suspensions of live yeast cells expressing the fluorogen activating scFv as fusion protein on the cell wall. Flow cytometry reveals step-increases in brightness when excited at 532 nm, and nearly constant brightness when excited at 635 nm (FIG. 15), corresponding well to the differences seen in the excitation spectra and the consistent quantum yields measured at 620 nm excitation. Analysis of the staining ratio between yeast cells excited at 635 nm vs 532 nm reveals an increase in specific brightness by a factor of about 2 (n=1), 3 (n=2), and 7 (n=4) in the (Cy3)$_n$MG construct (Table 2 and Table 3). Hence, this approach increases molecular brightness in vitro and in vivo in direct correlation with the enhanced extinction provided by the donor array.

Figure 14:
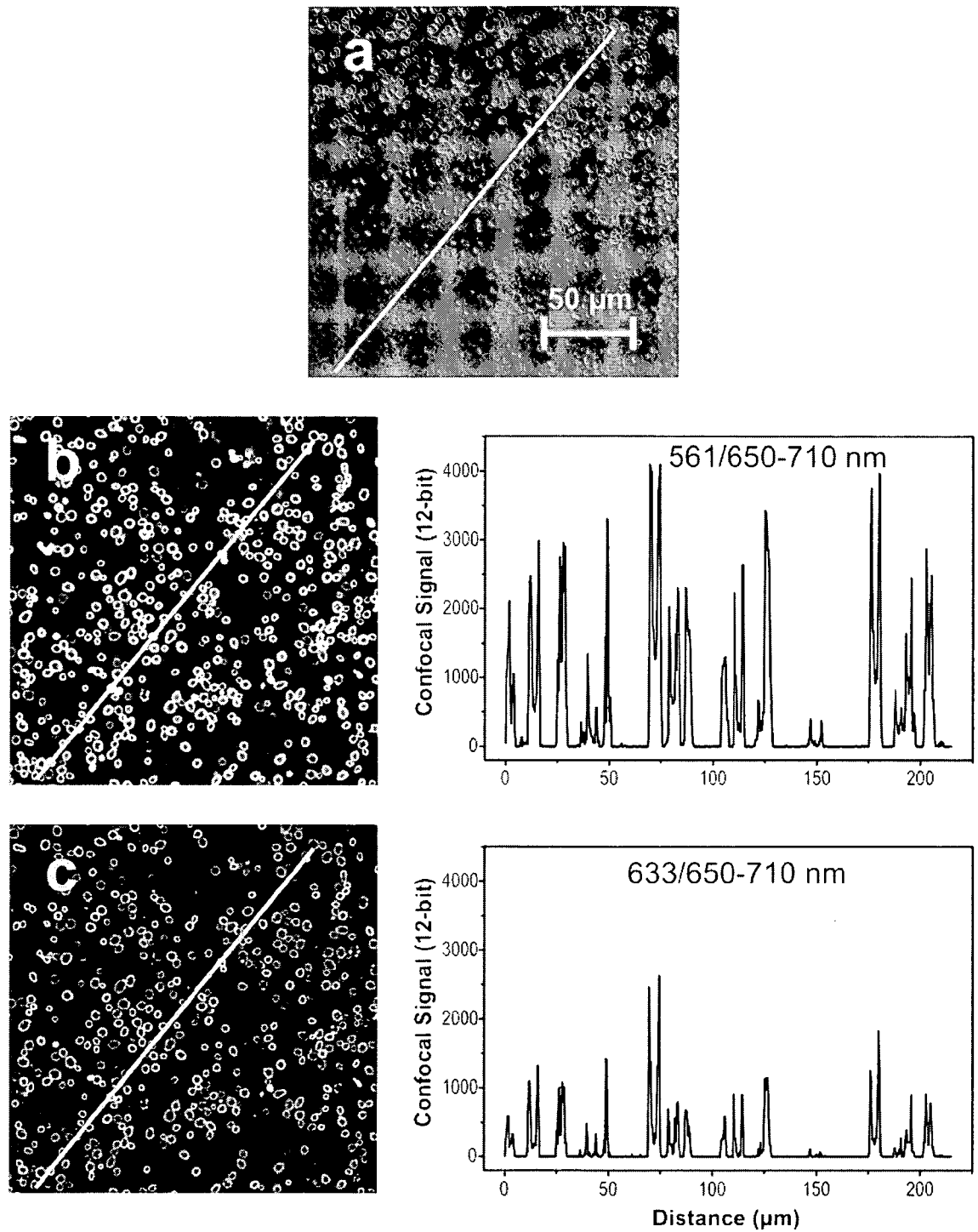
FIG. 14. Fluorescence imaging of yeast cells surface displaying L5-MG E52D. Live yeast cells were imaged in the presence of 500 nM TCM on a Zeiss 510 MetaNLO confocal microscope using differential interference contrast (DIC) (a), or fluorescence at donor (561/650-710 BP) (b), or acceptor (633/650-710 BP) (c) excitation/emission settings. Accompanying 12-bit scan profiles quantify signal/noise characteristics of cells transected by yellow lines.

Dyedron-mediated signal amplification can also be applied to live cell fluorescence microscopy. Yeast cells expressing the L5-MG E52D fusion protein (Szent-Gyorgyi, C.; Schmidt, B. F.; Creeger, Y.; Fisher, G. W.; Zakel, K. L.; Adler, S.; Fitzpatrick, J. A. J.; Woolford, C. A.; Yan, Q.; Vasilev, K. V.; Berget, P. B.; Bruchez, M. P.; Jarvik, J. W.; Waggoner, A. *Nature Biotechnology* 2008, 26, 235-240, see FIG. 4A for sequence, SEQ ID NOS: 1 and 2 and see also WO 2008/092041 for additional examples of useful fusion proteins between an scFv activator and selectivity components) on their surface were imaged under a laser scanning confocal microscope (FIG. 14). Yeast cells are specifically labeled on their surface, and when imaged with 561 nm excitation consume the full dynamic range of the 12-bit image. Virtually no fluorescence is detected from cells not expressing FAP or from intercellular regions. Some selective bleaching of the dyedron is observed under this laser illumination, reducing dyedron enhancement to about 3-fold.

Further Improving Dyedron Fluoromodules by Directed Evolution.

Figure 16A:
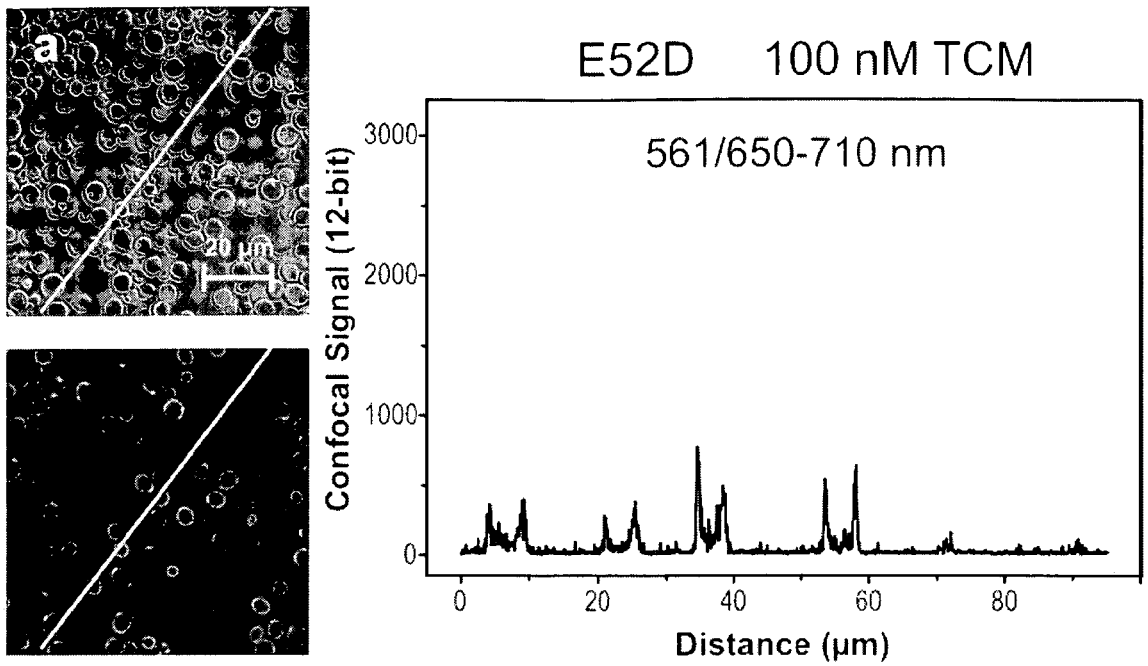
FIG. 16. Live cell surface imaging with improved fluoromodules.
Figure 16B:
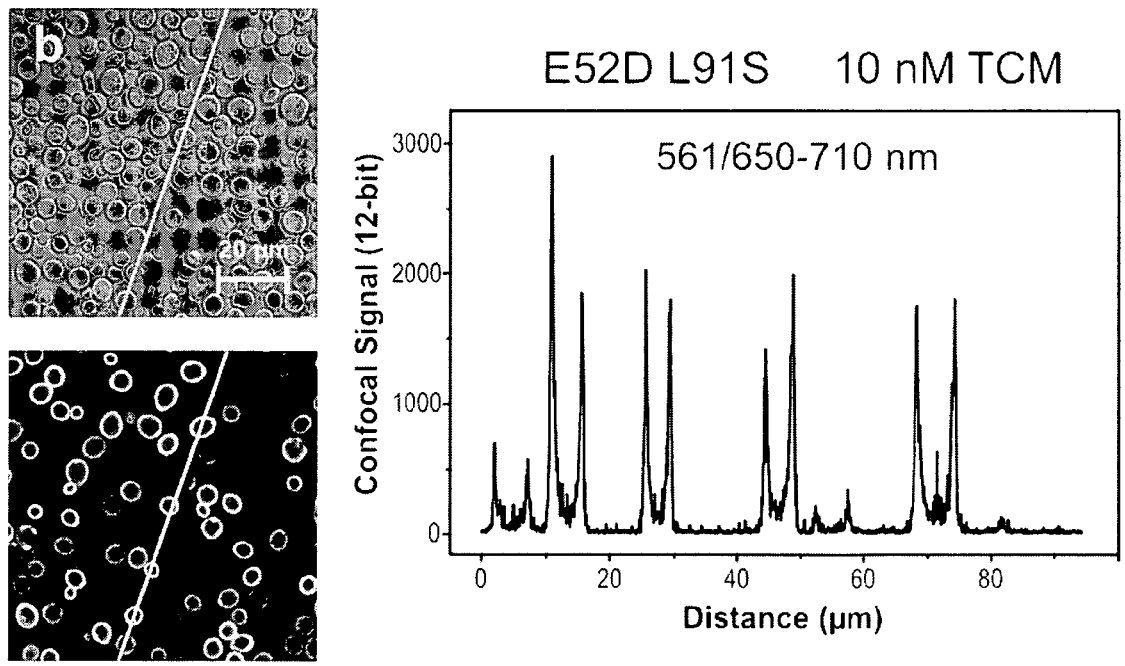
Figure 16C:
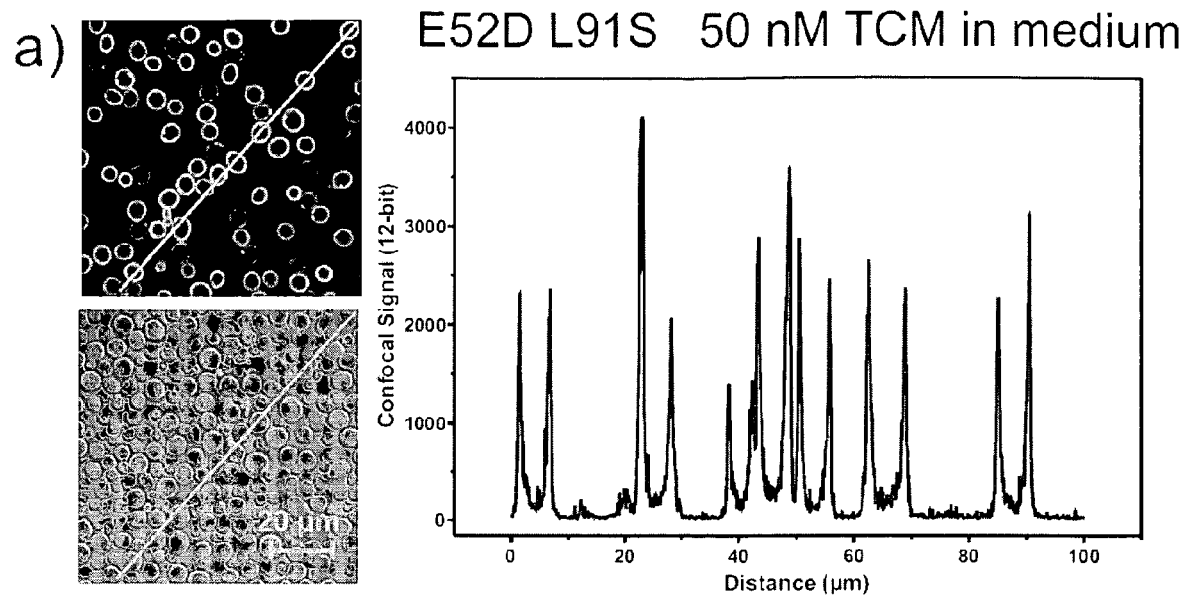
Figure 16D:
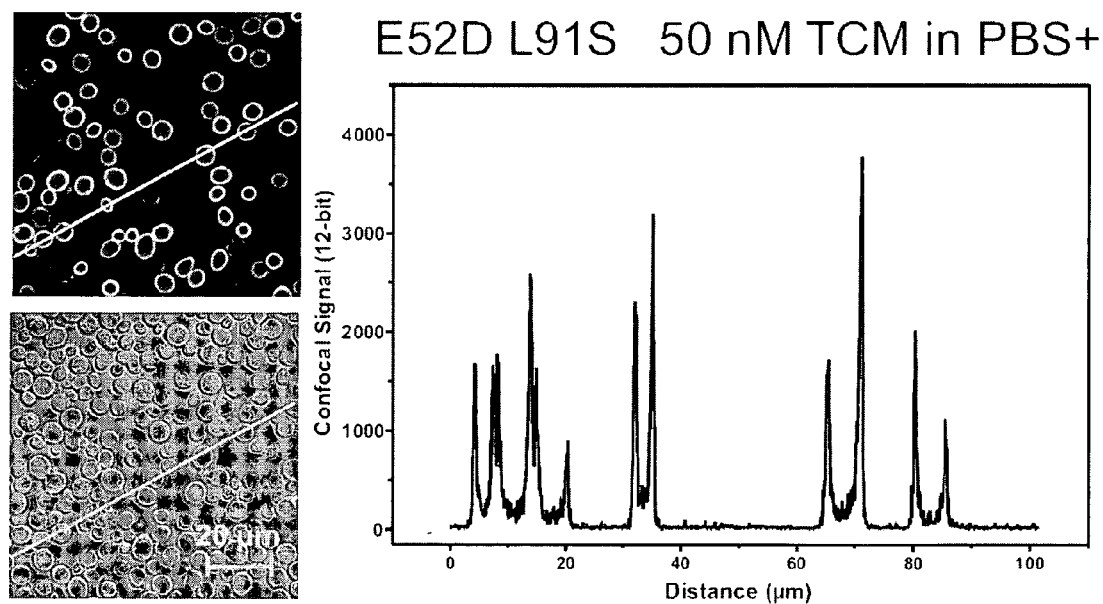

The MG-2p/L5-MG E52D fluoromodule has a modest quantum yield, yet the TCM dyedron can amplify its signal to give a calculated molecular brightness about that of EGFP and most small molecule protein tags (Table 2). Among our affinity matured L5-MG FAPs, we characterized L5-MG L91S, which contains a single point mutation that increases quantum yield of the MG-2p/L5-MG fluoromodule several-fold, but binds MG-2p and dyedrons rather loosely. However, as compared to the E52D FAP, the L91S and E52D mutations in combination behave additively to create a FAP that binds TCM with similar affinity and yields almost 6-fold greater fluorescence when assayed using live yeast in a microplate format (FIG. 13). The improved fluorescence properties of L5-MG E52D L91S are evident when imaging the surface of live yeast using much lower concentrations of dyedron (FIGS. 16A and 16B), even in growth media (FIGS. 16C and 16D).

FIGS. 16A-16D show Live cell surface imaging with improved fluoromodules. Yeast cells expressing L5-MG carrying E52D (16A) or E52D L91S (16B) mutations were imaged in PBS+ on a Zeiss 510 MetaNLO confocal microscope with identical Cy3 excitation/emission settings using the indicated TCM concentrations. Scan profiles show that fluorescence of the E52D L91S double mutant at 10 nM TCM is about 5-fold greater than E52D fluorescence at 10-fold higher TCM. Weak apparent fluorescence of E52D fluoromodule as compared to FIG. 14 is due to different microscope settings, and not reduced binding of TCM (FIG. 13). The sub-population of yeast cells that do not express FAP display no fluorescence, and constitute an internal control for specificity.

Dyedron-based imaging of yeast in growth medium. Yeast grown in SGR+CAA medium to induce expression of L5-MG E52D L91S scFv were directly affixed to a concanavalin A coated MatTek dish and overlain with 1 ml of the same medium containing 50 nM TCM. Signal profile plot of confocal image taken at 561/650-710 BP excitation/emission settings reveals surface confined fluorescence with very low intercellular background signal (FIG. 16C). Under identical imaging conditions, substituting PBS+ for growth medium gives essentially the same result (FIG. 16D) show the same in media.

DISCUSSION

These dyedrons represent a new class of fluorescent detection reagent, where a specific genetically targetable and switchable acceptor chromophore is enhanced for efficient excitation by energy transfer from covalently attached donor molecules. The overall molecular weight of these synthetic macromolecules remains small, especially compared to alternative approaches for improving the brightness of genetically targeted fluorescent probes. Furthermore, the genetic fusion protein required to activate these dyedrons can be less than half the size of GFP (<13 kDa here). These dyedrons greatly enhance the in vivo fluorescence of fluorogen/FAP complexes, as shown by the flow cytometry, microplate assays and microscopy described here. The TCM/L5-MG E52D L91S fluoromodule has an estimated brightness value (160) that is nearly 5-fold higher than EGFP (Table 2) and the red fluorescent biarsenical complex (ReAsH=34) (Martin, B. R.; Giepmans, B. N. G.; Adams, S. R.; Tsien, R. Y. *Nature Biotechnology* 2005, 23, 1308-1314), and about 10-fold brighter than the best available monomeric red fluorescent protein (mCherry=16) (Shaner, N.C.; Campbell, R. E.; Steinbach, P. A.; Giepmans, B. N. G.; Palmer, A. E.; Tsien, R. Y. *Nature Biotechnology* 2004, 22, 1567-1572). The dyedron fluoromodules have a long Stokes-shift and far-red emission (660 nm versus 610 nm for mCherry and ReAsH) that ensures that these probes provide substantial improvements in sensitivity (Özhalici-Ünal, H.; Pow, C. L.; Marks, S. A.; Jesper, L. D.; Silva, G. L.; Shank, N. I.; Jones, E. W.; Burnette Iii, J. M.; Berget, P. B.; Armitage, B. A. *Journal of the American Chemical Society* 2008, 130, 12620 and Chao, G.; Lau, W. L.; Hackel, B. J.; Sazinsky, S. L.; Lippow, S. M.; Wittrup, K. D. *Nature Protocols* 2006, 1, 755-768). With dyedrons, binding of the fluorogen to the target peptide also brings the donor array into the binding site vicinity, reducing the overall peptide-fluorogen affinity (Table 2), but the stability of these complexes remains high (<20 nM for the E52D mutant). Such functional variation can be corrected or exploited by the directed evolution of scFvs or other recognition scaffolds.

Variation in donor chemistry can thus be combined with variation in fluorogen/peptide interaction to improve dyedron properties. One can select for improved fluorogen binding affinity and quantum yield in the context of a given donor array. The donor array can be designed to enhance the extinction coefficient, but may also be designed to improve other optical properties, such as enhancing the multiphoton cross-section of specific fluorogens.

The membrane impermeant nature of these dyedrons makes them ideal for studying a wide range of biological functions involving plasma membrane proteins that have exposed extracellular domains available for genetic fusion. Among these are receptors that mediate intercellular signaling, ion and metabolite transport channels, and cellular recognition and adhesion proteins. Exclusive labeling of extracellular domains confines detection of these proteins to the site of their biological function. In contrast, fusions of fluorescent proteins to these same extracellular domains would also be subject to detection during biosynthesis and intracellular transport, generating background signal unrelated to function at the cell surface (Szent-Gyorgyi, C.; Schmidt, B. F.; Creeger, Y.; Fisher, G. W.; Zakel, K. L.; Adler, S.; Fitzpatrick, J. A. J.; Woolford, C. A.; Yan, Q.; Vasilev, K. V.; Berget, P. B.; Bruchez, M. P.; Jarvik, J. W.; Waggoner, A. *Nature Biotechnology* 2008, 26, 235-240 and Szidonya, L.; Cserzo, M.; Hunyady, L. *Journal of Endocrinology* 2008, 196, 435-53). The dyedrons described herein, like their counterpart MG-2p, can be added to cell culture media directly without washes or other treatments, distinguishing these fluorogens from other small molecule labeling methods that have been applied to membrane proteins. Enhanced sensitivity of expressible probes will reduce the need for high level overexpression in cell-biological investigations (Szidonya, L.; Cserzo, M.; Hunyady, L. *Journal of Endocrinology* 2008, 196, 435-53), and provides an alternative labeling approach that may reduce artifacts related to expression level. Injection into transgenic animals is potentially feasible because these dyedrons are small enough to efficiently penetrate intercellular space in tissues (Rao, B. M.; Lauffenburger, D. A.; Wittrup, K. D. *Nature Biotechnology* 2005, 23, 191-194).

The dyedrons described here currently provide the optimal signal enhancement to applications such as flow cytometry and microplate assays, where individual fluoromodules are subjected to moderate total excitation flux. Future work will address improving dyedron photostability under the intense illumination typical of confocal fluorescence microscopy, possibly by addition of electron-withdrawing groups to Cy3 donors (Shank, N. I.; Zanotti, K. J.; Lanni, F.; Berget, P. B.; Armitage, B. A. *Journal of the American Chemical Society* 2009, 131, 12960-12969) or by directed evolution of the FAP to increase the on/off rate of dyedron binding, thereby continuously regenerating functional fluoromodules (Szent-Gyorgyi, C.; Schmidt, B. F.; Creeger, Y.; Fisher, G. W.; Zakel, K. L.; Adler, S.; Fitzpatrick, J. A. J.; Woolford, C. A.; Yan, Q.; Vasilev, K. V.; Berget, P. B.; Bruchez, M. P.; Jarvik, J. W.; Waggoner, A. *Nature Biotechnology* 2008, 26, 235-240).

Fluorogen-activating scFvs contain internal disulfide linkages that may compromise function in the cytoplasm and other intracellular reducing environments; directed evolution may be employed to remove such disulfides and adapt scFvs to intracellular function (Fitzpatrick, J. A. J.; Yan, Q.; Sieber, J. J.; Dyba, M.; Schwarz, U.; Szent-Gyorgyi, C.; Woolford, C.

A.; Berget, P. B.; Waggoner, A. S.; Bruchez, M. P. *Bioconjugate Chemistry* 2009, 20, 1843-1847 and Colby, D. W.; Chu, Y. J.; Cassady, J. P.; Duennwald, M.; Zazulak, H.; Webster, J. M.; Messer, A.; Lindquist, S.; Ingram, V. M.; Wittrup, K. D. *Proceedings of the National Academy of Sciences* 2004, 101, 17616). It would then be desirable to introduce dyedrons into the cell for maximum utility. Several approaches to transmembrane delivery are available, including microinjection, pore formation, modifying dyedron physicochemical properties, adding transport signals to dyedrons, or creating dyedron-carrier vesicles or emulsions able to fuse with the plasma membrane. The low activation of dyedrons shown here on microinjection indicates that intracellular use remains largely a problem of delivery, not one of specificity.

For all references incorporated herein by reference, this document is to control with respect to any conflicting terms, concepts or definitions.

---

We claim:

1. A compound comprising an activatable acceptor moiety covalently attached to a linker, and a plurality of donor moieties covalently attached to the linker, wherein
   (a) the acceptor moiety is a triarylmethine dye, and
   (b) the donor moieties are Cy3 dyes, and
   wherein the Cy3 dyes, when excited, transfer at least 50% of their excitation energy to the triarylmethine dye, and when activated, the triarylmethine dye produces a detectable fluorescence signal different from the signal produced when the triarylmethine dye is not activated.

2. The compound of claim 1, in which the triarylmethine dye is chosen from malachite green, or acetylenic malachite green.

3. The compound of claim 1 in which the triarylmethine dye is malachite green.

4. The compound of claim 1 having an average molecular weight of less than 50 kDa (kilodaltons).

5. The compound of claim 1 having an average molecular weight of less than 10 kDa.

6. The compound of claim 1, comprising one or more mediators, wherein the spectrum of the Cy3 dyes overlaps the spectrum of the mediators and the spectrum of the mediators overlaps the spectrum of both the Cy3 dyes and the triarylmethine dye.

7. The compound of claim 1, in which the triarylmethine dye is

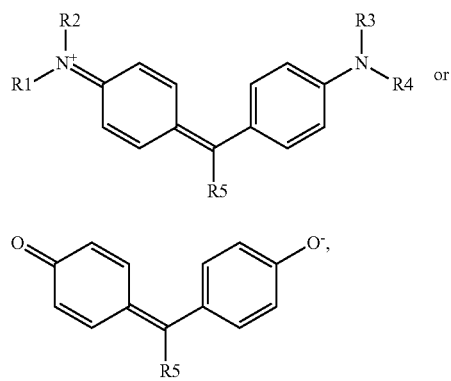

in which R1-R4 are —H, —CH$_3$, (CH$_2$)$_n$-T, or substituted aryl, and R5 is a substituted aryl chosen from:

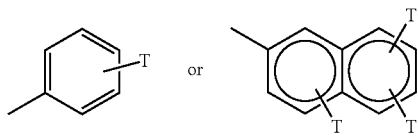

where, for R1-R5, n=0-6 and T is selected from —H, —OH, —COO$^-$, —SO$_3^-$, —PO$_4^{2-}$, amide, halogen, substituted single or multiple aryl, ether, polyether, PEG$_{1-30}$, heterocyles containing N, S or O atoms, substituted acetylenic groups, cyano, or carbohydrate groups.

8. The compound of claim 1, in which the triarylmethine dye is:

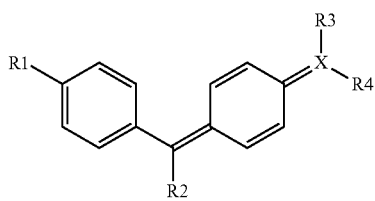

where R1 is aryl, heteroaryl, hydroxyl, amino, N-alkyl, or N-alkanolyl, R2 is H, cyano, aryl, heteroaryl, alkynyl, or alkyl, X is N, O, or S and R3 and R4 are absent or are alkyl, aryl, or hydroxyethyl.

9. The compound of claim 8 in which R1 is di-C$_{1-3}$ alkylamino, R2 is a substituted phenylacetylene, phenyl, N-alkyl-substituted phenyl, or —O(CH$_2$)$_n$R5 substituted phenyl where n is 1-5 and R5 is carboxyl or amino, X is N, and R3 and R4 are independently C$_{1-3}$ alkyl, alkoxyl, alkanolyl, phenyl, or C$_{1-3}$ alkyl-substituted phenyl.

10. The compound of claim 9 in which R2 is the substituted phenylacetylene substituted with —N—(CH$_3$)$_2$ or —N—(CH$_3$)((CH$_2$)$_n$O(CH$_2$)$_m$COOH) in which n and m are independently 1, 2, 3 or 4.

11. The compound of claim 9 in which R1 is —N(CH$_3$)$_2$, R2 is —O(CH$_2$)$_3$R5 substituted phenyl or

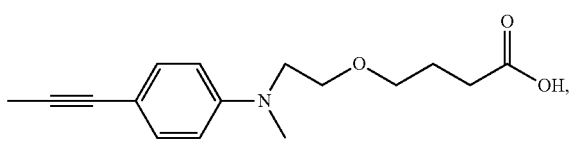 [SMILES: CC#Cc1ccc(N(C)CCOCCCC(=O)O)cc1]

and R3 and R4 are CH$_3$.

12. The compound of claim 9 in which the triarylmethine dye is a compound selected from the group consisting of:

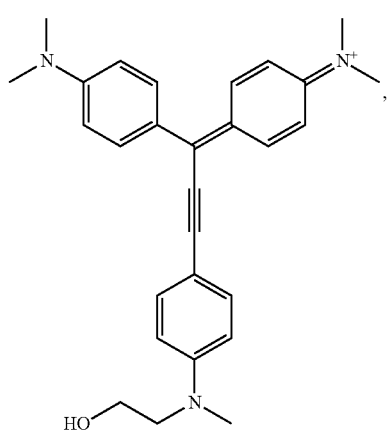

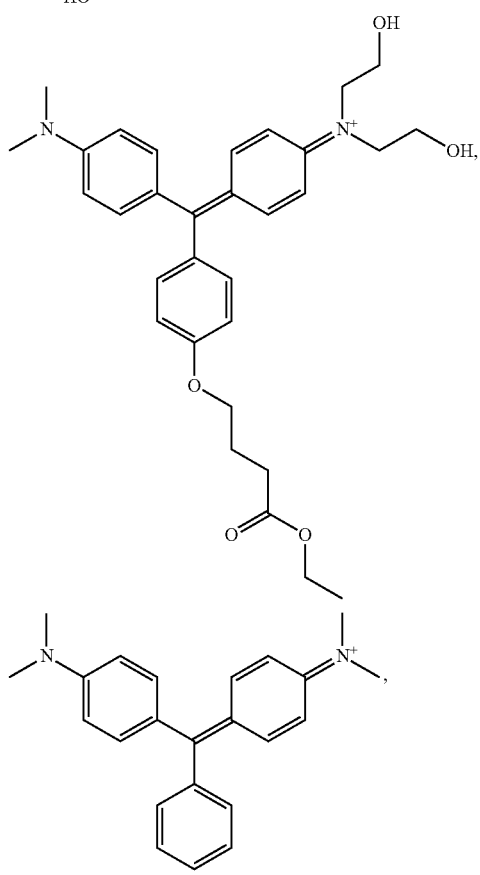

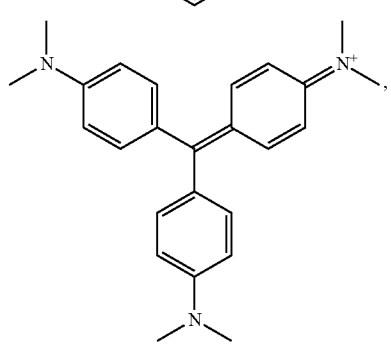

-continued

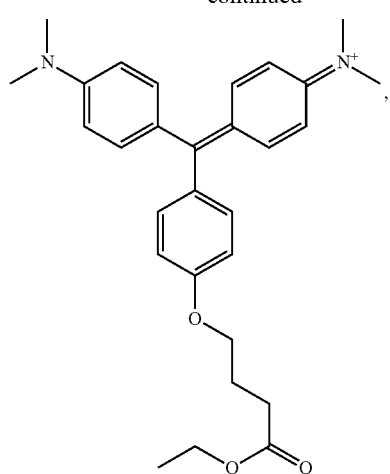

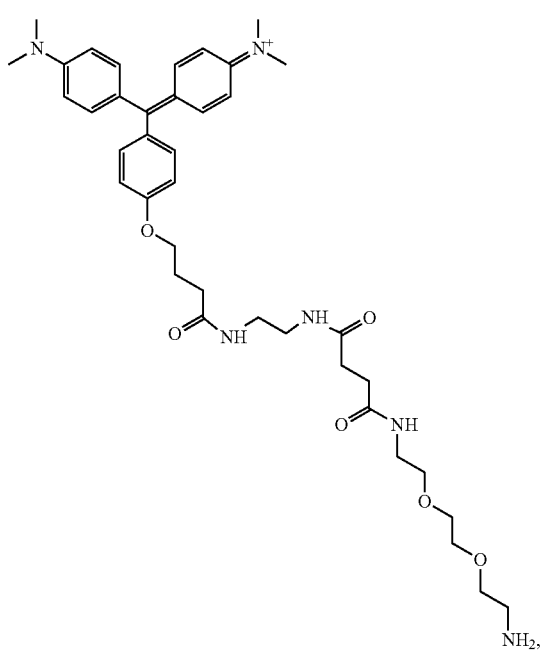

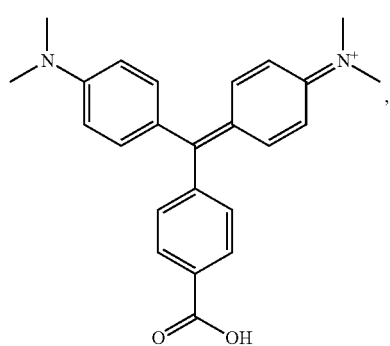

-continued

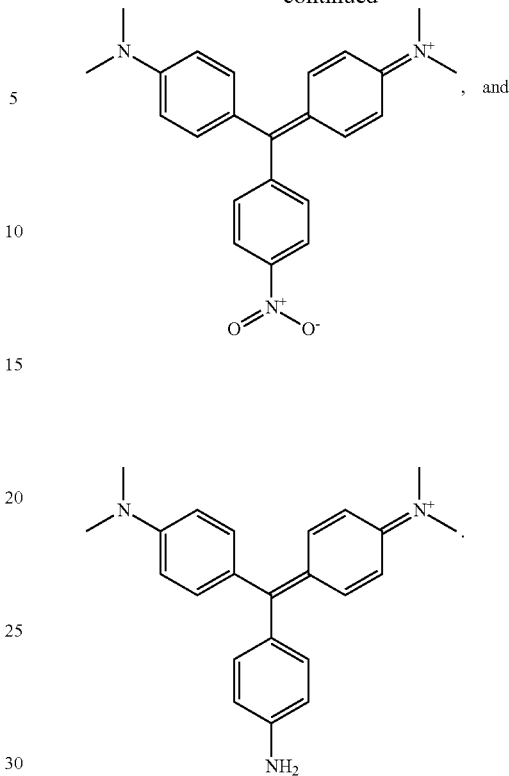

13. The compound of claim 1, in which the detectable fluorescence signal change is a change in intensity of fluorescence.

14. The compound of claim 1, in which the triarylmethine dye is activated by binding.

15. The compound of claim 1, wherein the linker comprises a tris(oxymethyl)methylamino (TRIS) tripod linker.

16. The compound of claim 15, wherein the TRIS tripod linker connects up to 6 of the Cy3 dyes to the triarylmethine dye.

17. The compound of claim 15, wherein the TRIS tripod linker is connected to one or more ((1,3-diaminopropan-2-yl)oxy)acetamido T-linkers.

18. The compound of claim 1, wherein the linker comprises a poly(amidoamine) (PAMAM) dendron.

19. The compound of claim 18, wherein the PAMAM dendron connects up to 16 of the Cy3 dyes to the triarylmethine dye.

20. The compound of claim 19, wherein the PAMAM dendron connects from 6 to 16 of the Cy3 dyes to the triarylmethine dye.

21. The compound of claim 1, wherein the linker comprises a poly(ethylene imine) (PEI) dendron, a poly(propylene imine) (PPI) dendron, a Newkome dendron, a 2,2-bis(methylol)propionic acid (bis-MPA) dendron, or a polyphenylene dendron.

22. A compound having the following structure:
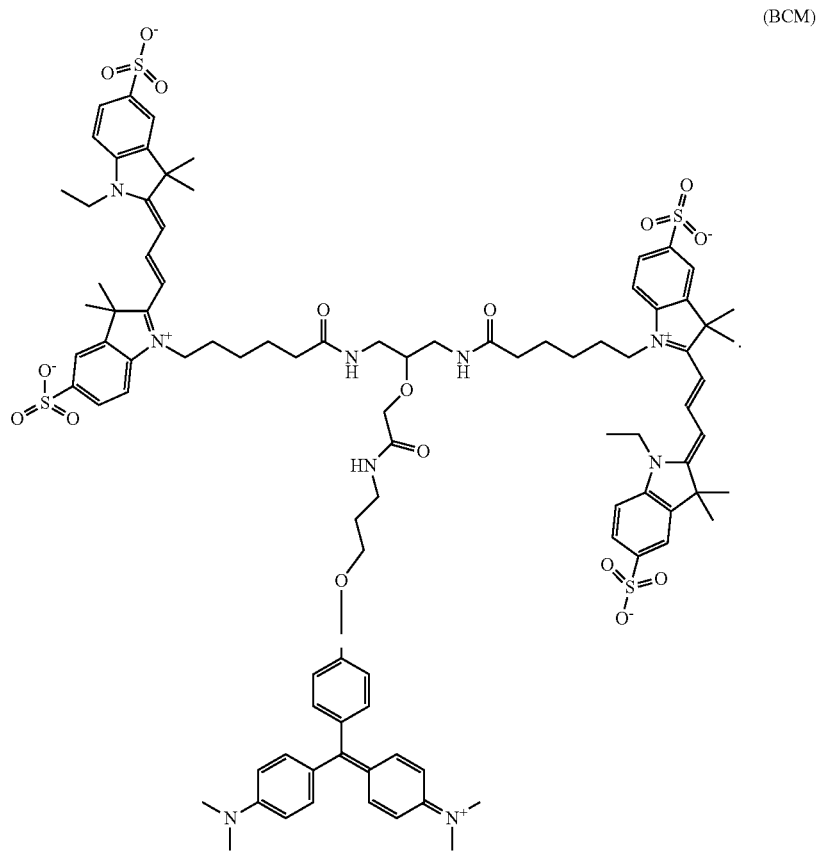
(BCM)

23. A compound having the following structure:

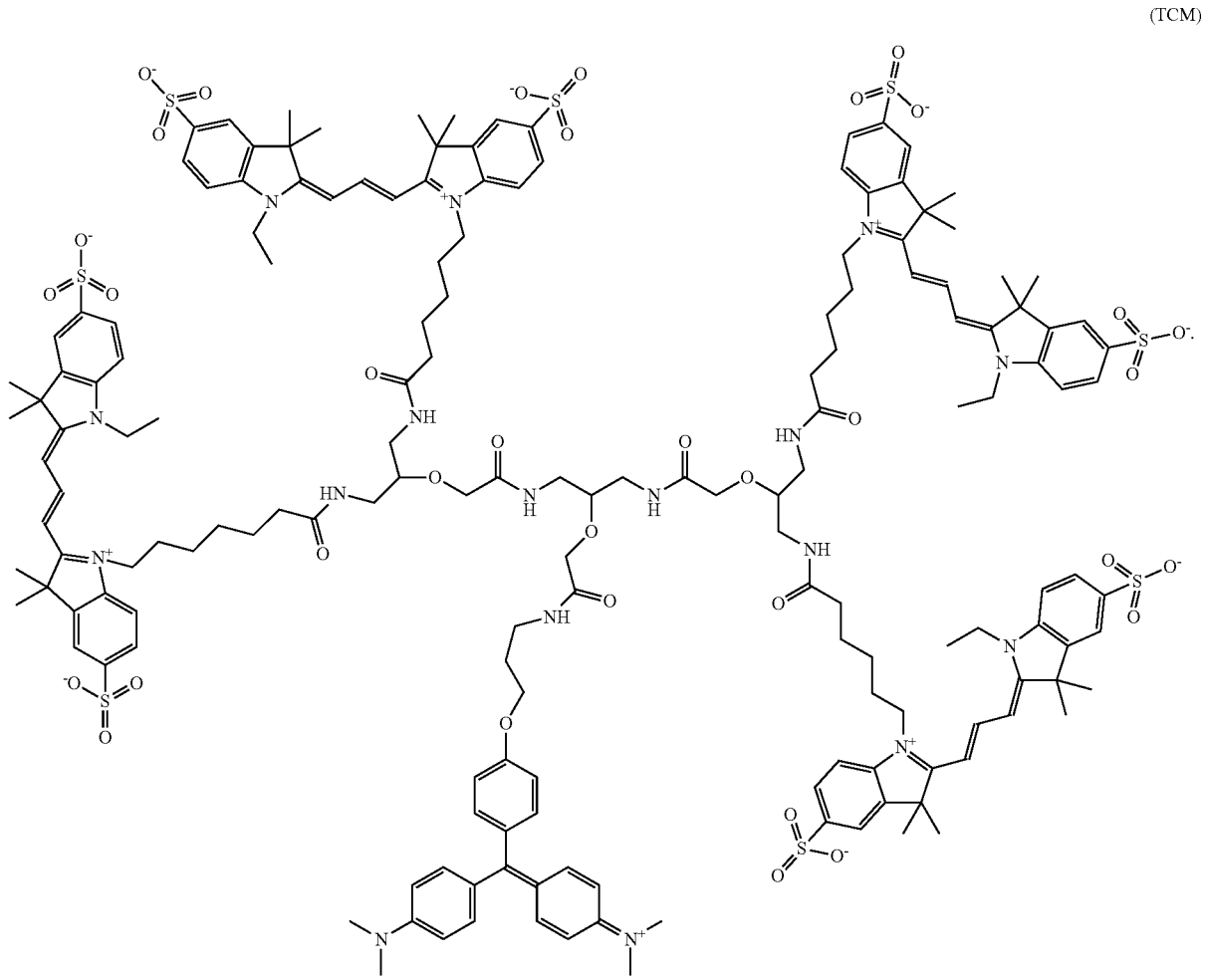

(TCM)

24. A complex comprising the compound of claim 1 bound to an activator that causes an increase of fluorescence of the compound of claim 1 when the activator is bound to the compound of claim 1 when the Cy3 dyes are excited.

25. The complex of claim 24, in which the increase in fluorescence is at least 100-fold.

26. The complex of claim 24, in which the increase in fluorescence is at least 1000-fold.

27. The complex of claim 24, in which the activator is attached to a selectivity component.

28. The complex of claim 27, in which the activator and the selectivity component are part of a fusion protein.

29. The complex of claim 27, in which the selectivity component is crosslinked to the activator.

30. The complex of claim 24 in which the activator is an scFv fragment.

31. The complex of claim 24 in which the activator is one of SEQ ID NOS: 3-11.

32. The complex of claim 27 in which the linker is a PAMAM dendron and the triarylmethine dye is malachite green.

33. The complex of claim 31 in which the compound of claim 1 is BCM or TCM.

34. A method of identifying a cellular component in a cell comprising contacting the compound of claim 1 with a fusion protein comprising a selectivity component attached to an activator of the compound of claim 1 and the cell to produce a dyedron complex with the cellular component in the cell and detecting the dyedron complex with the cellular component in the cell.

35. The method of claim 34 in which the selectivity component and the activator are on a contiguous polypeptide.

36. The method of claim 34 in which the activator is an scFv fragment.

37. The method of claim 35 wherein the contiguous polypeptide is produced by a gene introduced into the cell.

38. The method of claim 34 in which the triarymethine dye is malachite green.

39. The method of claim 38 in which the activator is a polypeptide comprising one or more of SEQ ID NOs. 3-9.

40. The method of claim 38 in which the compound of claim 1 is TCM or BCM.

41. The method of claim 34 in which the dyedron complex with the cellular component in the cell is detected by fluorescent imaging.

* * * * *

UNITED STATES PATENT AND TRADEMARK OFFICE
CERTIFICATE OF CORRECTION

PATENT NO. : 9,249,306 B2  
APPLICATION NO. : 13/201226  
DATED : February 2, 2016  
INVENTOR(S) : Marcel P. Bruchez et al.

It is certified that error appears in the above-identified patent and that said Letters Patent is hereby corrected as shown below:

In the claims,

Column 55, Line 16, Claim 7, delete "heterocyles" and insert -- heterocycles --

Column 61, Line 61, Claim 32, delete "claim 27" and insert -- claim 31 --

Column 62, Line 56, Claim 38, delete "triarymethine" and insert -- triarylmethine --

Signed and Sealed this  
Ninth Day of August, 2016

Michelle K. Lee  
*Director of the United States Patent and Trademark Office*